(12) United States Patent
Takeuchi et al.

(10) Patent No.: US 12,239,090 B2
(45) Date of Patent: Mar. 4, 2025

(54) **PLANT BODY OF GENUS *NICOTIANA* WITH LOW ALKALOID CONTENT AND PRODUCTION METHOD THEREOF**

(71) Applicant: JAPAN TOBACCO INC., Tokyo (JP)

(72) Inventors: Takanori Takeuchi, Tokyo (JP); Masao Arai, Tokyo (JP); Hisashi Udagawa, Tokyo (JP); Hiroshi Magome, Tokyo (JP); Ryo Nishiguchi, Tokyo (JP); Yoshimitsu Takakura, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 73 days.

(21) Appl. No.: 17/965,450

(22) Filed: Oct. 13, 2022

(65) Prior Publication Data

US 2023/0120622 A1   Apr. 20, 2023

Related U.S. Application Data

(63) Continuation of application No. PCT/JP2021/015920, filed on Apr. 19, 2021.

(30) Foreign Application Priority Data

Apr. 17, 2020   (JP) ................................ 2020-074233

(51) Int. Cl.
*A01H 6/82*    (2018.01)
*C12N 15/82*   (2006.01)

(52) U.S. Cl.
CPC ......... *A01H 6/823* (2018.05); *C12N 15/8243* (2013.01)

(58) Field of Classification Search
None
See application file for complete search history.

(56) References Cited

U.S. PATENT DOCUMENTS

| | | | |
|---|---|---|---|
| 2013/0056014 A1 | 3/2013 | Noguchi et al. | |
| 2016/0272984 A1 | 9/2016 | Noguchi et al. | |
| 2019/0218564 A1 | 7/2019 | Suzuki et al. | |
| 2020/0382523 A1 | 12/2020 | Suzuki et al. | |

FOREIGN PATENT DOCUMENTS

| | | |
|---|---|---|
| CN | 108882689 A | 11/2018 |
| WO | WO 2006/109197 A2 | 10/2006 |
| WO | WO 2011/102394 A1 | 8/2011 |
| WO | WO 2018/222667 A1 | 12/2018 |
| WO | WO 2021/113337 A1 | 6/2021 |
| WO | WO 2023/015712 A1 | 2/2023 |

OTHER PUBLICATIONS

Martinez, H.D. et al., (2020) Planta vol. 251, No. 92 incl. suppl. 30 pages. (Year: 2020).*
Belhaj, K. et al., Plant Methods (2013) vol. 9, No. 39 pp. 1-10. (Year: 2013).*
Martinez, H.D. et al., Planta (2020) vol. 9, No. 39: pp. 1-10. (Year: 2020).*
Chinese Office Action and Search Report for Chinese Application No. 202180028659.6, dated Mar. 11, 2023, with an English translation.
Abe et al., "Genome sequencing reveals agronomically important loci in rice using MutMap," Nature Biotechnology, vol. 30, No. 2, 2012, pp. 174-179.
Brogna et al., "Nonsense-mediated mRNA decay (NMD) mechanisms," Nature Structural & Molecular Biology, vol. 16, No. 2, 2009, pp. 107-113.
Chen et al., "Analysis of Minor Alkaloids in Tobacco: A Collaborative Study*," Beiträge zur Tabakforschung International/Contributions to Tobacco Research, vol. 21, No. 7, 2005, pp. 369-379.
Hao et al., "Characterization of L-aspartate oxidase from *Arabidopsis thaliana*," Plant Science, vol. 271, 2018, pp. 133-142.
Hayashi et al., "Genetic Manipulation of Transcriptional Regulators Alters Nicotine Biosynthesis in Tobacco," Plant Cell Physiology, vol. 61, No. 6, 2020, pp. 1041-1053.
International Search Report for International Application No. PCT/JP2021/015920, dated Jun. 15, 2021, with an English translation.
Kajikawa et al., "Genomic Insights into the Evolution of the Nicotine Biosynthesis Pathway in Tobacco," Plant Physiology, vol. 174. 2017, pp. 999-1011.
Katoh et al., "Early Steps in the Biosynthesis of NAD in *Arabidopsis* Start with Aspartate and Occur in the Plastid," Plant Physiology, vol. 141, 2006, pp. 851-857.
Khan et al., "Cloning and functional characterization of quinolinic acid phosphoribosyl transferase (QPT) gene of Nicotiana tabacum," Physiologia Plantarum, vol. 160, 2017, pp. 253-265.
Lewis, "Potential Mandated Lowering of Nicotine Levels in Cigarettes: A Plant Perspective," Nicotine & Tobacco Research, 2018, pp. 1-5.
Liedschulte et al., "Impairing both HMA4 homeologs is required for cadmium reduction in tobacco," Plant, Cell and Environment, vol. 40, 2017, pp. 364-377.
Martinez et al., "Genetic attenuation of alkaloids and nicotine content in tobacco (*Nicotiana tabacum*)," Planta, vol. 251, No. 92, 2020, pp. 1-14.
Schachtsiek et al., "Nicotine-free, nontransgenic tobacco (*Nicotiana tabacum* L.) edited by CRISPR-Cas9," Plant Biotechnology Journal, vol. 17, 2019, pp. 2228-2230.
Tajima et al., "Construction of Mutant Panel in *Nicotiana tabacum* L.," Journal of General Plant Pathology, vol. 77, No. 3, 2011, p. 258, with a partial English translation.
Wang et al., "Generation of tobacco lines with widely different reduction in nicotine levels via RNA silencing approaches," Journal of Biosciences, vol. 33, No. 2, 2008, pp. 177-184.

(Continued)

*Primary Examiner* — Russell Kallis
(74) *Attorney, Agent, or Firm* — Birch, Stewart, Kolasch & Birch, LLP

(57) ABSTRACT

An embodiment of the present invention provides a tobacco plant having a low alkaloid content. In the tobacco plant, a function of a gene encoding aspartate oxidase AO2 is suppressed.

17 Claims, 5 Drawing Sheets
Specification includes a Sequence Listing.

(56) References Cited

OTHER PUBLICATIONS

Wesley et al., "Construct design for efficient, effective and high-throughput gene silencing in plants," The Plant Journal, vol. 27, No. 6, 2001, pp. 581-590.
Xu et al., "Wild tobacco genomes reveal the evolution of nicotine biosynthesis," PNAS, vol. 114, No. 23, 2017, pp. 6133-6138.
Extended European Search Report for European Application No. 21789517.6, dated Apr. 22, 2024.
Payyavula, "Tobacco aspartate oxidase (AO)-1 protein," Database Geneseq [Online], XP93147376, Database Accession No. BJL45849, Jul. 22, 2021, 1 page total.
Payyavula, "Tobacco aspartate oxidase (AO)-2 protein," Database Geneseq [Online], XP093147382, retrieved from EBI Database Accession No. BJL45851, Jul. 22, 2021, 1 page total.

\* cited by examiner

FIG. 2
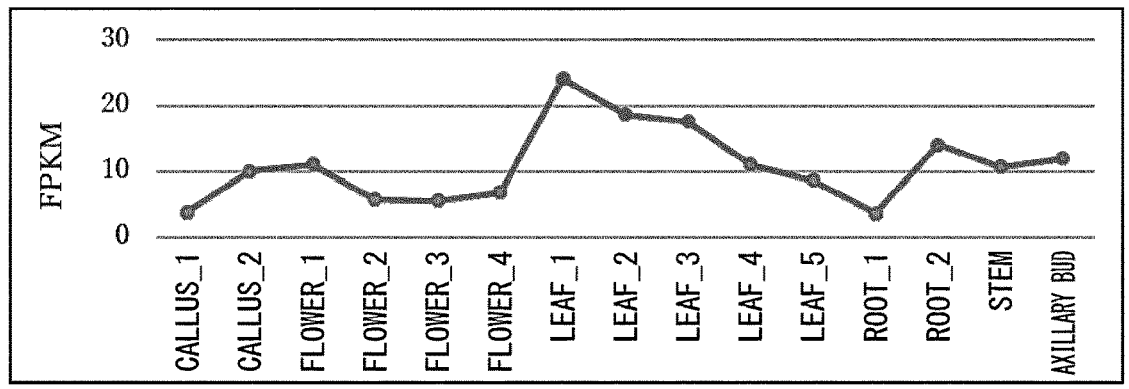
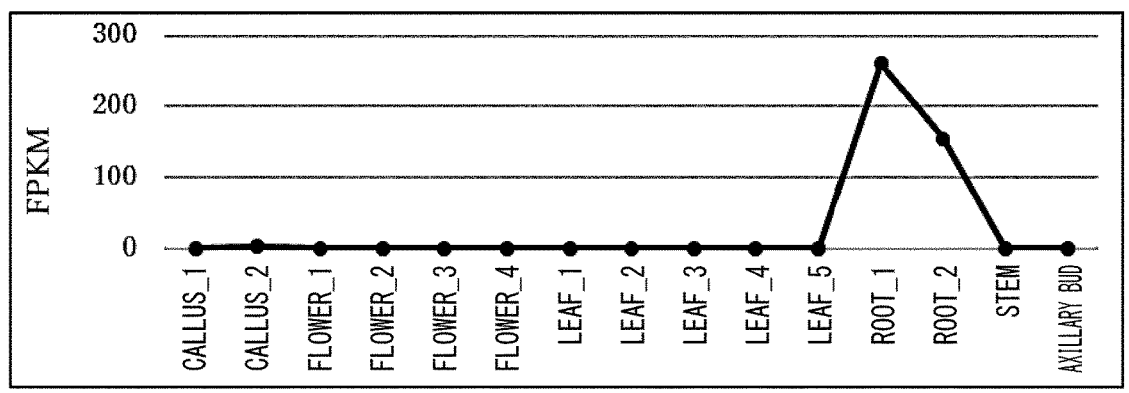
FIG. 3
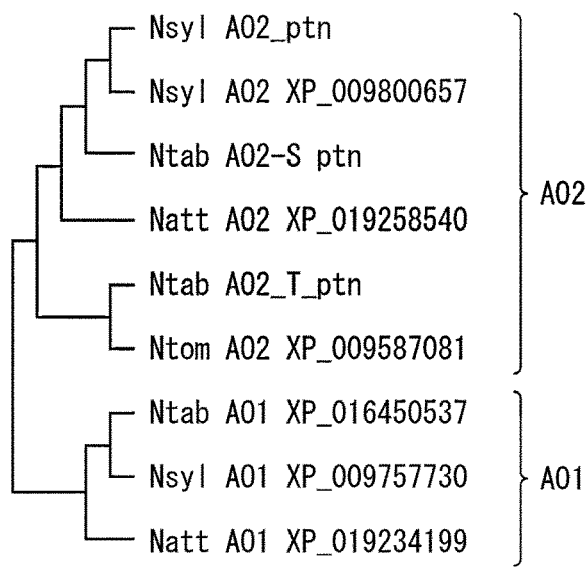

FIG. 4
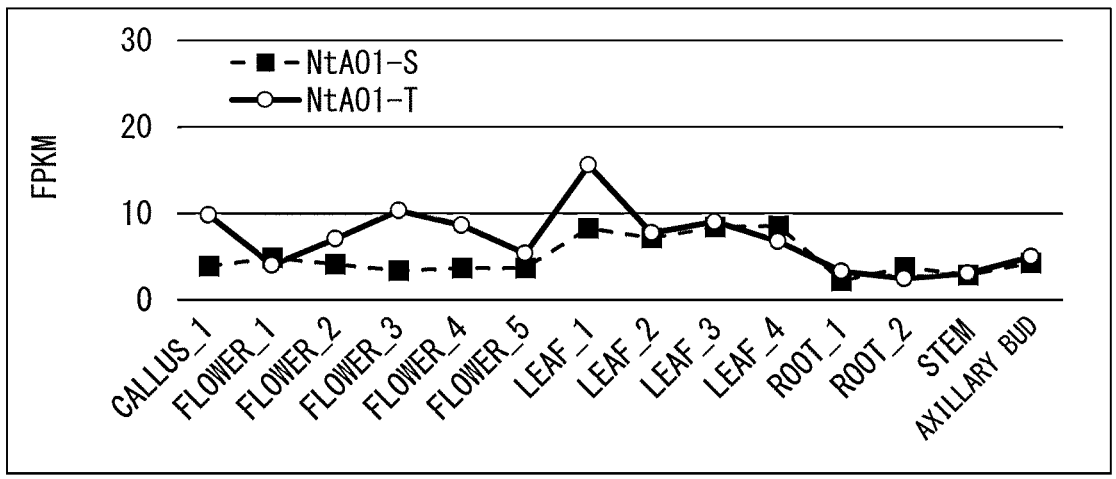
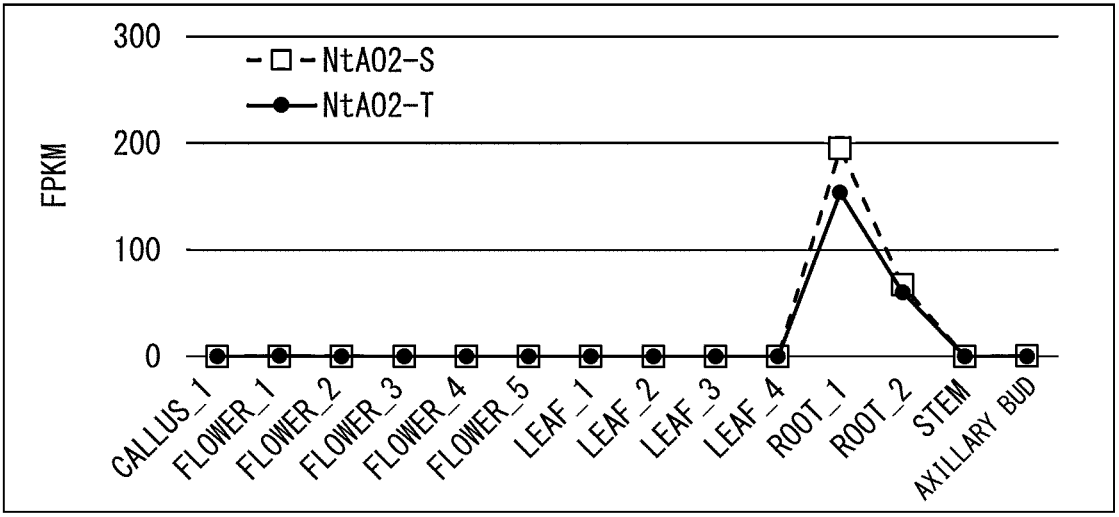

FIG. 7
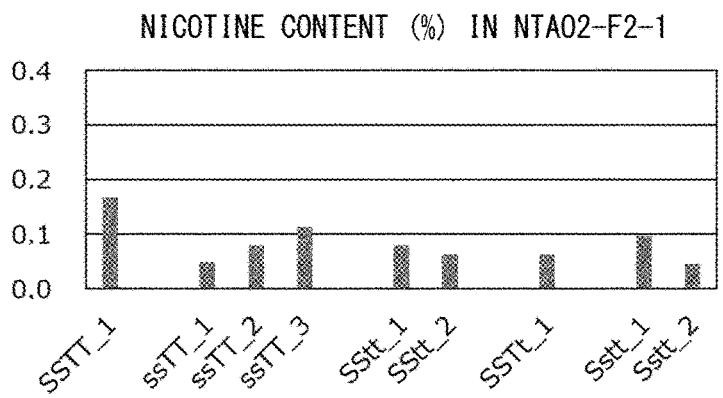
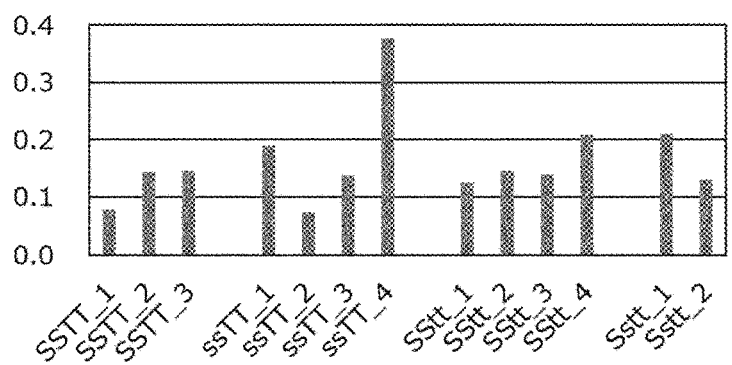
FIG. 8
(a)
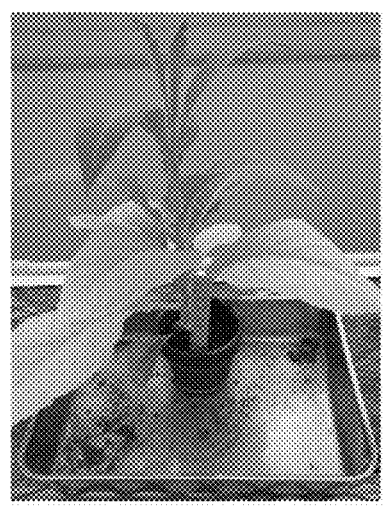
(b)

PLANT BODY OF GENUS *NICOTIANA* WITH LOW ALKALOID CONTENT AND PRODUCTION METHOD THEREOF

This application is a Continuation of PCT International Application No. PCT/JP2021/015920 filed in Japan on Apr. 19, 2021, which claims the benefit of Patent Application No. 2020-074233 filed in Japan on Apr. 17, 2020, the entire contents of which are hereby incorporated by reference.

REFERENCE TO AN ELECTRONIC SEQUENCE LISTING

The contents of the electronic sequence listing (1248-1893PUS1.xml; Size: 198,078 bytes; and Date of Creation: Nov. 29, 2022) is herein incorporated by reference in its entirety.

TECHNICAL FIELD

The present invention relates to a tobacco plant having a low alkaloid content, and a method for producing the tobacco plant.

BACKGROUND ART

Nic1 and Nic2 loci are conventionally known as loci that are spontaneously mutated and that cause a tobacco (*Nicotiana tabacum*) to be low alkaloid. Several genes (e.g., a transcription factor) involved in nicotine biosynthesis are present in each of both the loci. In an nic1 mutant and an nic2 mutant in each of which nicotine is reduced, there is a large deletion in a genome, and genes of the several genes (e.g., a transcription factor) are lost from the genome. In a case where both the loci have homozygous mutations, a nicotine content is approximately 10% (2 mg/g to 4.5 mg/g cured leaves) of the nicotine content (15 mg/g to 45 mg/g) of a common tobacco variety (Non-Patent Literature 1). There have been reported various studies to reduce an alkaloid content such as nicotine in a tobacco. For example, Non-Patent Literature 1 summarizes examples of production of a low nicotine tobacco by suppression of functions of genes of biosynthetic enzymes QPT, PMT, and BBL of nicotine. Nicotine contents in a tobacco in which the functions of these genes are suppressed are 1.4 mg/g cured leaves, 0.6 mg/g to 2.2 mg/g cured leaves, and 4.1 mg/g to 4.4 mg/g cured leaves, respectively. These genes include a gene (QPT) in which a malformation is caused by suppression of expression (Non-Patent Literature 2). In contrast, there are reports that a nicotine content in a tobacco in which a function of PMT is suppressed is reduced by 96.7% of the nicotine content of a control, i.e., decreased to 3.3% of the nicotine content of the control in the most effective line (Non-Patent Literature 3) and that a nicotine content in a knockout line of BBL is reduced to 0.3% of the nicotine content of a control (Non-Patent Literature 4). However, in these reports, though an effect of reducing nicotine is great, it is necessary to suppress functions of all five PMTs that are present in a tobacco genome, and it is also necessary to knock out all six BBLs that are present in a tobacco genome. This becomes a major barrier in actually carrying out breeding.

Non-Patent Literatures 5 and 6 report results of examination of various genes involved in biosynthesis of alkaloid in tobacco plants and expression of those genes. It has been suggested that two aspartate oxidase (AO) genes, which are AO1 and AO2, are present in the tobacco plants, that the AO1 is ubiquitously expressed throughout the plants, and that the AO2 is root-specifically expressed. AO is an enzyme that produces iminoaspartic acid by catalyzing oxidation of aspartic acid. AO is an important in vivo enzyme involved in metabolism of nicotinic acid and nicotinamide.

Patent Literature 1 discloses that an alkaloid content is reduced by down-regulation of nicotine biosynthetic enzyme genes (including an AO gene) in combination with an NBB1 or A622 gene. Patent Literature 2 discloses that nicotine alkaloid is reduced by decreasing expression of nicotine biosynthetic genes (including an AO gene) by a genome editing technique. However, in Patent Literatures 1 and 2, there are no experimental results in which the AO gene is actually treated, and AO1 and AO2 are not distinguished from each other.

Furthermore, it has been recently shown in a tobacco that an alkaloid content is decreased to 2% to 4% of the alkaloid content of a control in a knockout line of two genes ERF189 and ERF199, each of which is a transcription factor that positively regulates a nicotine biosynthetic enzyme gene group (Non-Patent Literature 7). In this line, an expression level of a large number of nicotine biosynthetic gene groups (e.g., PMT and AO2) that are under regulation by the ERF189 and the ERF199 is reduced to approximately to 3% of the expression level of a control (does not become 0 (zero)). However, knockout of a transcription factor affects transcription of various gene groups and suppresses functions of a large number of genes. This causes a fear of affecting a metabolism pathway of plants. It is actually suggested that a carbon (C)/nitrogen (N) ratio is unbalanced in this line.

In a plant that is different from a tobacco, it is known that disruption of a function of an AO gene may cause a living organism to be lethal (Non-Patent Literature 8).

Non-Patent Literature 9 discloses that an RNAi construct of a tobacco AO2 (described as AO1 in Non-Patent Literature 9) was introduced in a tobacco, and a nicotine content in an upper leaf at 2 weeks after topping was reduced to 0.5% or less to approximately 14% of the nicotine content of a control in a transformed tobacco in which a transcript amount of the AO2 was reduced. Non-Patent Literature 9 also discloses that an individual having a low nicotine content exhibits a phenotype of early senescence (produces white to reddish brown spots) in a fully expanded leaf and a lower leaf (mature leaf). *Nicotiana tabacum* is an amphidiploid plant the genome of which includes a genome derived from *Nicotiana sylvestris* (S) and a genome derived from *Nicotiana tomentosiformis* (T). In many cases, there are the following two types of genes of *Nicotiana tabacum*: a gene derived from an S genome; and a gene derived from a T genome. However, in Non-Patent Literature 9, no sequence of an AO2-T gene is disclosed, and AO2-S and AO2-T genes are not distinguished from each other. Furthermore, Non-Patent Literature 9 neither mentions any non-recombinant mutant nor has any Example of a tobacco plant that is different from *Nicotiana tabacum*.

CITATION LIST

Patent Literatures

[Patent Literature 1]
International Publication No. WO 2006/109197 (Publication Date: Oct. 19, 2006)
[Patent Literature 2]
International Publication No. WO 2018/222667 (Publication Date: Dec. 6, 2018)

Non-Patent Literatures

[Non-patent Literature 1]
Lewis, R. S. (2018) Potential Mandated Lowering of Nicotine Levels in Cigarettes: A Plant Perspective. Nicotine & Tobacco Research, 1-5
[Non-patent Literature 2]
Khan, S. et al. (2017) Cloning and functional characterization of quinolinic acid phosphoribosyl transferase (QPT) gene of Nicotiana tabacum, Physiol. Plant. 160: 253-265
[Non-patent Literature 3]
Wang et al. (2008) Generation of tobacco lines with widely different reduction in nicotine levels via RNA silencing approaches, J. Biosci. 33: 177-184
[Non-patent Literature 4]
Schachtsiek and Stehle (2019) Nicotine-free, nontransgenic tobacco (Nicotiana tabacum L.) edited by CRISPR-Cas9, Plant Biotechnol. J. 17: 2228-2230
[Non-patent Literature 5]
Kajikawa, M. et al. (2017) Genomic insights into the evolution of the nicotine biosynthesis pathway in tobacco, Plant physiology, 174: 999-1011
[Non-patent Literature 6]
Xu, S. et al. (2017) Wild tobacco genomes reveal the evolution of nicotine biosynthesis, Proc. Natl. Acad. Sci. USA 114: 6133-6138
[Non-patent Literature 7]
Hayashi, S. et al. (2020) Genetic manipulation of transcriptional regulators alters nicotine biosynthesis in tobacco, Plant Cell Physiol. pcaa036 (DOI: 10.1093/pcp/pcaa036)
[Non-patent Literature 8]
Katoh, A. et al. (2006) Early Steps in the Biosynthesis of NAD in Arabidopsis Start with Aspartate and Occur in the Plastid, Plant Physiology 141: 851-857
[Non-patent Literature 9]
Martinez et al. (2020) Genetic attenuation of alkaloids and nicotine content in tobacco (Nicotiana tabacum), Planta 251:92, doi.org/10.1007/s00425-020-03387-1

SUMMARY OF INVENTION

Technical Problem

A tobacco having a low alkaloid content has been conventionally known. However, mutation or suppressed expression of a large number of genes has been necessary for achievement of an extremely low nicotine content (e.g., 5% or less of the nicotine content of a wild type). Furthermore, as long as a function of a gene is suppressed, such a tobacco having a low alkaloid content may involve a problem of occurrence of undesired characters (e.g., problems such as malformation and early senescence). That is, there has not been any example in which a tobacco plant having an extremely low nicotine content is produced by mutation of as few as one or two enzyme genes.

An embodiment of the present invention has been made in view of the above problems, and a main object of an embodiment of the present invention is to provide a tobacco in which a function of a small number of (one or two) genes is suppressed by endogenous mutations in the genes and which has a low alkaloid content, and a method for producing the tobacco.

Solution to Problem

In order to attain the object, as a result of repeated diligent study, the inventors of the present application have discovered for the first time that a function of a gene encoding, in a tobacco plant, AO2, which is root-specific aspartate oxidase, is suppressed by a mutation that is inherent in an AO2 gene, so that an alkaloid content in the tobacco plant is decreased. That is, the inventors of the present application have completed the present invention by finding that a mutation of a single AO2 gene in a diploid tobacco plant (Nicotiana sylvestris) and a mutation of two AO2 genes (AO2-S and AO2-T genes) in an amphidiploid tobacco plant (Nicotiana tabacum) result in an extremely low alkaloid content (less than 5% of the alkaloid content of a control) and that a mutation of the AO2-S gene or the AO2-T gene, i.e., a mutation of a single AO2 gene in the amphidiploid tobacco plant (Nicotiana tabacum) causes a nicotine content to be half or less the nicotine content of the control.

That is, in a tobacco plant in accordance with an aspect of the present invention, a mutation that specifically causes suppression of a function of an endogenous gene is introduced in the endogenous gene in a genome, the endogenous gene being at least one of: (a) an endogenous gene which contains, as a coding region, a polynucleotide that encodes a polypeptide having a sequence identity of 95% or higher with an amino acid sequence represented by SEQ ID NO: 2 or SEQ ID NO: 5; and (b) an endogenous gene which contains, as a coding region, a polynucleotide that encodes a polypeptide having a sequence identity of 95% or higher with an amino acid sequence represented by SEQ ID NO: 6.

A method of producing a tobacco plant having a low alkaloid content in accordance with an aspect of the present invention includes the step of introducing a mutation in a genome of a tobacco plant, the mutation specifically causing suppression of a function of at least one of: (a) an endogenous gene which contains, as a coding region, a polynucleotide that encodes a polypeptide having a sequence identity of 95% or higher with an amino acid sequence represented by SEQ ID NO: 2 or SEQ ID NO: 5; and (b) an endogenous gene which contains, as a coding region, a polynucleotide that encodes a polypeptide having a sequence identity of 95% or higher with an amino acid sequence represented by SEQ ID NO: 6, the step of introducing the mutation including introducing the mutation in the at least one of the endogenous genes.

Advantageous Effects of Invention

The present invention makes it possible to provide a tobacco having a lower alkaloid content.

BRIEF DESCRIPTION OF DRAWINGS

FIG. 2 is a diagram showing expression profiles of two AO genes (NsAO1 and NsAO2) of Nicotiana sylvestris (N. sylvestris) (RNA-seq data, unit: fragments per kilobase of exon per million mapped reads (FPKM)).

FIG. 3 is a diagram showing a molecular phylogenetic tree of amino acid sequences of Nicotiana AOs. Clustering is carried out by a UPGMA method. Nsyl AO2_ptn, Ntab AO2-S_ptn, and Ntab AO2_T_ptn indicate amino acid sequences that are translated from respective NsAO2, NtAO2-S, and NtAO2-T genes each of which is identified in the present invention. Nsyl indicates Nicotiana sylvestris (N. sylvestris), Ntab indicates Nicotiana tabacum (N. tabacum), Ntom indicates Nicotiana tomentosiformis (N. tomentosifor-

*mis*), and Natt indicates *Nicotiana attenuata* (*N. attenuata*). The number beginning with XP is the GenBank accession number.

FIG. 4 is a diagram showing expression profiles of AO genes NtAO2-S, NtAO2-T, NtAO1-S, and NtAO1-T of *Nicotiana tabacum* (*N. tabacum*) (RNA-seq data, unit: fragments per kilobase of exon per million mapped reads (FPKM)).

Figure 5:
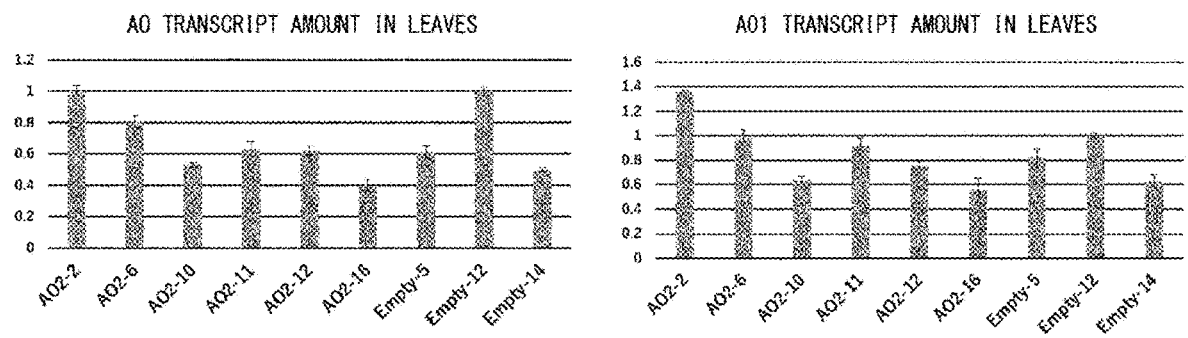

FIG. 5 is a diagram showing transcript amounts in roots and leaves of AO1, AO2, or AOs (both the AO1 and the AO2).

Figure 6:
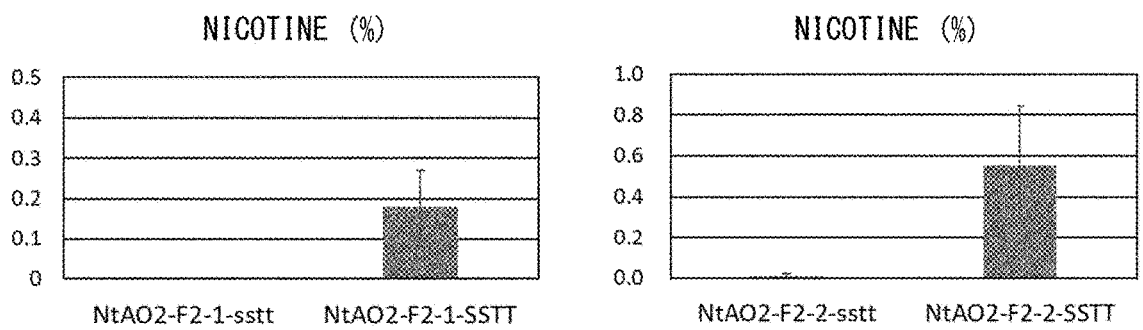

FIG. 6 is a diagram showing a nicotine content in a tobacco plant in which a function of an AO2 gene is suppressed.

FIG. 7 is a diagram showing a nicotine content in a tobacco plant in which a function of an AO1 gene is suppressed.

FIG. 8 is a view illustrating states of leaves ((a) NtAO1-ssTT and (b) NtAO1-SSTT) of a tobacco plant in which the function of the AO1 gene is suppressed.

DESCRIPTION OF EMBODIMENTS

[1. Tobacco Plant]

An embodiment of the present invention provides a tobacco plant in which a mutation that specifically causes suppression of a function of an endogenous gene is introduced in the endogenous gene in a genome, the endogenous gene being at least one of: (a) an endogenous gene which contains, as a coding region, a polynucleotide that encodes a polypeptide having a sequence identity of 95% or higher with an amino acid sequence represented by SEQ ID NO: 2 or SEQ ID NO: 5; and (b) an endogenous gene which contains, as a coding region, a polynucleotide that encodes a polypeptide having a sequence identity of 95% or higher with an amino acid sequence represented by SEQ ID NO: 6.

The expression "polypeptide having a sequence identity of 95% or higher with an amino acid sequence represented by [ . . . ]", which specifies a polypeptide with use of one of amino acid sequences listed in a sequence listing, herein means a wild-type polypeptide. The wild-type polypeptide means a polypeptide which is typically present in a tobacco plant (described later). The wild-type polypeptide is, for example, a protein which has the amino acid sequence represented by SEQ ID NO: 2, 5, or 6 or an orthologue, in the tobacco plant, of the protein. The terms "polypeptide" and "protein" herein have substantially the same meaning, and can therefore be used interchangeably. Thus, a region that is present in the endogenous gene and that encodes a polypeptide is herein described as a coding region (CDS).

The embodiment can satisfy one or more or all of the following conditions. In the endogenous gene of (a), the mutation causing the suppression of the function of the endogenous gene of (a) is present. In the endogenous gene of (a), the mutation causing the suppression of the function of the endogenous gene of (b) is absent. In the endogenous gene of (b), the mutation causing the suppression of the function of the endogenous gene of (b) is present. In the endogenous gene of (b), the mutation causing the suppression of the function of the endogenous gene of (a) is absent.

The term "tobacco plant" as used herein encompasses (i) individuals as a whole (such as a mature plant, a seedling, and a seed), (ii) tissues (such as a leaf, a stem, a flower, a root, a reproductive organ, an embryo, and a part of any of these), and (iii) cured products of any of these.

The tobacco plant is not particularly limited, provided that the tobacco plant is a plant belonging to the genus *Nicotiana*. Examples of the tobacco plant encompass *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosiformis, Nicotiana trigonophylla, Nicotiana umbratica, Nicotiana undulata, Nicotiana velutina, Nicotiana wigandioides*, and hybrids of tobacco plants. Among these tobacco plants, *Nicotiana tabacum* and *Nicotiana rustica*, each of which is used as a material to produce a tobacco leaf, are particularly preferable. *Nicotiana sylvestris* can also be preferably used.

The tobacco plant in accordance with an embodiment of the present invention has a lower alkaloid content than a wild-type tobacco plant. In a specific embodiment, the "wild-type tobacco plant" is a tobacco plant in which an AO2 gene that is present in a genome thereof is in normal function. In the specific embodiment, the "wild-type tobacco plant" is preferably a tobacco plant in which the AO2 gene and an AO1 gene that are present in the genome thereof are in normal function. The expression "the AO2 gene (and the AO1 gene) is/are in normal function" means that a factor which suppresses expression of the AO2 gene (and the AO1 gene) has not been introduced into the genome and that the AO2 gene (and the AO1 gene) is/are not mutated. In the specific embodiment, the "wild-type tobacco plant" is, for example, *Nicotiana sylvestris* including, in the genome, a polynucleotide 1 as part of the AO2 gene (a coding region), or *Nicotiana tabacum* including, in the genome, each of a polynucleotide 2a and a polynucleotide 2b as part of the AO2 gene. The *Nicotiana sylvestris* preferably includes, in the genome, a polynucleotide 3 as part of the AO1 gene. The *Nicotiana tabacum* preferably includes, in the genome, each of a polynucleotide 4a and a polynucleotide 4b as part of the AO1 gene.

Polynucleotide 1: encoding a polypeptide having an amino acid sequence represented by SEQ ID NO: 2
Polynucleotide 2a: encoding a polypeptide having an amino acid sequence represented by SEQ ID NO: 5
Polynucleotide 2b: encoding a polypeptide having an amino acid sequence represented by SEQ ID NO: 6
Polynucleotide 3: encoding a polypeptide having an amino acid sequence represented by SEQ ID NO: 62
Polynucleotide 4a: encoding a polypeptide having an amino acid sequence represented by SEQ ID NO: 63
Polynucleotide 4b: encoding a polypeptide having an amino acid sequence represented by SEQ ID NO: 64

The term "alkaloid" refers to a basic organic compound that commonly contains a nitrogen atom. In order to attain the object of the present invention, alkaloid, which refers to alkaloid that is produced in a tobacco plant, specifically includes nicotine, nornicotine, anatabine, anabasine, and myosmine. In *Nicotiana tabacum*, nicotine is accumulated as main alkaloid. In contrast, for some *Nicotiana tabacum* and *Nicotiana sylvestris*, nicotine is accumulated during growth, but nicotine is converted to nornicotine during senescence or curing of a leaf. Alkaloid herein may refer to nicotine and nornicotine, each of which is the main alkaloid. The term "alkaloid content" refers to a content of alkaloid in a tobacco plant. The alkaloid content is commonly expressed by weight % relative to a cured leaf. The expression "low alkaloid content" means an alkaloid content that has been decreased as compared with an alkaloid content in a wild-type tobacco plant. The low alkaloid content or the decreased alkaloid content is, for example, 50% or less, 40% or less, 30% or less, 20% or less, 10% or less, 9% or less, 8% or less, 7% or less, 6% or less, preferably 5% or less, 4% or less, more preferably 3% or less, 2% or less, 1% or less, 0.8% or less, 0.6% or less, 0.4% or less, 0.2% or less, or 0.1% or less of the alkaloid content in the wild-type tobacco plant. The low alkaloid content or the decreased alkaloid content is, for example, 2.5% or less, 2% or less, 1.5% or less, 1% or less, preferably 0.5% or less, 0.4% or less, 0.3% or less, 0.2% or less, 0.1% or less, 0.08% or less, 0.06% or less, 0.04% or less, 0.02% or less, or 0.01% of a cured leaf weight of the tobacco plant.

Among alkaloids, nornicotine can be conveniently measured by, for example, spraying, on filter paper blotted with a leaf extract, an Isatin solution containing 2,3-indolinedione, and then heating a resulting filter. Alternatively, individual alkaloids can be quantitatively determined by, for example, gas chromatography-mass spectrometry (GC-MS) analysis.

It is known that two aspartate oxidase (AO) genes, which are AO1 and AO2, may be present in a tobacco plant. Among these AO genes, it has been made clear that the AO2 is root-specifically expressed, and it has been suggested that the AO2 is involved in nicotine biosynthesis (Xu, S. et al. (2017) Proc. Natl. Acad. Sci. USA 114: 6133-6138; Kajikawa, M. et al. (2017) Plant physiology, 174: 999-1011). In contrast, the AO1 is constitutively expressed in the entire plant.

The term "aspartate oxidase" as used herein (herein also referred to as "AO") refers to an enzyme that has activity to oxidize asparatic acid so as to produce iminoaspartic acid. Such activity of the enzyme can be measured by a publicly-known method (Hao et al. (2008) Plant Science 271: 133-142). It is known that AO is an important in vivo enzyme involved in metabolism of nicotinic acid and nicotine amide and that AO shows embryo lethality in response to disruption of an AO gene in *Arabidopsis thaliana* (Katoh, A. et al. (2006) Plant Physiology 141: 851-857).

A tobacco plant in accordance with the present embodiment has been achieved on the basis of knowledge by the inventors of the present invention that suppression of a function of the AO2 gene decreases a content of alkaloid including nicotine and nornicotine. As described above, suppression of a function of the AO gene may cause various abnormalities or lethality to a plant. Thus, an influence of mutation of the AO gene on production of alkaloid such as nicotine has not been previously studied.

The expression "suppression of a function of an endogenous gene" as used herein means a state in which a gene that is present in a genome does not fulfill its original function. Therefore, the expression "suppression of a function of an endogenous gene" encompasses (i) "a mutation of an endogenous gene", (ii) "disruption of an endogenous gene", and (iii) "suppression of expression of an endogenous gene" by a gene (including an exogenous gene) other than the endogenous gene. In addition, specifically causing suppression of a function refers to suppression of only a function of a target gene without suppressing a function of a gene different from the target gene. For example, it is desirable to avoid causing suppression of the function of the AO1 gene or causing dysbolism by suppression of a function of a plurality of genes that are under regulation by a single transcription factor.

As described below, *Nicotiana tabacum* is an amphidiploid and has a genome derived from its parent plant *Nicotiana sylvestris* (also referred to as an "S genome") and a genome derived from *Nicotiana tomentosiformis* (also referred to as a "T genome"). In a case where the tobacco plant is *Nicotiana tabacum*, an alkaloid content is decreased by specifically suppressing a function of an aspartate oxidase gene in only one of the S genome and the T genome. Thus, a function of aspartate oxidase genes in both the S genome and the T genome may be specifically suppressed, or a function of an aspartate oxidase gene in one of the S genome and the T genome may be specifically suppressed. In this case, specific suppression of a function refers to suppression of only a function of an aspartate oxidase gene in one of the S genome and the T genome without suppressing a function of an aspartate oxidase gene in the other of the S genome and the T genome. In order to specifically suppress a function of only one AO2 gene that is present in the S genome or the T genome, it is preferable to introduce, in the only one AO2 gene, a change in nucleotide sequence.

The "mutation of an endogenous gene" means, for example, (i) a mutation of a gene (i.e., decrease or impairment of a function) such that an original functional polypeptide is not produced, (ii) a mutation of a gene such that although a functional polypeptide is produced, the amount of the functional polypeptide produced is decreased, or (iii) a mutation of a gene such that although a functional polypeptide is produced, the stability of the functional polypeptide is decreased. The "disruption of an endogenous gene" means that (i) a gene which is originally present in a genome is not present in the genome or (ii) a transcription product is not produced from a gene which is present in a genome. The "suppression of expression of an endogenous gene" means, for example, a state in which although no change has occurred to a nucleotide of an endogenous gene, the transcriptional or translational function of the gene (from transcription into mRNA to subsequent translation into a polypeptide) is modified through another factor so that (i) the amount of the polypeptide produced is decreased or (ii) no polypeptide is produced. The "suppression of expression of an endogenous gene" can occur as a result of, for example, degradation of mRNA which is transcribed from the endogenous gene.

As used herein, the "mutation" has the meaning ordinarily understood in the technical field to which the present application belongs, and means, for example, any change in a nucleotide present in a wild-type genome or any change in an amino acid residue present in a wild-type polypeptide (examples of these changes encompass substitution, deletion, insertion, addition, duplication, inversion, and translocation). Therefore, the "mutation of an endogenous gene" means, for example, (i) a mutation of a gene such that an original functional polypeptide is not produced (including a mutation such that a polypeptide the function of which is decreased or impaired is produced), (ii) a mutation of a gene such that although a polypeptide is produced, the amount of the polypeptide produced is decreased, (iii) a mutation of a gene such that although a polypeptide is produced, the stability of the polypeptide is decreased, or (iv) a mutation of a gene such that the gene (a coding region or a genomic DNA sequence including an untranslated region) is lost or that transcription from the gene is suppressed (e.g., a transcription-regulating region or a transcription-initiating region is deleted).

In a case where a function is impaired by substitution, the substitution can be present in at least one of the following: a promoter sequence (a sequence upstream (5' end) of a coding region) and a terminator sequence (a sequence downstream (3' end) of the coding region); a 5' untranslated region and a 3' untranslated region; conserved sequences (such as GT at the 5' end and AG at the 3' end) present at both ends of an intron; and the coding region.

For example, substitution in a nucleotide sequence which is present in a promoter sequence, a 5' untranslated region, or a 3' untranslated region of a gene and which is important in regulating expression of the gene leads to a decrease in the transcriptional activity of the gene or to a decrease in the stability of a transcription product produced from the gene. Any of these decreases can lead to a reduction in transcription product produced from the gene, and ultimately lead to a reduction in translation product. Substitution in a conserved sequence present in an intron (splicing mutation) leads to splicing abnormality of mRNA. This results in abnormal mRNA in which an unnecessary intron is added or inserted. The abnormal mRNA generates an abnormal translation product or translation thereof does not terminate, due to, for example, frame shifting.

In a case where a nucleotide substitution present in a coding region is a missense mutation (an amount of a wild-type polypeptide is decreased), the substitution leads to production of an amino acid different from an original amino acid. This results in a polypeptide the original function of which is decreased or impaired.

Substitution in a coding region can lead to production of a translation product which has an incomplete length or a translation product which does not maintain an original function. The translation product which has an incomplete length is derived from conversion, by the substitution, of a codon which encodes an amino acid into a stop codon (i.e., nonsense mutation). As compared with an original translation product, the translation product which has an incomplete length is such that one or more consecutive amino acid residues including an amino acid residue at a C-terminus are deleted. The nonsense mutation occurs to any codon present upstream of an original stop codon, and is preferably present upstream of the original stop codon with one or more codons therebetween. Thus, a translation product produced from a gene which has a nonsense mutation has an incomplete length. The translation product which does not maintain an original function is produced due to amino acid substitution. In this case, the amount of a transcription product may be equal to that of a transcription product in a wild-type plant. The translation product has, therein, a change in tertiary structure, a decrease in function as a functional domain, or the like. A preferred aspect of the mutation of the present invention is such amino acid substitution that leads to production of a translation product which does not maintain an original function. The amino acid substitution is preferably non-conservative substitution with a high possibility of changing the function of the translation product. Examples of the non-conservative substitution encompass (i) substitution of an amino acid by another amino acid having a different electric charge or different hydrophobicity (e.g., substitution of a basic amino acid by an acidic amino acid, substitution of a basic amino acid or an acidic amino acid by a neutral amino acid, substitution of a neutral amino acid by a basic amino acid or an acidic amino acid, and substitution of a polar amino acid by a non-polar amino acid) and (ii) substitution of an amino acid by another amino acid having a side chain of a different bulk (three-dimensional size).

As another example of a phenomenon caused by a nonsense mutation, in a case where a protein coding region of an AO2 gene has a nonsense mutation, nonsense-mediated mRNA decay (Brogna and Wen (2009) Nat. Structural Mol. Biol. 16: 107-113) can occur. The nonsense-mediated mRNA decay leads to degradation of a transcription product. Thus, the nonsense mutation may lead to a decrease in the amount of the transcription product. It is preferable that at least one exon which has the nonsense mutation be present in the AO2 gene, and it is particularly preferable that the exon which has the nonsense mutation be not, among the plurality of exons of which the AO2 gene is composed, an exon which is present most downstream (3' end), in order to cause the nonsense-mediated mRNA decay. An AO2 gene of a wild-type tobacco plant consists of seven exons and six introns. Thus, a preferred embodiment of the nonsense mutation which leads to the nonsense-mediated mRNA decay is such that at least one nonsense mutation is present in the first exon to the sixth exon of the AO2 gene.

In a case where a mutation(s) (deletion, insertion, and/or the like) other than substitution occur(s) in a promoter sequence, a 5' untranslated region, and/or a 3' untranslated region, a decrease can occur in transcriptional activity or stability as in the case of the substitution, so that (i) the amount of a transcription product can decrease and (ii) the amount of a polypeptide can decrease. In addition, a mutation, other than substitution, in a conserved sequence present in an intron can lead to translation into a polypeptide having an amino acid sequence different from an original amino acid sequence, as in the case of the substitution. A mutation, other than substitution, in a coding region can lead to translation into a polypeptide having an amino acid sequence different from an original amino acid sequence, due to (i) deletion or insertion of an amino acid residue (caused by deletion or insertion of consecutive nucleotides which are multiples of 3) or (ii) frame shifting. Large deletion of an entire gene or insertion of a large fragment into the gene can cause expression itself of the gene to be lost.

In the tobacco plant, the mutation or the disruption of the at least one of the endogenous genes occurs as a result of, for example, a spontaneous mutation, a mutagen treatment, genetic modification, genome editing, or gene knockout. The spontaneous mutation of the at least one of the endogenous genes generally occurs due to (i) a replication error and (ii) damage to the at least one of the endogenous genes. The cause of the damage is, for example, exposure to a publicly-known naturally-occurring mutagen (e.g., radiation or ultraviolet rays). The mutagen treatment with respect to the at least one of the endogenous genes can be carried out by artificially causing a mutagen to act on the tobacco plant (as necessary, in combination with suppression of a gene repair function). Examples of the type of the mutagen encompass chemical agents such as ethyl methane sulfonate (EMS), sodium azide, ethidium bromide, and nitrous acid. Note, however, that the mutagen is not limited to these chemical agents, provided that the mutagen is a chemical agent which causes the mutation in a genomic DNA of a tobacco plant. Examples of the mutagen also encompass γ rays, heavy ion beams, X-rays, neutron rays, and UV rays. Note, however, that the mutagen is not limited to these beams and rays, provided that the mutagen is a radiation or the like which causes the mutation in a genomic DNA of a tobacco plant. The mutagen is preferably EMS. These methods are preferable from the viewpoint that an exogenous factor need not be added to a target plant. Modification of the at least one of the endogenous genes can be carried out by homologously modifying part or the whole of a target gene with use of a modifying sequence according to a publicly-known genetic modification method. The genome editing of the at least one of the endogenous genes can be carried out by a publicly-known technique (for example, zinc-finger nucleases (ZFN), transcription activator-like effector nucleases (TALEN), and a CRISPR/Cas9 system). The gene knockout can be carried out by, for example, insertion of a publicly-known transposon (mobile genetic factor) or T-DNA.

In the case of the CRISPR/Cas9 system, genome editing can be carried out, if a guide RNA and a Cas9 protein are present in a target cell. In the case of TALEN and ZFN, the genome editing can be carried out, if a fusion protein (in which a DNA-binding domain and a nuclease are fused) is present in the target cell. Therefore, (i) the guide RNA and the Cas9 protein and (ii) the fusion protein can be each directly introduced into the target cell. Examples of a method of directly introducing any of these into the target cell encompass a PEG method, an electroporation method, and a particle bombardment method. Alternatively, a vector in which a construct (including (i) the guide RNA and a polynucleotide which encodes the Cas9 protein and (ii) any promoter and/or any terminator) is inserted may be introduced into the target cell and a tissue via, for example, *Agrobacterium*.

In the case of the CRISPR/Cas9 system, a sequence which is complementary to a nucleotide sequence present immediately upstream of XGG in a genome forms a base pair with a part of the guide RNA, and a double-stranded genomic DNA is cleaved by Cas9.

In the case of TALEN, a pair of DNA-binding domains in artificial nucleases forming a dimer each bind to a corresponding one of nucleotide sequences such that each of the nucleotide sequences is present at a terminus of a corresponding one of FokI cleavage domains so as to be away from the terminus by a spacer of 5 to 20 bases. One of the nucleotide sequences is present at one of strands of double-stranded genomic DNA, and the other of the nucleotide sequences is present at the other of the strands of the double-stranded genomic DNA. Therefore, one of the pair of DNA-binding domains binds to one of the strands, and the other of the pair of DNA-binding domains binds to the other of the strands. Each of the DNA-binding domains is composed of repeating units (modules) each of which is composed of 33 to 34 amino acid residues.

In the case of ZFN, as in the case of TALEN, a pair of DNA-binding domains in artificial nucleases forming a dimer each bind to a corresponding one of nucleotide sequences such that each of the nucleotide sequences is present at a terminus of a corresponding one of FokI cleavage domains so as to be away from the terminus by a spacer of 5 to 20 bases. Each of the DNA-binding domains is composed of a plurality of zinc finger modules.

In an embodiment, a substitution of a nucleotide in the AO2 gene by EMS treatment results in, for example, (I) a frame-shift mutation, (II) a truncation mutation (essential deletion of an N-terminus amino acid residue), (III) a splicing mutation, or (IV) a nonsense mutation. This is because the EMS treatment tends to produce a specific nucleotide change (a C-to-T substitution and a G-to-A substitution) in DNA.

The above (I) and (II) occur as a result of, for example, a G-to-A substitution of an initiation codon ATG encoding a first methionine (disappearance of the initiation codon). The G-to-A substitution may occur, for example, at position 3003 in SEQ ID NOs: 35 to 37 (bases at position 3003 in nucleotides represented by SEQ ID NOs: 35 to 37 are each G). Disappearance of the initiation codon causes the above (I) in a case where there is an ATG starting at position 3n+0 or 2 (n is an integer) of a corresponding coding region. Disappearance of the initiation codon causes the above (II) in a case where there is an ATG starting at position 3n+1 (n is an integer) of a corresponding coding region.

The above (III) occurs in, for example, the AO2 gene in which the G-to-A substitution occurs at any one of the following positions: position 3135, position 3477, position 3842, position 3933, position 4177, position 4266, position 4324, position 4408, position 4490, position 4778, position 4841, and position 5069 in SEQ ID NO: 35; position 3135, position 3478, position 3843, position 3934, position 4178, position 4267, position 4325, position 4409, position 4491, position 4779, position 4842, and position 5071 in SEQ ID NO: 36; and position 3135, position 3278, position 3643, position 3733, position 3977, position 4078, position 4136, position 4236, position 4318, position 4747, position 4810, and position 5032 in SEQ ID NO: 37 (each of which is the above-described conserved sequence present in an intron).

The above (IV) occurs in, for example, in the AO2 gene in which the C-to-T substitution or the G-to-A substitution occurs at one or more positions shown in (IVa) to (IVf) below. This is because only CAA, CAG, CGA, and TGG that are present in-frame in SEQ ID NOs: 35 to 37 may change to stop codons (TAA, TAG, and TGA) by the EMS treatment. In the following illustration, "C" represents a nucleotide to be substituted (i.e., the C-to-T substitution), and "G" represents a nucleotide to be substituted (i.e., the G-to-A substitution).

(IVa) and (IVb) in SEQ ID NO: 35:
(IVa) C at position 3031, C at position 3118, C at position 3124, G at position 3134, G at position 3478, G at position 3486, G at position 3487, C at position 3503, C at position 3527, C at position 3533, G at position 3552, G at position 3553, C at position 3563, C at position 3584, C at position 3587, C at position 3653, C at position 3737, C at position 3791, C at position 4051, C at position 4141, C at position 4174, C at position 4812, C at position 4818, C at position 5077, C at position 5275, C at position 5398, C at position 5401, C at position 5479, C at position 5533, C at position 5575, C at position 5587, G at position 5642, G at position 5643, G at position 5645, G at position 5646, C at position 5731, G at position 5744, G at position 5745, G at position 5822, G at position 5823, C at position 5839, G at position 5849, G at position 5850, C at position 5935, and C at position 5938, and
(IVb) C at position 6022, C at position 6025, G at position 6038, G at position 6039, C at position 6049, and C at position 6061;

(IVc) and (IVd) in SEQ ID NO: 36:
(IVc) C at position 3031, C at position 3118, C at position 3124, G at position 3134, G at position 3479, G at position 3487, G at position 3488, C at position 3504, C at position 3528, C at position 3534, G at position 3553, G at position 3554, C at position 3564, C at position 3585, C at position 3588, C at position 3654, C at position 3738, C at position 3792, C at position 4052, C at position 4142, C at position 4175, C at position 4813, C at position 4819, C at position 5079, C at position 5277, C at position 5400, C at position 5403, C at position 5481, C at position 5535, C at position 5577, C at position 5589, G at position 5644, G at position 5645, G at position 5647, G at position 5648, C at position 5733, G at position 5746, G at position 5747, G at position 5824, G at position 5825, C at position 5841, G at position 5851, G at position 5852, C at position 5937, and C at position 5940, and (IVd) C at position 6024, C at position 6027, G at position 6040, G at position 6041, C at position 6051, and C at position (51)6063; and (IVe) and (IVf) in SEQ ID NO: 37:
(IVe) C at position 3031, C at position 3118, C at position 3124, G at position 3134, G at position 3279, G at position 3287, G at position 3288, C at position 3304, C at position 3334, G at position 3353, G at position 3354, C at position 3364, C at position 3385, C at position 3388, C at position 3454, C at position 3538, C at position 3592, C at position 3851, C at position 3941, C at position 3974, C at position 4781, C at position 4787, C at position 5040, C at position 5238, C at position 5361, C at position 5364, C at position 5442, C at position 5496, C at position 5538, C at position 5550, G at position 5605, G at position 5606, G at position 5608, G at position 5609, C at position 5694, G at position 5707, G at position 5708, G at position 5785, G at position 5786, C at position 5802, G at position 5812, G at position 5813, and C at position 5898, and (IVf) C at position 5985, C at position 5988, G at position 6001, G at position 6002, C at position 6012, and C at position 6024.

In a preferred embodiment, the above (IV) occurs in one or more of the positions shown in (IVa), (IVc), and (IVe).

In a specific embodiment, the above (IV) occurs in one or more of the positions shown in (IVa) and (IVb). In a specific embodiment, the above (IV) preferably occurs in one or more of the positions shown in (IVa).

In another specific embodiment, the above (IV) occurs in one or more of the positions shown in (IVc) and (IVd). In the another specific embodiment, the above (IV) preferably occurs in one or more of the positions shown in (IVc).

In a further specific embodiment, the above (IV) occurs in one or more of the positions shown in (IVe) and (IVf). In the further specific embodiment, the above (IV) preferably occurs in one or more of the positions shown in (IVe).

Alternatively, the mutation can be one or more of the following mutations that are present in a coding region of the AO2 gene in a genome of a wild-type tobacco plant.
(1) a C-to-T substitution in a codon CAA, (2) a C-to-T substitution in a codon CAG, (3) a C-to-T substitution in a codon CGA, (4) one or two G-to-A substitutions in a codon TGG, and (5) a G-to-A substitution in a translation initiation codon ATG.

The above coding region is a region encoding an AO2 protein having a sequence identity of 95% or higher with an amino acid sequence represented by SEQ ID NO: 2, SEQ ID NO: 5, or SEQ ID NO: 6. The above AO2 protein has aspartate oxidase activity.

The above-described various mutations can be easily introduced into a tobacco plant by a person skilled in the art. Specifically, on the basis of these pieces of sequence information, a region which is present in a genome of any of various tobacco plants encompassed in the scope of the present invention and in which a mutation should be introduced can be determined as appropriate.

The mutation or disruption of the at least one of the endogenous genes can be determined by identifying the presence/absence of the mutation in the at least one of the endogenous genes. A method of identifying the mutation in the at least one of the endogenous genes only needs to allow the determination of the presence/absence of the mutation. Examples of the method encompass (1) a method in which a DNA sequence having the mutation is amplified by PCR or the like, and then a DNA nucleotide sequence is directly decoded with use of a commercially available sequencer or the like, (2) a method in which a difference in sequence is detected by a difference in distance of electrophoresis by a single strand conformation polymorphism (SSCP) method, (3) a method in which single nucleotide polymorphism (SNP) is detected by a CycleavePCR method, (4) a method in which the presence/absence of the mutation is identified by cleaving a mismatch site(s) with use of T7 Endonuclease1 or the like, (5) a cleaved amplified polymorphic sequence (CAPS) method in which the presence/absence of the mutation can be determined by the presence/absence of cleavage by a restriction enzyme treatment, (6) a derived CAPS (dCAPS) method in which a set of primers including a mismatch intentionally is used so that the presence/absence of the mutation can be determined by the presence/absence of cleavage by restriction enzymes, (7) a method (e.g., a PCR method in which a TaqMan probe is used) in which the presence/absence of the mutation is determined by identifying, with use of a probe which specifically hybridizes to a mutant sequence, whether or not the probe is hybridized, (8) a method (MassARRAY analysis) in which a primer that is adjacent to the mutation is used to carry out single nucleotide extension so as to detect the presence/absence of the mutation by a difference in mass between nucleotides taken in, and (9) a method in which, in a case where the mutation is deletion or insertion, the mutation is identified by a difference in mobility of electrophoresis. Alternatively, the mutation or disruption in the at least one of the endogenous genes can be determined by comparing (i) the size or the expression level of a protein which results from modification of the at least one of the endogenous genes with (ii) that of a wild-type protein. Specifically, such a comparison can be made by carrying out, for example, a Western blotting method.

Alternatively, the mutation or disruption can be analyzed by a "MutMap method". The MutMap method is a method in which bulked segregant analysis (BSA) is combined with whole genome sequencing (WGS) to identify a causative gene region of a mutant (Abe, A. et al., Nat. Biotechnol., 30(2): 174-178 (2012)). As compared with map-based cloning that is conventionally carried out, the MutMap method neither requires marker production nor requires use of a lot of individuals. This makes it possible to greatly reduce labor and time and enables more rapid gene identification.

In the MutMap method, first, a mutant line (>M2) having a desired character is crossed with a parent variety (original line) used for a mutagen treatment, so that an F1 generation is obtained, and an F1 individual is further selfed, so that an F2 generation is obtained. It is considered that a character obtained by a mutation is recessive in many cases. Thus, a phenotype of the F1 generation is supposed to be a wild type, and a phenotype of the F2 generation is supposed to be separated into a wild type and a mutant type at a ratio of 3:1.

In the F2 generation, genetic recombination results in a random combination of a wild-type genome and a genome containing a mutation derived from a mutant, so that genomes that are uniquely combined for each individual occur. Thus, in a case where genomic DNAs derived from an F2 individual showing a mutation-type phenotype are mixed (bulked) and subjected to WGS, an expected value of an appearance frequency of reads having mutations is 0.5 for most regions of a chromosome, whereas an appearance frequency of reads having (i) a mutation causative of a phenotype shown in a mutant and (ii) a mutation in a region around the mutation (i) is 1. In the MutMap method, the appearance frequency of the reads having such mutations is set as an "SNP-index", and it is determined that a causative gene (or factor) is present in a region in which SNP-index=1 is continuous.

Note that the MutMap method has been used mainly for gene analysis of rice having a relatively small genome size. The present invention has shown that the MutMap method is also applicable to gene analysis of an organism having a relatively large genome size, such as a tobacco plant.

An individual, which is generated as a result of a mutation or disruption of at least one of the endogenous genes, is herein referred to as a mutant of a tobacco plant (hereinafter simply referred to as "mutant"). Among tobacco plants, *Nicotiana tabacum* is an amphidiploid and has both a genome derived from its parent plant *Nicotiana sylvestris* (also referred to as an "S genome") and a genome derived from *Nicotiana tomentosiformis* (also referred to as a "T genome"). In *Nicotiana tabacum*, in most cases, genes indicated by an identical name are present in each of an S genome and a T genome. In the case of *Nicotiana tabacum*, the mutant can have the mutation in either the S genome or the T genome. The mutant may alternatively have the mutation in both the S genome and the T genome. Note that a single gene may have a single mutation or a plurality of mutations for causing impairment of a function. Note also that the type(s) of the mutation(s) is/are not limited. In the case of *Nicotiana tabacum*, any or all of four alleles in total, two of which are present in each of the S genome and the T genome, may have a mutation(s). In a case where mutations are present in a plurality of alleles, these mutations may be identical to or different from each other.

Suppression of expression of at least one of the endogenous genes encompass (i) suppression of transcription from the at least one of the endogenous genes to mRNA, (ii) suppression of translation from the at least one of the endogenous genes into a polypeptide through mRNA (e.g., degradation of the mRNA), and (iii) suppression of the function of the polypeptide which has been produced by the translation. The degradation of the mRNA can occur due to the nonsense-mediated mRNA decay. The suppression of the transcription can be achieved by, for example, (i) inhibition of a transcription factor which promotes the transcription from the at least one of the endogenous genes or (ii) inhibition of access of a transcription initiation factor to the at least one of the endogenous genes. The suppression of the translation can be achieved with use of an antisense RNA molecule, an RNAi molecule, or a co-suppression molecule. The suppression of the function of the polypeptide can be achieved by a molecule which binds to a polypeptide that is functional and thereby inhibits the function of the polypeptide. Examples of such a molecule encompass decoy nucleic acids, ribozymes, antibodies, and inhibitory peptides.

The vector used to transform the tobacco plant for the purpose of suppression of expression of the at least one of the endogenous genes or introduction of the mutation into the at least one of the endogenous genes is not limited to any particular one, provided that a polynucleotide which is inserted in the vector can be expressed in a plant cell. Suitable examples of the vector encompass pBI, pPZP, and pSMA vectors each of which allows introduction of a target polynucleotide into a plant cell via *Agrobacterium*. In particular, plasmids of binary vectors (e.g., pBIG, pBIN19, pBI101, pBI121, and pPZP202) are preferable.

In a case where suppression of expression of the at least one of the endogenous genes is achieved by RNAi, a trigger sequence, which is used by RNAi to suppress expression of a target gene, is inserted into the vector. Examples of the trigger sequence encompass (i) a polynucleotide (sense RNA portion) which is (a) a part of a polynucleotide (which can have substitution of 0.1% to 1%) encoding a polypeptide having the amino acid sequence represented by SEQ ID NO: 2, 5, or 6 or a part of a polynucleotide (which can have substitution of 0.1% to 1%) having a nucleotide sequence represented by SEQ ID NO: 1, 3, 4, 35, 36, or 37 and (b) represented by a nucleotide sequence of at least 21 to 30 consecutive bases (e.g., 21 or more bases, 22 or more bases, 23 or more bases, 24 or more bases, 25 or more bases, 26 or more bases, 27 or more bases, 28 or more bases, 29 or more bases, and 30 or more bases) and (ii) a polynucleotide (antisense RNA portion) which is represented by a nucleotide sequence that is complementary to the polynucleotide (i). More specifically, the nucleotide sequence of the "at least 21 to 30 consecutive bases" described above means a nucleotide sequence of 21 or more consecutive bases, 23 or more consecutive bases, 25 or more consecutive bases, 30 or more consecutive bases, 35 or more consecutive bases, 40 or more consecutive bases, 45 or more consecutive bases, 50 or more consecutive bases, 60 or more consecutive bases, 70 or more consecutive bases, 80 or more consecutive bases, 90 or more consecutive bases, or 100 or more consecutive bases. In a preferred embodiment, the above "trigger sequence" is neither a part nor a complementary strand of polynucleotides having nucleotide sequences represented by SEQ ID NOs: 68 to 70.

The above suppression (of the transcription, the translation, or the function of the polypeptide) can be achieved by, for example, (i) directly introducing a molecule for achieving the suppression into a plant or (ii) introducing, into a plant, a nucleic acid molecule encoding the molecule (i.e., transformation of the plant). Note, here, that as a result of the transformation of the plant, the nucleic acid molecule is incorporated into any one or more regions of a genome of the plant. In the case of *Nicotiana tabacum*, which is an amphidiploid, provided that the suppression is achieved, it is unnecessary for the nucleic acid molecule to be incorporated into both an S genome and a T genome as a result of the transformation of the plant.

In the tobacco plant, the suppression of the function may be a decrease in the amount of translation into the polypeptide, which is a product of expression of the at least one of the endogenous genes, as compared with a wild-type plant. The translation into the polypeptide occurs based on (i) a decrease in mRNA (due to, for example, the amount of the mRNA which amount results from the instability of the mRNA itself, promotion of degradation of the mRNA, or suppression of the transcription of the mRNA) or (ii) a decrease in the amount of the translation of the mRNA (due to, for example, lack of elements (tRNA and ribosome) involved in the translation, inhibition of recruit, or functional impairment).

In the tobacco plant, the suppression of the function may be a decrease in an amount of transcription of the mRNA from the at least one of the endogenous genes, as compared with a wild-type plant. The decrease in the amount of the transcription of the mRNA occurs due to, for example, suppression of the transcription of the mRNA from the at least one of the endogenous genes. The suppression of the transcription can be achieved by, for example, inhibition of access of a transcription initiation factor to the at least one of the endogenous genes, which occurs as a result of introduction of the mutation into the at least one of the endogenous genes.

In the tobacco plant, the suppression of the function may be promotion of degradation of the mRNA which has been transcribed from the at least one of the endogenous genes. The degradation of the mRNA can be caused by, for example, (i) production of abnormal mRNA (causes nonsense-mediated mRNA decay), (ii) the presence of an exogenous factor leading to the degradation of the mRNA, (iii) activation of an endogenous element leading to the degradation of the mRNA, or (iv) the presence of a sequence for promoting the degradation of the mRNA. In a case where the degradation of the mRNA which has been transcribed from the at least one of the endogenous genes is promoted in the tobacco plant, the mRNA in the tobacco plant is decreased. That is, in the tobacco plant, the suppression of the function may be a decrease in the amount of the mRNA which has been transcribed from the at least one of the endogenous genes, as compared with a wild-type plant. Note, here, that the expression "decrease in the amount of the mRNA which has been transcribed from the at least one of the endogenous genes" means that such a transcription product is present at a percentage of 70% or less, 60% or less, 50% or less, 40% or less, 30% or less, 20% or less, 10% or less, 5% or less, or 1% or less with respect to the amount of a transcription product produced from the at least one of the endogenous genes in a wild-type plant.

In the tobacco plant, the mutation may be insertion, in an outside of a region in which the at least one of the endogenous genes is present, of a polynucleotide which expresses a factor that promotes the degradation of the mRNA that has been transcribed from the at least one of the endogenous genes. The factor may be an antisense RNA molecule, an RNAi molecule, or a co-suppression molecule.

An embodiment of the tobacco plant in which the mutation is insertion in an outside of a region in which the at least one of the endogenous genes is present can be replaced with two (8) in the section (Recap) immediately preceding Examples.

In a tobacco plant in accordance with an aspect of the present invention, a function of an endogenous gene is suppressed, the endogenous gene containing, as a coding region, a polynucleotide that encodes a polypeptide consisting of an amino acid sequence represented by SEQ ID NO: 2, 5, or 6. SEQ ID NO: 2 represents an amino acid sequence of AO2 of *Nicotiana sylvestris* (herein also referred to as "NsAO2"). SEQ ID NO: 5 represents an amino acid sequence of AO2 encoded by an S genome of *Nicotiana tabacum* (herein also referred to as "NtAO2-S"). SEQ ID NO: 6 represents an amino acid sequence of AO2 encoded by a T genome of *Nicotiana tabacum* (herein also referred to as "NtAO2-T").

SEQ ID NO: 1 represents a CDS sequence (encoding an amino acid represented by SEQ ID NO: 2) of an NsAO2 gene. SEQ ID NO: 35 is a genomic DNA sequence of the NsAO2 gene, the genomic DNA sequence containing, in a coding region, a nucleotide sequence represented by SEQ ID NO: 1. SEQ ID NO: 3 represents a CDS sequence (encoding an amino acid represented by SEQ ID NO: 5) of an NtAO2-S gene. SEQ ID NO: 36 is a genomic DNA sequence of an NtAO2-S gene, the genomic DNA sequence containing, in a coding region, a nucleotide sequence represented by SEQ ID NO: 3. SEQ ID NO: 4 represents a CDS sequence (encoding an amino acid represented by SEQ ID NO: 6) of the NtAO2-T gene. SEQ ID NO: 37 is a genomic DNA sequence of the NtAO2-T gene, the genomic DNA sequence containing, in a coding region, a nucleotide sequence represented by SEQ ID NO: 4.

In the tobacco plant in accordance with an aspect of the present invention, a function of an endogenous gene is suppressed, the endogenous gene containing, as a coding region, a polynucleotide that encodes a polypeptide having a sequence identity of 95% or higher with an amino acid sequence represented by SEQ ID NO: 2, 5, or 6 and having aspartate oxidase activity.

In a preferred embodiment, in the tobacco plant, a function of an endogenous gene is not suppressed, the endogenous gene containing, as a coding region, a polynucleotide that encodes a polypeptide having a sequence identity of 95% or higher (96%, 97%, 98%, 99%, and 100%) with an amino acid sequence represented by SEQ ID NO: 62, 63, or 64 and having aspartate oxidase activity. In a case where two such endogenous genes are present in the tobacco plant, the coding region of one of the endogenous genes encodes a polypeptide having the above sequence identity with an amino acid sequence represented by SEQ ID NO: 62 or 63. In a case where two such endogenous genes are present in the tobacco plant, the coding region of the other of the endogenous genes encodes a polypeptide having the above sequence identity with an amino acid sequence represented by SEQ ID NO: 64.

SEQ ID NO: 62 represents an amino acid sequence of AO1 (NsAO1) of *Nicotiana sylvestris*. SEQ ID NO: 65 represents a CDS sequence (encoding an amino acid represented by SEQ ID NO: 62) of an NsAO1 gene. SEQ ID NO: 68 is a genomic DNA sequence of the NsAO1 gene, the genomic DNA sequence containing, in a coding region, a nucleotide sequence represented by SEQ ID NO: 65. SEQ ID NO: 63 represents an amino acid sequence of AO1 (NtAO1-S) encoded by an S genome of *Nicotiana tabacum*. SEQ ID NO: 66 represents a CDS sequence (encoding an amino acid represented by SEQ ID NO: 63) of an NtAO1-S gene. SEQ ID NO: 69 is a genomic DNA sequence of an NtAO1-S gene, the genomic DNA sequence containing, in a coding region, a nucleotide sequence represented by SEQ ID NO: 66. SEQ ID NO: 64 represents an amino acid sequence of AO1 (NtAO1-T) encoded by a T genome of *Nicotiana tabacum*. SEQ ID NO: 67 represents a CDS sequence (encoding an amino acid represented by SEQ ID NO: 64) of the NtAO1-T gene. SEQ ID NO: 70 is a genomic DNA sequence of the NtAO1-T gene, the genomic DNA sequence containing, in a coding region, a nucleotide sequence represented by SEQ ID NO: 67.

The term "sequence identity (of an amino acid sequence)" as used herein means a percentage at which a concerned (amino acid) sequence matches a reference (amino acid) sequence. Note, here, that a part of the sequence which part does not match is a part at which an amino acid residue is substituted, added, deleted, or inserted.

Note, here, that "polypeptide having a sequence identity of 95% or higher with an amino acid sequence represented by [ . . . ]", which specifies a polypeptide with use of one of amino acid sequences listed in a sequence listing, may be a polypeptide which is typically present in a tobacco plant. The terms "polypeptide" and "protein" herein have substantially the same meaning, and can therefore be used interchangeably.

Therefore, the specific polypeptide which is present in a decreased amount in the tobacco plant in accordance with an aspect of the present invention need only be a polypeptide having a sequence identity of 95% or higher with each of the amino acid sequences listed in the sequence listing. A higher sequence identity is preferable (e.g., 96%, 97%, 98%, or 99% or higher).

The "decreased amount" of the polypeptide means that the polypeptide is present at a percentage of 70% or less, 60% or less, 50% or less, 40% or less, 30% or less, 20% or less, 10% or less, 5% or less, or 1% or less with respect to the amount of a wild-type polypeptide. The amount of the polypeptide with respect to the amount of the wild-type polypeptide can be selected, as appropriate, from the above-described values which cause a low alkaloid content in the tobacco plant.

Note that it is preferable that the above-described decrease in the amount of the polypeptide present in the tobacco plant in accordance with an aspect of the present invention be genetically and stably inherited by a cultured cell, a callus, protoplast, a seed, and offspring each of which is obtained from the tobacco plant. Therefore, the tobacco plant in accordance with an aspect of the present invention can be an individual developed from the cultured cell, the callus, the protoplast, the seed, and the offspring, each of which has been produced through an artificial operation. Thus, these materials, from each of which the individual develops, are also encompassed in the scope of the present invention.

The tobacco plant in accordance with an aspect of the present invention can further encompass bred progeny obtained by crossing. Breeding with use of mutants has been performed in many plant species, including rice, wheat, barley, and soybean. For example, a mutant isolated from a mutant population treated with a mutagen has multiple mutations in a region other than a region of a target gene. In general, therefore, backcrossing is performed to remove an excess mutation(s). In the course of breeding, in a case where the mutant is crossed with a cultivar having an excellent character so that a character of the mutant is introduced into the cultivar, it is possible to obtain a cultivar having high additional values. A mutant has a character that is derived from a mutation. Thus, in order to proceed backcrossing, it is necessary to select an individual having a mutation. In this case, fewer mutations that cause an intended character (low alkaloid in the present invention) reduce the number of mutations to be focused on. This reduces labor involved in backcrossing. In order to proceed efficient backcrossing, it is necessary to carry out a method by which it is easy to determine (i) whether there is any mutation and (ii) whether or not the mutation is homozygous or heterozygous. This method can be carried out through a method of detecting a mutation (described later). In addition, in a case where marker assisted selection (MAS) is performed with use of a background marker indicative of a polymorphism between the mutant and the cultivar, it is possible to efficiently obtain, with the fewer times of crossing, a line having a high cultivar-genome-rate. A polymorphic marker can be SNP or Simple Sequence Repeat (SSR), each of which is publicly known in tobacco. If necessary, a genome sequence of tobacco to be used is analyzed so as to identify (i) a difference in nucleotide sequence and (ii) a difference in the number of repeat sequences. This allows a new polymorphic marker to be obtained and utilized.

In the tobacco plant in accordance with an aspect of the present invention, a function of an endogenous gene is suppressed, the endogenous gene containing, as a coding region, a polynucleotide that encodes a polypeptide (i) consisting of an amino acid sequence in which one or several amino acids are deleted, substituted, or added from/in/to the amino acid sequence represented by SEQ ID NO: SEQ ID NO: 2, 5, or 6 and (ii) having aspartate oxidase activity. Note here that the number of amino acids that are deleted, substituted, or added from/in/to each of the amino acid sequences is, for example, 1 to 30, 1 to 25, 1 to 20, 1 to 15, 1 to 10, 1 to 9, 1 to 8, 1 to 7, 1 to 6, 1 to 5, 1 to 4, 1 to 3, 1 to 2, or 1.

In the tobacco plant in accordance with an aspect of the present invention, a function of an endogenous gene is suppressed, the endogenous gene containing, as a coding region, a polynucleotide consisting of a nucleotide sequence represented by SEQ ID NO: 1, 3, or 4. Note here that SEQ ID NOs: 1, 3, and 4 represent respective nucleotide sequences of coding regions of (i) AO2 (NsAO2) of *Nicotiana sylvestris*, (ii) AO2 (NtAO2-S) encoded by an S genome of *Nicotiana tabacum*, and (iii) AO2 (NtAO2-T) encoded by a T genome of *Nicotiana tabacum*.

In the tobacco plant in accordance with an aspect of the present invention, a function of an endogenous gene is suppressed, the endogenous gene containing, as a coding region, a polynucleotide that encodes a polypeptide (i) hybridizing, under stringent conditions, to a polynucleotide consisting of a nucleotide sequence complementary to a polynucleotide consisting of a nucleotide sequence represented by SEQ ID NO: 1, 3, or 4 and (ii) having aspartate oxidase activity.

The stringent conditions indicate, in general, conditions under which (i) a double-stranded polynucleotide which is specific to a nucleotide sequence is formed but (ii) formation of a double-stranded polynucleotide which is not specific to the nucleotide sequence is markedly suppressed. In other words, the stringent conditions can be such that hybridization is carried out at a temperature falling within a range from (i) a melting temperature (Tm) of a hybrid of nucleic acids which are highly homologous to each other (e.g., a double-stranded polynucleotide which perfectly matches a probe) to (ii) a temperature 15° C. lower, preferably 10° C. lower, more preferably 5° C. lower than the melting temperature (Tm). For example, the stringent conditions can be such that hybridization is carried out, in a common buffer solution for hybridization, at 68° C. for 20 hours. In one example, hybridization is carried out, in a buffer solution (0.25 M Na2HPO4; pH 7.2; 7% SDS; 1 mM EDTA; and 1×Denhardt's solution), at 60° C. to 68° C., preferably 65° C., more preferably 68° C. for 16 hours to 24 hours, and then washing is carried out, in a buffer solution (20 mM Na2HPO4; pH 7.2; 1% SDS; and 1 mM EDTA), at 60° C. to 68° C., preferably at 65° C., more preferably at 68° C. for 15 minutes. This washing is carried out twice. In another example, prehybridization is carried out overnight at 42° C. in a hybridization solution (containing 25% formamide or 50% formamide (for a more stringent condition); 4×SSC (sodium chloride/sodium citrate); 50 mM Hepes pH 7.0; 10×Denhardt's solution; and 20 µg/ml denatured salmon sperm DNA), and then hybridization is carried out by adding a labeled probe thereto and keeping a resulting solution overnight at 42° C. In washing following the hybridization, conditions of a washing solution and a temperature are approximately "1×SSC, 0.1% SDS, 37° C.", approximately "0.5×SSC, 0.1% SDS, 42° C." for a more stringent condition, approximately "0.2×SSC, 0.1% SDS, 65° C." for a still more stringent condition. It can be thus expected that as the conditions of the washing following the hybridization become more stringent, DNA having higher homology to a sequence of a probe is isolated. Note, however, that the above combinations of the conditions of the SSC, the SDS, and the temperature are merely examples. A person skilled in the art can achieve stringency similar to the above by appropriately combining the above or other elements (e.g., a probe concentration, a probe length, and a time period for a hybridization reaction) that determine the stringency of hybridization. For example, a person skilled in the art can easily obtain such a gene by referring to Molecular Cloning (Sambrook, J. et al., Molecular Cloning: a Laboratory Manual 2nd ed., Cold Spring Harbor Laboratory Press, 10 Skyline Drive Plainview, NY (1989)).

[2. Method of Producing Tobacco Plant]

An embodiment of the present invention provides a method of producing a tobacco plant, the method including the step of introducing, in at least one of the endogenous genes of (a) and (b) in a genome of the tobacco plant, a mutation that specifically causes suppression of a function of the at least one of the endogenous genes of (a) and (b). The mutation that is introduced in the tobacco plant is described in detail in the section [1. Tobacco plant].

In the method of producing a tobacco plant, an individual exhibiting a desired phenotype can be further selected from a plant mutant population having a mutation. As an example of the selection of the individual, the following description will discuss a procedure for selecting a desired individual from a mutant population (panel) which is obtained in a case where a treatment is carried out with use of a mutagen.

A mutant of a tobacco plant which mutant the function of which is impaired due to mutations in two alleles (in the case of *Nicotiana tabacum*, a total of four alleles in both a T genome and an S genome) can be obtained by, for example, the following method. A tobacco plant is treated with use of a mutagen, as has been described above, to prepare a population (panel) of mutants each having mutations in the whole genome. Subsequently, genomic DNAs are extracted. With use of gene-specific primers in the genomes, target genes (polynucleotides) are amplified from the genomic DNAs of the panel. Thereafter, nucleotide sequences of resulting products are determined, and lines each having a homozygous mutation are then selected. For example, in the case of *Nicotiana tabacum*, first, a line (M2) having a homozygous mutation in an S genome and a line (M2) having a homozygous mutation in a T genome are obtained and then crossed to prepare F1 individuals. Subsequently, selfed progeny (F2) is developed from the F1 individuals. From the selfed progeny (F2), a line having homozygous mutations in both an S genome and a T genome is obtained. For obtainment of a mutant of a tobacco plant the function of which is impaired due to a mutation in only one of the S genome and the T genome, it is only necessary to confirm that no mutation occurs in a gene in a genome which is not a target in the obtained M2.

An individual exhibiting a desired phenotype can be selected by measurement of an alkaloid content or measurement of aspartate oxidase activity.

As an example of a method for producing a tobacco having a mutation in an AO2 gene, a tobacco is treated with use of a mutagen such as EMS as has been described above, to prepare a population (panel) of tobacco mutants each having mutations in the whole tobacco genome. Subsequently, genomic DNAs are extracted. With use of primers specific to genes, the AO2 gene is amplified from the genomic DNAs of the panel or from those pooled. Subsequently, nucleotide sequences of resulting products are determined, and lines each having a homozygous mutation are then selected. First, a line having a homozygous mutation in an S-type genome and a line having a homozygous mutation in a T-type genome are obtained and then crossed to prepare F1 individuals. Subsequently, selfed progeny (F2) is developed from the F1 individuals. From the selfed progeny (F2), a line having homozygous mutations in both an S-type genome and a T-type genome is obtained (such a line is obtained at a probability of 1/16 since two factors are recessive).

Thus, the method of an embodiment may further include the following one or more steps:

the step of preparing a population (panel) of tobacco mutants each having mutations in the whole tobacco genome;
  the step of extracting a genomic DNA from a line contained in the panel;
  the step of determining a nucleotide sequence of an AO2 gene in the genomic DNA;
  the step of selecting, from the panel, a line containing a homozygous mutation; and
  the step of determining an alkaloid content in the line.

At any point in time prior to carrying out the step of determining the alkaloid content, the line can be crossed with a line that has not been subjected to a mutation treatment. The crossing allows elimination of a mutation that can be present other than a mutation in the AO2 gene. In a specific embodiment, the line having the mutation in the AO2 gene can be backcrossed a plurality of times with a line that has not been subjected to the mutation treatment (an original line used to prepare the panel).

Extraction of genomic DNA from a tobacco mutant only needs to be performed by a publicly-known method, and may be performed with use of a commercially available extraction kit. Further, genomic DNA may be a crudely purified one or may be a purified one obtained through several purification steps.

Amplification of a polynucleotide can be performed by, for example, a PCR method, but may be performed by any of other publicly-known gene amplification methods including, for example, a ligase chain reaction (LCR) method and a Loop-Mediated Isothermal Amplification (LAMP) method.

A primer sequence for amplifying each polynucleotide can be designed from, for example, a nucleotide sequence. First, an S-type specific region and a T-type specific region are determined from a result of analysis of homology between the nucleotide sequence represented by SEQ ID NO: 36 (genome sequence of an S-type AO2 gene) and the nucleotide sequence represented by SEQ ID NO: 37 (genome sequence of a T-type AO2 gene). By designing primers for those regions, the S-type AO2 gene and the T-type AO2 gene can be independently amplified specifically from extracted genomic DNA (containing an S-type genome and a T-type genome). A target site at which each of the primers is designed can be selected from the S-type specific region or the T-type specific region, but is preferably an intron, a 5' untranslated region, or a 3' untranslated region. The length of each primer is preferably 15 bases to 30 bases, and particularly preferably 17 bases to 25 bases. The primer sequence may be designed based on a sequence of the region specific to the nucleotide sequence, or a sequence of a region which is shared by both the nucleotide sequences. As long as the primer can serve as a primer for amplifying a sequence of a predetermined number of bases including a mutation site, the sequence of the primer may include one or more substitutions, deletions, and/or additions. Further, the primer may be labeled with, for example, a fluorescent substance or a radioactive substance, if necessary.

The length of each polynucleotide to be amplified can be any length that is permitted to be used by various detection methods (described later) and is, for example, 20 bases to 5000 bases, more preferably 50 bases to 2000 bases, even more preferably 100 bases to 700 bases, and still more preferably 100 bases to 500 bases.

[3. Others]

An embodiment of the present invention provides a method of determining a tobacco plant having a low alkaloid content. The method includes the following steps:

the step of obtaining a sample by collecting a part of a tobacco plant;

the step of detecting a mutation that specifically causes suppression of the function of the at least one of the endogenous genes in a genome contained in the sample; and the step of determining that a tobacco plant, in which the mutation has been detected, is a tobacco plant having a low alkaloid content.

Note here that the suppression of the function causes a low alkaloid content in a tobacco plant. That is, the determining method can be used for, for example, a method of producing a tobacco plant.

An embodiment of the present invention provides a method of breeding a tobacco plant. The breeding method includes the step of crossing tobacco plants each determined by the determining method and each having a low alkaloid content.

An embodiment of the present invention provides offspring or bred progeny, the offspring being of a tobacco plant recited above, a tobacco plant produced by a method recited above, a tobacco plant determined by a determining method recited above, or a tobacco plant produced by a breeding method recited above, the bred progeny being obtained by crossing a tobacco plant recited above, a tobacco plant produced by a method recited above, a tobacco plant determined by a determining method recited above, or a tobacco plant produced by a breeding method recited above with another tobacco plant. In the present embodiment, in the case of, for example, *Nicotiana sylvestris*, merely suppression of a function of a single AO2 gene results in an extremely low nicotine content. This enables breeding in a mode of single-factor recessive inheritance in which mode a mutation in the AO2 gene is used as a guide. As compared with conventional breeding, breeding in such a mode greatly reduces labor involved in breeding. In the case of, for example, *Nicotiana tabacum*, merely suppression of a function of two AO2 genes results in an extremely low nicotine content. This enables breeding in a mode of two-factor recessive inheritance in which mode a mutation in the AO2-S gene and a mutation in the AO2-T gene are used as a guide. As compared with conventional breeding, breeding in such a mode further reduces labor involved in breeding. Furthermore, merely suppression of a function of a single AO2 gene results in low nicotinic properties. This enables breeding in a mode of single-factor recessive inheritance in which mode a mutation in the AO2-S gene or a mutation in the AO2-T gene is used as a guide. As compared with conventional breeding, breeding in such a mode greatly reduces labor involved in breeding.

Breeding with use of mutants has been performed in many plant species. For example, a mutant isolated from a mutant population which has been obtained by a treatment with use of a mutagen has multiple mutations in a region other than a region of a target gene. In general, therefore, backcrossing is performed to remove an excess mutation(s). In this crossing, a desired character of the mutant can be introduced into an existing cultivar by crossing the mutant with the cultivar having an excellent character. Bred progeny thus obtained can be a variety obtained by adding high values to an existing cultivar. In this case, fewer intended mutations that cause low alkaloid reduce the number of mutations to be focused on. This reduces labor involved in backcrossing.

An embodiment of the present invention provides a tobacco leaf harvested from (i) a tobacco plant recited above, (ii) a tobacco plant produced by a method recited above, (iii) a tobacco plant determined by a determining method recited above, (iv) a tobacco plant produced by a breeding method recited above, or (v) offspring or bred progeny recited above. The tobacco leaf refers to a leaf that is harvested from a tobacco plant and used to produce a tobacco product.

An embodiment of the present invention provides a cured leaf (cured tobacco) obtained from the tobacco leaf. The cured leaf is obtained by curing the tobacco leaf. As a curing method, any method can be employed. The curing method can be, but is not limited to, air curing, warm-air curing, flue curing, or the like, for example. Note that the cured leaf herein encompasses cut fillers, powders, sheets, stems, granules, and extracts each of which is obtained from the cured leaf.

An embodiment of the present invention provides a tobacco product obtained from the cured leaf. The tobacco product can be in any form. The tobacco product can be, but is not limited to, shred tobaccos, cigars, pipe smoking tobaccos, paper-wrapped cigarettes, electronic tobaccos, smokeless tobaccos, snuff tobaccos (including snus and snuff), hookah tobaccos, heat-not-burn tobacco products (using, as an aerosol source, aerosol generated by heating of tobacco), non-heated tobacco products (for inhaling a flavor of tobacco without heating the tobacco), or the like, for example.

For details of these, a reference can be made to the above-mentioned matters concerning a tobacco plant and a method of producing the tobacco plant.

(Recap)

With the above embodiments considered together, the present invention can be summarized as follows.

Specifically, (1) A tobacco plant in which a mutation that specifically causes suppression of a function of an endogenous gene is introduced in a genome, the endogenous gene being at least one of:

an endogenous gene which contains, as a coding region, a polynucleotide that encodes a polypeptide having a sequence identity of 95% or higher with an amino acid sequence represented by SEQ ID NO: 2 or SEQ ID NO: 5; and an endogenous gene which contains, as a coding region, a polynucleotide that encodes a polypeptide having a sequence identity of 95% or higher with an amino acid sequence represented by SEQ ID NO: 6.

(2) The tobacco plant recited in (1), wherein the suppression of the function is a decrease in an amount of the polypeptide, as compared with a wild-type plant.

(3) The tobacco plant recited in (2), wherein the suppression of the function is a decrease in an amount of translation into the polypeptide, as compared with a wild-type plant.

(4) The tobacco plant recited in (2), wherein the suppression of the function is a decrease in an amount of transcription from the at least one of the endogenous genes to mRNA, as compared with a wild-type plant.

(5) The tobacco plant recited in (2), wherein the suppression of the function is promotion of degradation of mRNA which has been transcribed from the at least one of the endogenous genes.

(6) The tobacco plant recited in any one of (1) through (5), wherein the mutation is introduced in the at least any one of the endogenous genes.
(7) The tobacco plant recited in (6), wherein the mutation is introduced by spontaneous mutation, mutagen treatment, genome editing, or gene knockout.
(8) The tobacco plant recited in (5), wherein the mutation is insertion, in an outside of a region in which the at least one of the endogenous genes is present, of a polynucleotide which expresses a factor that promotes the degradation of the mRNA.
(9) The tobacco plant recited in (8), wherein the factor is an antisense RNA molecule, an RNAi molecule, or a co-suppression molecule.
(10) The tobacco plant recited in any one of (1) through (9), wherein the tobacco plant belongs to *Nicotiana tabacum, Nicotiana sylvestris*, or *Nicotiana rustica*.
(11) A method of producing a tobacco plant, including the step of introducing a mutation in a genome of a tobacco plant, the mutation specifically causing suppression of a function of at least one of:
  an endogenous gene which contains, as a coding region, a polynucleotide that encodes a polypeptide having a sequence identity of 95% or higher with an amino acid sequence represented by SEQ ID NO: 2 or SEQ ID NO: 5; and
  an endogenous gene which contains, as a coding region, a polynucleotide that encodes a polypeptide having a sequence identity of 95% or higher with an amino acid sequence represented by SEQ ID NO: 6.
(12) The method recited in (11), wherein the suppression of the function is a decrease in an amount of the polypeptide, as compared with a wild-type plant.
(13) The method recited in (12), wherein the suppression of the function is a decrease in an amount of translation into the polypeptide, as compared with a wild-type plant.
(14) The tobacco plant recited in (12), wherein the suppression of the function is a decrease in an amount of transcription from the at least one of the endogenous genes to mRNA, as compared with a wild-type plant.
(15) The tobacco plant recited in (12), wherein the suppression of the function is promotion of degradation of mRNA which has been transcribed from the at least one of the endogenous genes.
(16) The method recited in any one of (11) through (15), wherein the step of introducing the mutation includes introducing the mutation in the at least one of the endogenous genes.
(17) The method recited in (16), wherein the step of introducing the mutation is carried out by spontaneous mutation, mutagen treatment, genetic modification, genome editing, or gene knockout.
(18) The method recited in any one of (12) through (15), wherein the step of introducing the mutation includes inserting, in an outside of a region in which the at least one of the endogenous genes is present, a polynucleotide which expresses a factor that promotes the degradation of the mRNA which has been transcribed from the at least one of the endogenous genes.
(19) The method recited in (18), wherein the factor is an antisense RNA molecule, an RNAi molecule, or a co-suppression molecule.
(20) Offspring or bred progeny, the offspring being of a tobacco plant recited in any one of (1) through (10) or a tobacco plant produced by a method recited in any one of (11) through (19), the bred progeny being obtained by crossing a tobacco plant recited in any one of (1) through (10) or a tobacco plant produced by a method recited in any one of (11) through (19) with another tobacco plant.
(21) A tobacco leaf harvested from (i) a tobacco plant recited in any one of (1) through (10), (ii) a tobacco plant produced by a method recited in any one of (11) through (19), or (iii) offspring or bred progeny recited in (20).
(22) A cured leaf produced from a tobacco leaf recited in (21).
(23) A tobacco product comprising a cured leaf recited in (22).

The above embodiments can also be alternatively summarized as follows.

(1)
A tobacco plant in which a mutation that specifically causes suppression of a function of an endogenous gene is introduced in the endogenous gene in a genome, the endogenous gene being at least one of:
  (a) an endogenous gene which contains, as a coding region, a polynucleotide that encodes a polypeptide having a sequence identity of 95% or higher with an amino acid sequence represented by SEQ ID NO: 2 or SEQ ID NO: 5; and
  (b) an endogenous gene which contains, as a coding region, a polynucleotide that encodes a polypeptide having a sequence identity of 95% or higher with an amino acid sequence represented by SEQ ID NO: 6.
(2)
The tobacco plant recited in (1), wherein the suppression of the function is a decrease in an amount of mRNA which has been produced from the at least one of the endogenous genes, as compared with a wild-type plant.
(3)
The tobacco plant recited in (2), wherein the suppression of the function is promotion of degradation of the mRNA which has been produced from the at least one of the endogenous genes, as compared with a wild-type plant.
(4)
The tobacco plant recited in (2), wherein the suppression of the function is a decrease in an amount of transcription from the at least one of the endogenous genes to the mRNA, as compared with a wild-type plant.
(5)
The tobacco plant recited in any one of (1) through (4), wherein the suppression of the function is a decrease in an amount of the polypeptide, as compared with a wild-type plant.
(6)
The tobacco plant recited in (5), wherein the suppression of the function is a decrease in an amount of translation into the polypeptide, as compared with a wild-type plant.
(7)
The tobacco plant recited in any one of (1) through (6), wherein the mutation is introduced by mutagen treatment, genome editing, or gene knockout.
(8)
The tobacco plant recited in any one of (1) through (7), wherein the tobacco plant belongs to *Nicotiana tabacum, Nicotiana sylvestris*, or *Nicotiana rustica*.
(9)
The tobacco plant recited in any one of (1) through (8), wherein respective functions of the following endogenous genes (c) and (d) are not suppressed:

(c) an endogenous gene which contains, as a coding region, a polynucleotide that encodes a polypeptide having a sequence identity of 95% or higher with an amino acid sequence represented by SEQ ID NO. 62 or SEQ ID NO: 63; and (d) an endogenous gene which contains, as a coding region, a polynucleotide that encodes a polypeptide having a sequence identity of 95% or higher with an amino acid sequence represented by SEQ ID NO. 64.

(10)

A method of producing a tobacco plant, including the step of introducing a mutation in a genome of a tobacco plant, the mutation specifically causing suppression of a function of at least one of:

(a) an endogenous gene which contains, as a coding region, a polynucleotide that encodes a polypeptide having a sequence identity of 95% or higher with an amino acid sequence represented by SEQ ID NO: 2 or SEQ ID NO: 5; and (b) an endogenous gene which contains, as a coding region, a polynucleotide that encodes a polypeptide having a sequence identity of 95% or higher with an amino acid sequence represented by SEQ ID NO: 6, the step of introducing the mutation including introducing the mutation in the at least one of the endogenous genes.

(11)

The method recited in (10), wherein the suppression of the function is a decrease in an amount of mRNA which has been produced from the at least one of the endogenous genes, as compared with a wild-type plant.

(12)

The method recited in (11), wherein the suppression of the function is promotion of degradation of the mRNA which has been produced from the at least one of the endogenous genes, as compared with a wild-type plant.

(13)

The method recited in (11), wherein the suppression of the function is a decrease in an amount of transcription from the at least one of the endogenous genes to the mRNA, as compared with a wild-type plant.

(14)

The method recited in any one of (10) through (13), wherein the suppression of the function is a decrease in an amount of the polypeptide, as compared with a wild-type plant.

(15)

The method recited in (14), wherein the suppression of the function is a decrease in an amount of translation into the polypeptide, as compared with a wild-type plant.

(16)

The method recited in any one of (10) through (15), wherein the step of introducing the mutation is carried out by mutagen treatment, genetic modification, genome editing, or gene knockout.

(17)

A method recited in any one of (10) through (16), further including not suppressing respective functions of the following endogenous genes (c) and (d):

(c) an endogenous gene which contains, as a coding region, a polynucleotide that encodes a polypeptide having a sequence identity of 95% or higher with an amino acid sequence represented by SEQ ID NO. 62 or SEQ ID NO: 63; and (d) an endogenous gene which contains, as a coding region, a polynucleotide that encodes a polypeptide having a sequence identity of 95% or higher with an amino acid sequence represented by SEQ ID NO. 64.

(18)

Offspring or bred progeny, the offspring being of a tobacco plant recited in any one of (1) through (9) or a tobacco plant produced by a method recited in any one of (10) through (17), the bred progeny being obtained by crossing a tobacco plant recited in any one of (1) through (9) or a tobacco plant produced by a method recited in any one of (10) through (17) with another tobacco plant.

(19)

A tobacco leaf having a mutation in (a) an endogenous gene in a genome which endogenous gene contains, as a coding region, a polynucleotide that encodes a polypeptide having a sequence identity of 95% or higher with an amino acid sequence represented by SEQ ID NO: 2 or SEQ ID NO: 5, the mutation suppressing a function of the endogenous gene, and/or having a mutation in (b) an endogenous gene in a genome which endogenous gene contains, as a coding region, a polynucleotide that encodes a polypeptide having a sequence identity of 95% or higher with an amino acid sequence represented by SEQ ID NO: 6, the mutation suppressing a function of the endogenous gene, and having a lower alkaloid content as compared with a tobacco leaf harvested from a wild-type tobacco plant.

(20)

A cured leaf having a mutation in (a) an endogenous gene in a genome which endogenous gene contains, as a coding region, a polynucleotide that encodes a polypeptide having a sequence identity of 95% or higher with an amino acid sequence represented by SEQ ID NO: 2 or SEQ ID NO: 5, the mutation suppressing a function of the endogenous gene, and/or having a mutation in (b) an endogenous gene in a genome which endogenous gene contains, as a coding region, a polynucleotide that encodes a polypeptide having a sequence identity of 95% or higher with an amino acid sequence represented by SEQ ID NO: 6, the mutation suppressing a function of the endogenous gene, and having a lower alkaloid content as compared with a cured leaf produced from a tobacco leaf harvested from a wild-type tobacco plant.

(21)

A tobacco product comprising a cured leaf recited in (20).

The following description will more specifically discuss an embodiment of the present invention with reference to Examples. The present invention is, of course, not limited to the Examples below and particulars can have various aspects. Further, the present invention is not limited to the embodiments, but can be altered by a skilled person in the art within the scope of the claims. An embodiment derived from a proper combination of technical means disclosed in respective different embodiments is also encompassed in the technical scope of the present invention. Moreover, all the literatures described herein are hereby incorporated by reference.

EXAMPLES

Example 1: Isolation of *Nicotiana sylvestris* Low Nicotine Producing Mutant Line (SNIC Line)

A cultivated tobacco *Nicotiana tabacum* (chromosome number: 2n=4x=48) is an amphidiploid derived from hybridization of (i) a tobacco wild species *Nicotiana sylvestris* (chromosome number: 2n=2x=24) that is a diploid and (ii) a tobacco wild species *Nicotiana tomentosiformis* (chromosome number: 2n=2x=24) that is also a diploid, and has two subgenomes derived from their respective ancestors (the subgenome derived from *Nicotiana sylvestris* and the subgenome derived from *Nicotiana tomentosiformis* are referred to as "S" or "S genome" and "T" or "T genome", respectively). Thus, in *Nicotiana tabacum*, in consideration of the presence of alleles, 2 pairs of genes having the same function for many genes (1 pair=2 alleles in an S-type genome and 1 pair=2 alleles in a T-type genome) are present. Therefore, in *Nicotiana tabacum*, in order to observe a phenotype resulted from a mutation, a mutation in which a function of a target gene is lost, it is necessary to mutate a total of all four alleles which are contained in both the S-type genome and the T-type genome and the functions of which overlap each other.

In contrast, since *Nicotiana sylvestris* is a diploid, a phenotype caused by a mutation of one gene can be observed in an M2 generation following a first generation (M1 generation) in which the mutation has occurred. Thus, a *Nicotiana sylvestris* mutant library was prepared, and an attempt was made to obtain a low nicotine producing mutant.

Seeds of *Nicotiana sylvestris* were treated with 0.6% EMS for 16 hours and then washed with distilled water 8 times for 30 minutes each. The seeds thus treated were sown to grow a plant of the treated generation (M1 generation). Selfed seeds (the M2 generation) were obtained from each line. It was possible to obtain approximately 200 or more seeds from each of 4,945 EMS mutated *Nicotiana sylvestris* lines.

A main alkaloid of *Nicotiana sylvestris* is nornicotine. In a leaf of *Nicotiana sylvestris*, nicotine is converted to nornicotine during senescence and curing. It was therefore considered that selection of a *Nicotiana sylvestris* mutant which is less capable of producing nornicotine after senescence and curing makes it possible to obtain a mutant in which nicotine, which is a precursor of nornicotine, is decreased.

A leaf of a greenhouse-grown seedling in the 6th to 7th leaf stage was subjected to a curing (senescence) treatment at 37° C. and a humidity of 85% for 3 days so that conversion from nicotine to nornicotine was promoted. A part (a tip of 2 cm×2 cm) of the treated leaf was immersed, for several seconds, in 30% NaOH containing 1% Tween-20, so that a tissue was disrupted. Then, the part of the treated leaf was immersed in 0.4 mL chloroform for 1 hour so that content components were extracted. On filter paper (Absorbent paper CB-09A, manufactured by ATTO CORPORATION), 20 μL of a chloroform layer was blotted, and an isatin solution (obtained by dissolving 0.1 g of 2,3-indolinedione (manufactured by FUJIFILM Wako Pure Chemical Corporation) in a mixed solution of 2.5 mL of acetic acid and 50 mL of ethanol) was uniformly sprayed by a sprayer, and a treatment was carried out at 120° C. for 4 minutes. In a case where nornicotine is present, nornicotine reacts with isatin so that a blue color is developed. This was used as an indicator to simply determine a nornicotine concentration. Specifically, an indicator divided into 5 stages, as indicators of color development, which are standard nornicotine contents of 0.05%, 0.1%, 0.25%, 0.5%, and 0.75%, was prepared and used as a reference for a degree of color development. These indicators of color development were regarded as nornicotine index values (or nornicotine indices) 1, 2, 3, 4, and 5, respectively. An individual having the index value 1 was to be selected.

An individual having a lower nornicotine content was transplanted into a 12-cm pot and allowed to grow for another 2 weeks. Fresh leaves were shredded, and nicotine was extracted with methanol, so that nicotine was measured by gas chromatography-mass spectrometry (GC-MS) analysis. A nicotine content was calculated as a peak area ratio to a control (wild-type *Nicotiana sylvestris*). The assay system described above was used to subject a total of 4,202 M2 generations of the EMS mutated *Nicotiana sylvestris* line to selection, and 15 individuals of (i) a mutant containing substantially no nicotine or (ii) a mutant having a nicotine content decreased to several % of the nicotine content of a control (wild-type *Nicotiana sylvestris* not having been subjected to a mutation treatment) were obtained from 8 lines (Table 1).

Selfed seeds (an M3 generation) were obtained for all individuals. The M3 generation was grown, transplanted into a 12-cm pot, and subjected to topping (bud nipping) 2 months later. After 2 weeks, roots were collected and shredded so as to be subjected to methanol extraction. Then, GC-MS analysis was carried out. As a result, the nicotine content was 0 to several % of that of the control in all the lines. This suggests that a low nicotine producing mutant is caused not by impaired translocation of nicotine from the roots to an aerial part but is caused by impaired nicotine biosynthesis in the roots (Table 1).

TABLE 1

| Line (M2) | Individual number | Nornicotine index* | Nicotine in leaves (ratio relative to wild type)** | Nicotine in roots (ratio relative to wild type) |
|---|---|---|---|---|
| 04N-257 | 3, 4, 6 | 1 | 0% to several % | 2.9% |
| 04N-584 | 8 | 1 | several % | 3.2% |
| 04M-472 | 4, 7 | 1 | 0% to several % | 0% to several % |
| 06N-615 | 2, 5 | 1 | 0% to several % | 0% to several % |
| 06N-1296 | 6, 7 | 1 | 0% to several % | 1.3% |
| 06N-4850 | 1, 7 | 1 | 0% to several % | 0.7% |
| 06N-14439 | 2 | 1 | several % | 1.7% |
| 06N-15427 | 2, 3 | 1 | 0.9% to 2.3% | 2.8% |

*Leaves of M2 generation seedlings were subjected to senescence induction, and nornicotine was detected by a simple assay method.
**M2 generation plants were transplanted into a 12-cm pot, leaves after 1.5 months were shredded so as to be subjected to methanol extraction, and then the leaves having been subjected to methanol extraction was subjected to GC-MS analysis.

Furthermore, some low nicotine producing mutants were grown in a field, and mature leaves at 1 month after topping were air-cured for 1 month. Thereafter, shredded leaves were subjected to minor alkaloid analysis (see Beitr. Tabakforsch Int., 21: 369-379 (2005)), so that a measurement for nicotine, nornicotine, anatabine, anabasine, and myosmine was carried out. Table 2 shows results.

In wild-type *Nicotiana sylvestris* (WT), a total amount of nicotine and nornicotine was 1.2% to 1.3% (12 mg/g to 13 mg/g cured leaves) per weight of cured leaves. In contrast, a total amount of nicotine and nornicotine in a low nicotine producing mutant was so low as to be less than or equal to a limit of quantitative determination to 0.024% (0.24 mg/g cured leaves). In all low nicotine lines, a total alkaloid content was less than 0.04% (0.4 mg/g cured leaves) (Table 2). As shown in Table 3, an ID of an SNIC line was assigned to each of 8 lines.

TABLE 2

| Line number | Individual number | Nicotine % | Nornicotine % | Anatabine % | Anabasine % | Myosmine % | Total alkaloid % |
|---|---|---|---|---|---|---|---|
| WT | | ND | 1.312 | 0.011 | 0.004 | 0.083 | 1.313 |
| 04N257 | 4 | ND | 0.022 | 0.008 | 0.003 | 0.003 | 0.036 |
| 04N257 | 6 | ND | 0.024 | 0.007 | 0.003 | 0.003 | 0.038 |
| WT | | ND | 1.196 | 0.017 | 0.003 | NT | 1.216 |
| 06N615 | 2 | ND | NQ (0.006) | 0.004 | NQ (0.001) | NT | NQ (0.011) |
| 06N615 | 5 | ND | NQ (0.006) | 0.004 | ND | NT | NQ (0.01) |

"ND" indicates "less than or equal to a detection limit", "NQ" indicates "less than or equal to a limit of quantitative determination", and "NT" indicates "without any analysis performed".

TABLE 3

| ID | Line (generation) |
|---|---|
| SNIC1 | 04N257-4 (M4) |
| SNIC2 | 04M472-7 (M3) |
| SNIC3 | 04N584-8 (M4) |
| SNIC4 | 06N615-5 (M3) |
| SNIC5 | 06N1296-7 (M4) |
| SNIC6 | 06N4850-7 (M4) |
| SNIC7 | 06N14439-2 (M3) |
| SNIC8 | 06N15427-2 (M3) |

Example 2: Characterization of SNIC Line

Six of the 8 SNIC lines obtained in Example 1 and *Nicotiana sylvestris* serving as a control were grown in a field. For each of the lines, 12 individuals were subjected to a test. Topping was carried out during flowering time. After approximately 6 weeks, the second leaves from the top were sampled from 3 individuals for each of the lines. Air curing (one cycle of 24 hours (30° C., a humidity of 75%, 16 hours→22° C., a humidity of 85%, 8 hours) was repeatedly carried out for 30 days (30 cycles). Subsequently, the leaves, the mid-ribs of which had been removed, were freeze-cured and then subjected to minor alkaloid analysis. As a result, a sum of a nicotine content and a nornicotine content of each of the SNIC lines was 0.04% (0.4 mg/g cured leaves) or less. This was 2.6% or less of the content (100%) in *Nicotiana sylvestris* serving as the control (Table 4). Moreover, a total alkaloid, which is a sum of the nicotine content, the nornicotine content, an anatabine content, and an anabasine content of each of the SNIC lines, was approximately 0.1% (1 mg/g cured leaves) or less.

TABLE 4

Alkaloid analysis of field-grown SNIC line and
*N. sylvestris* (average of three individuals)

| | Nicotine (%) | Nornicotine (%) | Nicotine + nornicotine (%) | Anatabine (%) | Anabasine (%) |
|---|---|---|---|---|---|
| SNIC1 | 0.005 | 0.031 | 0.036 | 0.053 | ND |
| SNIC2 | ND | 0.017 | 0.017 | 0.049 | ND |
| SNIC4 | ND | ND | ND | 0.055 | ND |
| SNIC5 | ND | ND | ND | 0.083 | ND |
| SNIC7 | ND | 0.028 | 0.028 | 0.075 | ND |
| SNIC8 | 0.002 | 0.023 | 0.025 | 0.069 | ND |
| *N. sylvestris* | 0.043 | 1.347 | 1.390 | 0.059 | ND |

"ND" indicates "less than or equal to a detection limit".

Subsequently, all the eight SNIC lines were crossed with each other so that F1 lines were prepared. Then, an allelism test was carried out with respect to low nicotinic loci.

Figure 1:
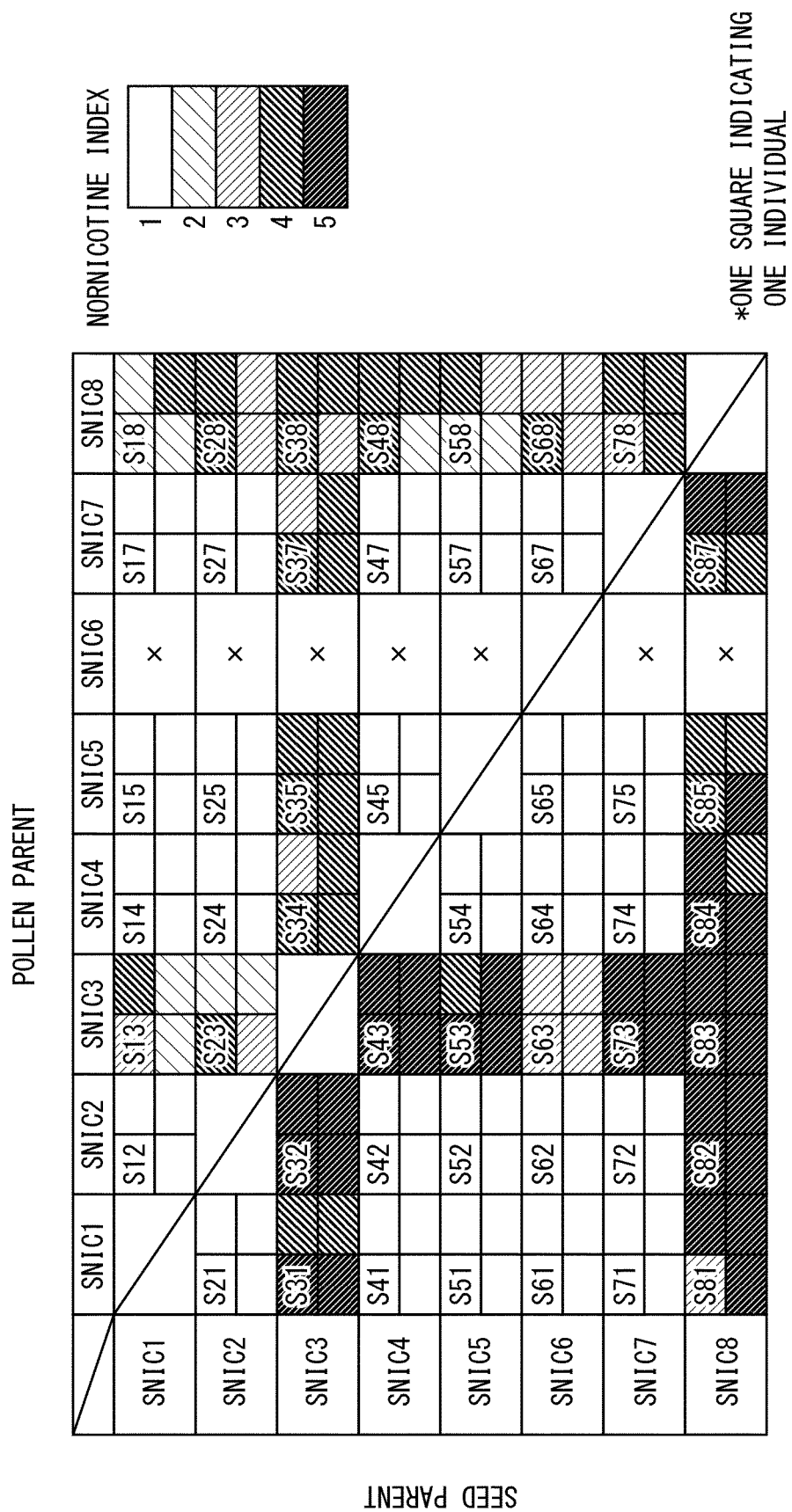
FIG. 1 is a diagram showing a result of a nornicotine assay of an F1 individual of an SNIC line.

The F1 lines were produced by reciprocal crossing of all combinations except a combination in which SNIC6 is a pollen parent (FIG. 1). For each of the lines, 4 individuals were grown in a greenhouse. The individuals were transplanted into a 9-cm pot at 5 weeks after seeding. After another approximately 2 weeks, lower leaves of the individuals were sampled and subjected to a simple nornicotine assay (described earlier).

As a result, nicotine accumulation was observed in an F1 line obtained by crossing SNIC3 or SNIC8 with the other lines. Thus, it was considered that these 2 lines produced less nicotine due to a mutation in a locus different from the other lines. Meanwhile, a nornicotine index of all F1 individuals obtained by crossing the other 6 lines (SNIC1, SNIC2, SNIC4, SNIC5, SNIC6, and SNIC7) with each other was 1. This shows that low nicotinic properties were maintained (FIG. 1). That is, it has been made clear that the low nicotinic properties of these 6 lines were controlled by a mutation of a single locus.

An F1 generation obtained by crossing each of the 2 lines SNIC4 and SNIC7 with *Nicotiana sylvestris* was prepared and further selfed, so that an F2 generation was obtained. For each of both the lines, 96 F2 individuals were grown, and a segregation ratio of low-alkaloid properties was determined (note here that "alkaloid" is a generic term for a combination of nicotine and nornicotine). Lower leaves of the individuals at approximately 2 months after seeding were sampled and subjected to the simple nornicotine assay, and an individual having a nornicotine index of 2 or less was transplanted into a 12-cm pot. Topping was carried out after approximately 1 week since the transplantation into the 12-cm pot, and then lower leaves were removed, so that only 3 upper leaves were left. Additional fertilization was carried out at 10 days after the topping, and all leaves were harvested 30 days later. Subsequently, the leaves, the mid-ribs of which had been removed, were freeze-cured and then subjected to minor alkaloid analysis. In a case where a nicotine concentration was low, according to CORESTA Recommended Method No. 62, nicotine was extracted from shredded leaves and then subjected to measurement using GC-MS.

As a result, the number of individuals in each of which a sum of a nicotine content and a nornicotine content (hereinafter also referred to as an "alkaloid content") was 0.04% or less was 25 for the F2 generation derived from the SNIC4, and 18 for the F2 generation derived from the SNIC7 (Table 5, in Table 5, "Nsyl-1" to "Nsyl-5" indicate results for a wild-type *Nicotiana sylvestris* line used as a control). The other individuals showed an alkaloid content of 2.3% at minimum. This resulted in confirmation of clear separation of the alkaloid contents. A segregation ratio between the number of individuals having an alkaloid content of 2.3% or higher and the number of individuals having an alkaloid content of 0.04% or less was 71:25 for the SNIC4, and 66:18 for the SNIC7 except for 12 individuals that had been withered and dead. This has suggested that the above segregation ratio is within an expected segregation ratio (3:1) assuming a single recessive factor dominance (×2 test, SNIC4: p=0.81, SNIC7: p=0.45) and that low alkaloid properties are dominated by a single recessive factor. Furthermore, wild-type *Nicotiana sylvestris* grown under the same condition had an alkaloid content of 3.11% to 5.03%. That is, a low-alkaloid F2 individual had an alkaloid content of 0.8% to 1.3% or less of the alkaloid content of the wild-type *Nicotiana sylvestris*. Note that a low-alkaloid F2 line was normally grown as in the case of the wild-type *Nicotiana sylvestris*.

TABLE 5

Results of analysis of alkaloid content of low alkaloid individual of F2 individuals derived from SNIC4 and SNIC7

| | Nicotine + nor- nicotine (%) | F2 derived from SNIC4 | Nicotine + nor- nicotine (%) | F2 derived from SNIC7 | Nicotine + nor- nicotine (%) |
|---|---|---|---|---|---|
| Nsyl-1 | 4.40 | SNIC4_F2_3 | 0.008 | SNIC7_F2_2 | 0.016 |
| Nsyl-2 | 4.78 | SNIC4_F2_4 | 0.012 | SNIC7_F2_4 | 0.014 |
| Nsyl-3 | 3.11 | SNIC4_F2_5 | 0.014 | SNIC7_F2_7 | 0.015 |
| Nsyl-4 | 3.59 | SNIC4_F2_7 | 0.010 | SNIC7_F2_10 | 0.022 |
| Nsyl-5 | 5.03 | SNIC4_F2_13 | 0.019 | SNIC7_F2_17 | 0.021 |
| | | SNIC4_F2_18 | 0.018 | SNIC7_F2_18 | 0.020 |
| | | SNIC4_F2_25 | 0.013 | SNIC7_F2_20 | 0.018 |
| | | SNIC4_F2_37 | 0.009 | SNIC7_F2_28 | 0.017 |
| | | SNIC4_F2_38 | 0.018 | SNIC7_F2_29 | 0.013 |
| | | SNIC4_F2_44 | 0.009 | SNIC7_F2_34 | 0.022 |
| | | SNIC4_F2_46 | 0.028 | SNIC7_F2_38 | 0.033 |
| | | SNIC4_F2_53 | 0.023 | SNIC7_F2_39 | 0.020 |
| | | SNIC4_F2_55 | 0.013 | SNIC7_F2_49 | 0.018 |
| | | SNIC4_F2_56 | 0.009 | SNIC7_F2_55 | 0.019 |
| | | SNIC4_F2_57 | 0.010 | SNIC7_F2_57 | 0.032 |
| | | SNIC4_F2_62 | 0.012 | SNIC7_F2_60 | 0.019 |
| | | SNIC4_F2_63 | 0.009 | SNIC7_F2_81 | 0.022 |
| | | SNIC4_F2_66 | 0.040 | SNIC7_F2_91 | 0.040 |
| | | SNIC4_F2_77 | 0.019 | | |
| | | SNIC4_F2_78 | 0.012 | | |
| | | SNIC4_F2_79 | 0.007 | | |
| | | SNIC4_F2_81 | 0.012 | | |
| | | SNIC4_F2_87 | 0.019 | | |
| | | SNIC4_F2_92 | 0.034 | | |
| | | SNIC4_F2_94 | 0.012 | | |

Example 3: Identification of causative gene by MutMap Analysis

The "MutMap method" is a method in which bulked segregant analysis (BSA) is combined with whole genome sequencing (WGS) to identify a causative gene region of a mutant (Abe, A. et al., Nat. Biotechnol., 30(2): 174-178 (2012)). As compared with map-based cloning that is conventionally carried out, the MutMap method neither requires marker production nor requires use of a lot of individuals. This makes it possible to greatly reduce labor and time and enables more rapid gene identification.

In the MutMap method, first, a mutant line having a desired character is crossed with a parent variety used for a mutagen treatment, so that an F1 generation is obtained, and an F1 individual is further selfed, so that an F2 generation is obtained. It is considered that a character obtained by a mutation is due to a recessive mutation in many cases. Thus, a phenotype of the F1 generation is supposed to be a wild type, and a phenotype of the F2 generation is supposed to be separated into a wild type and a mutant type at a ratio of 3:1.

In the F2 generation, genetic recombination results in a random combination of a wild-type genome and a genome containing a mutation derived from a mutant, so that genomes that are uniquely combined for each individual occur. Thus, in a case where genomic DNAs derived from an F2 individual showing a mutation-type phenotype are mixed (bulked) and subjected to WGS, an expected value of an appearance frequency of reads having mutations is 0.5 for most regions of a chromosome, whereas an appearance frequency of reads having (i) a mutation causative of a phenotype shown by a mutant and (ii) a mutation in a region around the causal mutation (i) is 1. In the MutMap method, the appearance frequency of the reads having such mutations is set as an "SNP-index", and it is determined that a causative gene (or factor) is present in a region in which SNP-index=1 is continuous.

3-1. Construction of Reference Genome

A genomic DNA was extracted, according to a CTAB method, from a *Nicotiana sylvestris* leaf treated with ethiolate. The genomic DNA was subjected to nucleotide sequence analysis using a next-generation sequencer, so that a genome sequence was constructed. The genome sequence was used as a reference genome. The constructed reference genome consisted of 3,518 scaffolds and had N50 of 48.7 Mb.

For the purpose of prediction of a gene region in the reference genome, RNeasy Plant Mini Kit (QUIAGEN N.V.) was used to extract RNA from a total of 16 kinds of organs (n=3) of *Nicotiana sylvestris*, which were roots (ROOT_1) at 6 weeks after seeding and ROOT_2 at 1 week after topping), a stem at 1 week after flowering, leaves (LEAF_1 at 6 weeks after seeding, LEAF_2 at 1 week after flowering, LEAF_3 during a maturation period (at 40 days after topping), LEAF_4 at the 2nd day of flue curing, and LEAF_5 at the 3rd day of air curing), an axillary bud, flowers (FLOWER_1 (shoot apex), FLOWER_2 (bud), FLOWER_3 at 1 day after flowering, and FLOWER_4 at 4 days after flowering), a germinated seed, and calli (CALLUS_1 derived from a root and CALLUS_2 derived from a leaf). Then, the RNA thus extracted was subjected to RNA-seq by NextSeq500 (Illumina, Inc.).

The gene region was predicted by mapping an RNA-seq read to the reference genome and combining in-silico prediction with CDS region prediction based on a protein sequence of a closely related plant.

3-2. MutMAP Analysis

Genomic DNAs of 25 low-alkaloid F2 individuals derived from SNIC4 and of 18 low-alkaloid F2 individuals derived from SNIC7 were mixed in equal amounts for each line, so that two types of bulk DNA derived from different lines were prepared. The bulk DNA was subjected to paired-end sequence using Hiseq X ten (Illumina, Inc.), so that respective sequence data of 131 Gb and 132 Gb were obtained. The obtained sequence data was used to carry out MutMap analysis.

The genome sequence of *Nicotiana sylvestris* constructed above was used as the reference genome. CLC Genomic Workbench (QUIAGEN N.V.) was used for quality control of a sequence read, mapping of the sequence read to the reference genome, and extraction of a mutation. From a result of the analysis, a candidate region shared by both the lines was extracted, and a gene that has a mutation (SNP-index=1) shared in both the lines in the candidate region was further searched for.

As a result, a gene encoding L-aspartate oxidase (AO) (CDS ID: nsv1s000268m03938) was extracted as an only gene. A genome sequence of an AO gene region of *Nicotiana sylvestris* is represented by SEQ ID NO: 35.

PCR and Sanger sequencing each using primers shown in Table 6 found (i) a stop codon-causing nonsense mutation at a second exon (C to T at position 3563 in SEQ ID NO: 35) for the SNIC4 and (ii) a frame-shift mutation at a seventh exon (deletion of C at position 5141 in SEQ ID NO: 35) for the SNIC7.

Furthermore, sequences of AO genes of the remaining 4 lines that had not been subjected to the MutMAP analysis were checked. As a result, in the AO genes of the 4 lines, the following mutations were found.

SNIC1: a substitution at the second exon, the substitution causing a non-conservative amino acid substitution of neutral amino acid by acidic amino acid (Val to Glu) (T to A at position 3756 in SEQ ID NO: 35);

SNIC2: a nonsense mutation at the seventh exon (C to T at position 5533 in SEQ ID NO: 35);

SNIC5: a splicing mutation at a starting point of a fourth exon (G to A at position 4266 in SEQ ID NO: 35); and SNIC6: a substitution at a third exon, the substitution causing a non-conservative amino acid substitution (Gly to Arg) of neutral amino acid by basic amino acid (G to A at position 4033 in SEQ ID NO: 35)

In view of the above, it has been considered that the mutations of the AO genes are responsible for low alkaloid properties.

multiple splicing variants). Thus, the AO is denoted as "NsAO2". However, the AO2. 1 has a sequence length of only 1107 bp, whereas the NsAO2 has a CDS length as long as 1947 bp. Thus, the AO2. 1 was considered to be an incomplete sequence, and the NsAO2 was considered to be a complete sequence. In a *Nicotiana sylvestris* genome sequence used in Examples of the present application, as described earlier, another AO (ID: nsv1s000268m03841) was present and exhibited a high sequence identity (98%) with the AO1 of Kajikawa et al. Thus, the another AO is denoted as "NsAO1".

A result of RNA-seq analysis carried out with use of RNAs obtained in various organs and stages of *Nicotiana sylvestris* has shown that the NsAO1 was expressed at a low level in any of the organs, whereas the NsAO2 was strongly expressed root-specifically (FIG. 2). Since nicotine biosynthesis is carried out in a root, it has been suggested that the NsAO2 contributes to nicotine biosynthesis.

A coding region nucleotide sequence (CDS) of an NsAO2 gene is represented by SEQ ID NO: 1, and an amino acid sequence of a protein to be encoded is represented by SEQ ID NO: 2. The CDS of the NsAO2 gene was subjected to similar sequence search (BLAST, https://blast.ncbi.nlm.nih.gov/Blast.cgi) against the NCBI database. As a result, genes shown in Table 7 were hit as genes exhibiting a sequence identity of 97% or higher. These genes were considered to be AO2 genes. Other than these genes, genes having a sequence identity in the 93% level were hit but considered to be the AO1. Furthermore, an amino acid sequence of the NsAO2

TABLE 6

| | Sequence (5' to 3') | SEQ ID NO: | Purpose |
|---|---|---|---|
| NsAO2_F | TGCACGACCATAATACTTCAC | 7 | For amplification of NsAO2 genomic DNA sequence |
| NsAO2_R | AAGCTCGTGACCTGTGATATG | 8 | |
| NsAO2_check_F1 | CATGACGTGACACAATTCTAG | 9 | For detection of mutation by Sanger sequencing |
| NsAO2_check_R1 | GTGATATGTTTGACTGGGCAC | 10 | |
| NsAO2_check_F2 | CTAGGTACTTCGATT | 11 | |
| NsAO2_check_R2 | GTATGTGGTTCTCCACTGAATC | 12 | |
| NsAO2_check_F3 | ATGTGTTTCAACACCATTTTG | 13 | |
| NsAO2_check_R3 | ACAACATCAAATCCTTGCTG | 14 | |
| NsAO2_check_F4 | CCAACATCCATTACATACTTAG | 15 | |
| NsAO2_check_R4 | CACCAGTTGCAACCTATAATC | 16 | |
| NsAO2_check_F5 | GAAAGATTTATGCCAATGTATG | 17 | |
| NsAO2_check_R5 | TCTGGGCTTGTGACTGATATC | 18 | |
| NsAO2_check_F6 | CTAGAATTGATAACGGTGCATC | 19 | |
| NsAO2_check_R6 | GAGGTAGACCTAACAATTCCAAC | 20 | |

Example 4: Characterization of AO Sequence of *Nicotiana*

It is known that two AO genes AO1 and AO2 are present in the genus *Nicotiana*. In the document of Kajikawa et al. (2017, Plant physiology, 174: 999-1011), an AO2 gene in a *Nicotiana tabacum* S genome is referred to as "AO2. 1" (gene no. 19078 of Sol Genomics), and an AO2 gene in a *Nicotiana tabacum* T genome is referred to as "AO2. 2" (gene no. 71591 of Sol Genomics). Furthermore, an AO1 gene is referred to as "AO1" (gene no. 57190 of Sol Genomics).

AO (ID: nsv1s000268m03938) identified in Example 3 as a causative gene of a low alkaloid mutation of *Nicotiana sylvestris* was considered to be the AO2 gene because the AO exhibited a sequence identity of 99.9% with the AO2. 1, a sequence identity of 97.6% with the AO2. 2, and a sequence identity of 93.1% to 93.5% with the AO1 (with was similarly subjected to the search. As a result, amino acids shown in Table 8 were hit as amino acids exhibiting a sequence identity of 97% or higher. These amino acids were considered to be amino acid sequences of the AO2. Other than these amino acids, amino acid sequences having a sequence identity in the 90% level were hit but considered to be amino acid sequences of the AO1.

A genome sequence of a tobacco (*N. tabacum*) variety "Tsukuba 1" was analyzed, so that (i) the AO2 (NtAO2-S, ID: nttv1s110m00779, SEQ ID NO. 3) considered to be derived from an S genome and (ii) the AO2 (NtAO2-T, ID: nttv1s507m02461, SEQ ID NO: 4) considered to be derived from a T genome were identified. CDS sequences of the NtAO2-S and the NtAO2-T were subjected to homology search against the NCBI database. As a result, genes shown in Table 9 were hit. These genes each had a homology as high as 97% or higher and were considered to be the AO2 genes. Other than these genes, genes having a homology in the 92% to 93% level were hit but considered to be AO1 genes. Furthermore, amino acid sequences of the NtAO2-S and the NtAO2-T (SEQ ID NO: 5 and SEQ ID NO: 6, respectively) were similarly subjected to the search. As a result, amino acids shown in Table 10 were hit. These amino acids each had a homology as high as 96% or higher and were considered to be amino acid sequences of the AO2. Other than these amino acids, genes having a homology in the 90% to 92% level were hit but considered to be amino acid sequences of the AO1.

FIG. 3 shows a molecular phylogenetic tree of AO amino acid sequences of tobacco plants, the molecular phylogenetic tree having been drawn with use of Genetyx genetic information processing software (GENETYX CORPORATION). Furthermore, FIG. 4 shows expression profiles of the AO genes (NtAO2-S, NtAO2-T, NtAO1-S, and NtAO1-T), the expression profiles having been obtained by using RNA-seq data of RNAs prepared from various organs of tobacco (*N. tabacum*) "Tsukuba 1". As in the case of *Nicotiana sylvestris*, the AO1 (NtAO1-S and NtAO1-T) of the tobacco was constitutively weakly expressed in the entire plant, whereas the AO2 (NtAO2-S and NtAO2-T) was strongly expressed root-specifically.

TABLE 7

| query | Accession number | Biological species | Identity |
|---|---|---|---|
| CDS sequence of NsAO2 (nsv1s00026 8m03938) | XM_009802355 | *Nicotiana sylvestris* | 100% |
| | XR_001648132 | *Nicotiana tabacum* | 99.8% |
| | XM_019402995 | *Nicotiana attenuata* | 97.8% |
| | XM_018766899 | *Nicotiana tomentosiformis* | 97.6% |
| | XM_016633697 | *Nicotiana tabacum* | 97.6% |

TABLE 8

| query | Accession number | Biological species | Identity |
|---|---|---|---|
| Amino acid sequence of NsAO2 (nsv1s0002 68m03938) | XM_00980657 | *Nicotiana sylvestris* | 100% |
| | XR_019258540 | *Nicotiana attenuata* | 99.8% |
| | XM_00958081 | *Nicotiana tomentosiformis* | 97.8% |

TABLE 9

| query | Accession number | Biological species | Identity |
|---|---|---|---|
| CDS sequence of NtAO2-S (nttv1s110 m00779) | XR_001648132 | *Nicotiana tabacum* | 99.9% |
| | XM_009802355 | *Nicotiana sylvestris* | 99.9% |
| | XM_019402995 | *Nicotiana attenuata* | 97.8% |
| | XM_018766899 | *Nicotiana tomentosiformis* | 97.6% |
| | XM_016633697 | *Nicotiana tabacum* | 97.6% |
| CDS sequence of NtAO2-T (nttv1s507 m02461) | XM_018766899 | *Nicotiana tomentosiformis* | 100% |
| | XM_016633697 | *Nicotiana tabacum* | 100% |
| | XM_009802355 | *Nicotiana sylvestris* | 97.6% |
| | XR_001648132 | *Nicotiana tabacum* | 97.5% |
| | XM_019402995 | *Nicotiana attenuata* | 97.5% |

TABLE 10

| query | Accession number | Biological species | Identity |
|---|---|---|---|
| Amino acid sequence of NtAO2-S (nttv1s110m00779) | XP_009800657 | *Nicotiana sylvestris* | 99.9% |
| | XP_019258540 | *Nicotiana attenuata* | 97.4% |
| | XP_009587081 | *Nicotiana tomentosiformis* | 96.9% |
| Amino acid sequence of NtAO2-T (nttv1s507m02461) | XP_009587081 | *Nicotiana tomentosiformis* | 100% |
| | XP_009800657 | *Nicotiana sylvestris* | 97.1% |
| | XP_19258540 | *Nicotiana attenuata* | 96.5% |

The above results have made it clear that only a mutation of the NsAO2 (with no mutation in the NsAO1) is responsible for a phenotype (decrease in alkaloid content) exhibited by the obtained plant. Sequence data of bulk DNA (described earlier) also further supported the above results (that is, no mutation was present in the NsAO1 that was present in genomes of SNIC4 and SNIC7).

Example 5: Production of Recombinant of *Nicotiana tabacum* and *Nicotiana sylvestris* with Function of AO2 Suppressed and Analysis of Alkaloid Content Thereof (5-1) Operation of Recombination of Plant RNeasy Plant Mini Kit (QUIAGEN N.V.) was used to extract RNA from a root of a seedling of *Nicotiana sylvestris*. Then, PrimeScript (trademark) RT reagent Kit (Takara Bio Inc.) was used to synthesize cDNA. With use of the cDNA as a template and primers shown in Table 11, two types of gene fragments (trigger sequences for RNAi) of NsAO2 were amplified. These gene fragments are trigger sequences for RNAi that were designed to specifically target the NsAO2 in *Nicotiana sylvestris* and both NtAO2-S and NtAO2-T in *Nicotiana tabacum*. PrimeSTAR (registered trademark) Max DNA Polymerase (Takara Bio Inc.) was used for PCR. A CACC sequence for use in cloning (described later) was added to a 5' end of a primer.

PCR products were purified by using MiniElute PCR Purification kit (QUIAGEN N.V.). Thereafter, the purified PCR products were cloned in a vector pENTR (trademark)/D-TOPO (registered trademark) (Life Technologies Corporation). After a nucleotide sequence of an insert was checked, GateWay (registered trademark) LR Clonase (registered trademark) II Enzyme mix (Thermo Fisher Scientific Inc.) was used to clone the insert into an RNAi vector pSP231 (see International Publication No. WO 2011/102394). The vector pSP231, which is a binary vector based on pHellsgates12 (see Wesley et al., Plant J., 27: 581-590 (2001)), includes a green-fluorescent protein (GFP) gene. In the pSP231, an RNAi sequence having a pdk/cat intron located between inverted repeat sequences of a trigger sequence) is driven by a cauliflower mosaic virus 35SRNA gene promotor. After the cloning into the pSP231, an RNAi trigger sequence and its orientation were checked. As a result, a final RNAi construct was obtained.

TABLE 11

Primer sequence used to prepare RNAi vector

| Primer name | Sequence (5' to 3') | SEQ ID NO: | Length (bp) of target sequence |
|---|---|---|---|
| NsAO2_RNAi_F1 | CACCTGAGGAATAGCTATGGAAATAAAG | 21 | 222 |
| NsAO2_RNAi_R1 | TGAAATCGAAGTACCTAGTAACT | 22 | |
| NsAO2_RNAi_F2 | CACCAGAGAGTCGTGGGCTTCACTAC | 23 | 136 |
| NsAO2_RNAi_R2 | CTAACTTATCGGCTGCGCGTG | 24 | |

By introducing the obtained RNAi construct into *Nicotiana tabacum* and *Nicotiana sylvestris*, it is possible to suppress a function of the AO2 genes (NtAO2-S and NtAO2-T) of *Nicotiana tabacum* or of the AO2 genes of *Nicotiana sylvestris*.

An RNAi construct having a trigger sequence amplified with use of a set of primers (SEQ ID NOs: 21 and 22) was introduced into *Agrobacterium* LBA4404 by electroporation. In a resulting transformant *Agrobacterium*, the presence of the RNAi trigger sequence was confirmed by PCR, and then the *Agrobacterium* was used to transform a variety "Tsukuba 1" (*N. tabacum*) (hereinafter referred to as an "NtAO2-RNAi line"). As a control, a transformant of Tsukuba 1 with use of the *Agrobacterium* (hereinafter referred to as an "Empty line") into which a pSP231 vector containing no trigger sequence had been introduced was produced.

A section of a leaf was infected with the *Agrobacterium*, and was cultured in a Linsmaier and Skoog (LS) medium containing kanamycin (50 μg/mL), so that calli were obtained. From the obtained calli, redifferentiated individuals which were kanamycin-resistant were obtained. Among the redifferentiated individuals, individuals in each of which GFP fluorescence had been successfully observed throughout a leaf were grown in a plant box and transplanted into a 9-cm pot when the individuals were sufficiently grown.

During the transplantation, leaves and roots of each of the individuals were sampled and stored at −80° C. after being frozen with liquid nitrogen.

(5-2) Selection of Desired Recombinant

Next, among the transplanted individuals, an individual in which a function of the NsAO2 had been suppressed by the RNAi was determined. For the determination, NsAO2 mRNA in the sampled leaves and roots was quantitatively determined by real-time PCR as below.

RNeasy Plant Mini Kit (QUIAGEN N.V.) was used to extract total RNA from the sampled leaves and roots. By reverse transcription with use of PrimeScript (trademark) RT reagent kit with gDNA Eraser (Takara Bio Inc.), from 0.5 μg of the extracted total RNA, a genomic DNA was removed, and cDNA was synthesized. With use of 1 of the synthesized cDNA as a template and TaqMan (registered trademark) Fast Advanced Master Mix (Thermo Fisher Scientific Inc.), real-time PCR was carried out in a 10-μL reaction system. A transcript amount of a targeted gene was determined by a delta-delta Ct method using elfa (elongation Factor-1 α) as a reference gene.

Table 12 shows sequences of primers and probes used to detect genes. The primers and probes used to detect AO1 and AO2 are partially designed for a nucleotide sequence of a 3' untranslated region (UTR) of each gene.

TABLE 12

Primer and probe sequences for real-time PCR

| Targeted gene | Primer/probe | Sequence (5' to 3') | SEQ ID NO: |
|---|---|---|---|
| AO | Fw primer | GCTGCTGAGTGTCTCCGC | 38 |
| | Rv primer | TCCACCACACATGTAGTGAGC | 39 |
| | Probe | (FAM)TGGGTTAGACATAACACAGCAGCCGATTCC(TAMRA) | 40 |
| AO1 | Fw primer | GAGGTTGCCAACAATCATTTTTC | 41 |
| | Rv primer | TGCGCTTGACAAGTTTTAGCA | 42 |
| | Probe | CTCACGGCAATTACACAGGCAGCAGATAT | 43 |
| AO2 | Fw primer | AGATATCTCTTACCTATTTGCCATTCTTC | 44 |
| | Rv primer | CCATACCCCTTCCGATAGATACAC | 45 |
| | Probe | (FAM) TGCCAAAACATCTCCAGTGCAGGACA (TAMRA) | 46 |
| elfα | Fw primer | CTAAGGGTGCTGCCAGCTTT | 47 |
| | Rv primer | GTCAAGCACTGGAGCATATCCA | 48 |
| | Probe | (VIC)ATCATGAACCATCCAGGACAGATTGG(TAMRA) | 49 |

Six individuals having such amounts of transcripts as below were determined on the basis of a result of real-time PCR (FIG. 5). FIG. 5 shows a transcript amount of each line as a value relative to a transcript amount of Empty-12 (a value 1 on the vertical axis). In FIG. 5, "AO2-(number)" indicates an NtAO2-RNAi line, "Empty-(number)" indicates a control line, and an error bar indicates a measurement error (a standard error among 3 replicated tests).

Roots: AO (both AO1 and AO2) and AO2 transcripts in much smaller amounts as compared with controls Leaves: AO and AO1 transcripts in amounts equivalent to the amounts of the controls The above 6 individuals were selected as individuals in each of which only the AO2 transcript was decreased and the AO1 transcript was not decreased. The following description will discuss the reason why transcription profiles of the AO1 and the AO2 in the above 6 individuals were thus determined. Hereinafter, "AO" refers to "both AO1 and AO2", "AO1" refers to "AO1 only," and "AO2" refers to "AO2 only," unless otherwise specified.

First of all, AO expression profiles in a tobacco plant are as follows (see FIG. 4 and Non-Patent Literature 6).

Expression of AO1: Relatively low-level expression constant in each tissue

Expression of AO2: High-level expression specific to roots and extremely low-level expression in other tissues That is, in a case where transcripts (the AO and the AO2) in roots of the tobacco plant are quantitatively determined, it is possible to determine a decrease in AO2 transcript amount in the tobacco plant.

Table 13 partially shows measured values for preparing the graph of FIG. 4.

TABLE 13

AO1 and AO2 transcript amounts in roots and leaves of Tsukuba 1 (FPKM values obtained by RNA-seq analysis)

| | Leaf 1 | Leaf 2 | Leaf 3 | Leaf 4 | Root 1 | Root 2 |
|---|---|---|---|---|---|---|
| NtAO1-S | 8.2 | 7.2 | 8.4 | 8.6 | 2.2 | 3.8 |
| NtAO1-T | 15.5 | 7.7 | 9.0 | 6.7 | 3.2 | 2.4 |
| NtAO2-S | 0.0 | 0.0 | 0.0 | 0.0 | 195.2 | 67.3 |
| NtAO2-T | 0.0 | 0.0 | 0.0 | 0.0 | 153.2 | 60.2 |

Table 13 shows that a sufficient decrease in AO2 transcript in the roots of the tobacco plant means a sufficient decrease in AO2 transcript in the tobacco plant (entirety) (lower right of FIG. 5). Table 13 also shows that maintenance of the AO1 transcript in the leaves of the tobacco plant (in a recombinant as compared with a control) means that an off-target effect (a non-specific decrease in AO1 transcript by the above RNAi construct) is substantially not present (upper right of FIG. 5). Furthermore, determination of an AO transcript amount (amounts of both the AO1 transcript and the AO2 transcript) in the roots and leaves can reinforce the above meaning (lower left and upper left of FIG. 5). This is because, on the basis of AO1 and AO2 transcription patterns that are shown in Table 13 and that vary from tissue to tissue, the AO transcript amount of the leaves (with almost no AO2 transcript) substantially represents the AO1 transcript amount, and the AO transcript amount of the roots (most of which are occupied by the AO2 transcript) substantially represents the AO2 transcript amount.

(5-3) Evaluation of Alkaloid Content in Selected Recombinant and Control

The obtained 6 individuals of NtAO2-RNAi lines and 3 individuals of Empty lines were potted in a 9-cm pot and then grown in a phytotron (at 28° C. during a light period of 16 h and at 22° C. during a dark period of 8 h) for approximately 1 month. Thereafter, the condition of the phytotron was changed to a low temperature/short-day condition (at 18° C. for a day length of 8 h), and the individuals were grown. After the individuals were grown at the low temperature/short day condition, 2 to 4 medium leaves were collected during flowering time, cured at 70° C. for 16 hours, ground, and subjected to minor alkaloid analysis. Table 14 shows results of the analysis.

TABLE 14

Result of minor alkaloid analysis

| | Nicotine (%) | Nor- nicotine (%) | Anabasine (%) | Anatabine (%) | Myosmine (%) |
|---|---|---|---|---|---|
| NtAO2-RNAi-2 | ND | 0.008 | ND | ND | ND |
| NtAO2-RNAi-6 | ND | 0.007 | ND | ND | ND |
| NtAO2-RNAi-10 | ND | ND | ND | ND | ND |
| NtAO2-RNAi-11 | ND | ND | ND | ND | ND |
| NtAO2-RNAi-12 | ND | ND | ND | ND | ND |
| NtAO2-RNAi-16 | ND | ND | ND | ND | ND |
| Empty-5 | 0.21 | 0.010 | 0.003 | 0.023 | ND |
| Empty-12 | 0.22 | 0.010 | 0.003 | 0.019 | ND |
| Empty-14 | 0.05 | 0.030 | 0.002 | 0.013 | ND |

As shown in Table 14, 0.08% to 0.23% (0.8 mg/g to 2.3 mg/g cured leaves) of nicotine and nornicotine were detected in samples of the controls. In samples of the NtAO2-RNAi lines, a nicotine content was less than or equal to a detection limit (ND), and nornicotine was detected in 2 individuals of the 6 individuals (0.008% and 0.007%). As described above, it has been demonstrated that suppression of a function of the AO2 in a tobacco plant shows a decrease in alkaloid content.

Note here that Non-Patent Literature 9 indicates that in an individual in which an AO2 (denoted as AO1 in Non-Patent Literature 9) transcript was decreased (hereinafter referred to as "D9_AO2-RNAi"), lower leaves have developed spots and have shown early senescence. However, it has been confirmed that all the individuals of the NtAO2-RNAi lines and the controls were normally grown (no phenomena disclosed in Non-Patent Literature 9 have been observed).

In leaves of the D9_AO2-RNAi, the AO transcript amount has been decreased (to 1.4 at maximum, and to 10.9 at minimum) as compared with a wild-type plant (FIG. 5 of Non-Patent Literature 9). However, as demonstrated in Table 13, the AO transcript in a leaf is substantially free of the AO2 transcript (substantially no AO2 transcript has occurred therein). Thus, a decrease in AO transcript amount in the D9_AO2-RNAi substantially reflects a decrease in AO1 transcript amount.

Tobacco plants produced in the present Examples showed a decrease in AO2 transcript amount and maintenance of the AO1 transcript amount. The tobacco plants were normally grown (did not show the above-described phenomena disclosed in Non-Patent Literature 9). The tobacco plant showed an alkaloid content having been greatly decreased as compared with the controls. That is, it has been found that the tobacco plant in which AO2 expression is specifically suppressed exhibits characters (a decrease in alkaloid content and normal growth) useful for tobacco cultivation.

Example 6: Production of Tobacco Mutant with Function of AO2 Suppressed

A tobacco mutant having a mutation in an AO2-S or an AO2-T was obtained.

For 2000 tobacco mutant lines, nucleotide sequences of NtAO2-S and NtAO2-T gene regions were analyzed, and mutations were identified. Specifically, mutant selfed progeny seeds (M2 seeds) obtained for each M1 generation of 2000 individuals of tobacco mutants produced by carrying out an EMS treatment for seeds of a tobacco variety Tsukuba 1 were sown, DNA extracted from seedlings of 8 individuals per each grown line was bulked (Tajima et al., 2011 Annual Meeting of Phytopathological Society of Japan, p. 234, production of tobacco mutant panel), and nucleotide sequences were analyzed. Genome sequences of the NtAO2-S and NtAO2-T gene regions are represented by SEQ ID NO: 36 and SEQ ID NO: 37, respectively.

As a result, 11 lines each having a nonsense mutation, or a frame-shift mutation or a splicing mutation in the NtAO2-S or the NtAO2-T were found in each of the NtAO2-S the NtAO2-T (22 lines in total) (Tables 15 and 16). In all these lines, an AO2 gene in the other (a T genome in a case where a mutation is present in an S genome, or the S genome in a case where a mutation is present in the T genome) of genomes had no mutation and remained wild type. That is, the NtAO2-T gene had no mutation in the line having a mutation in the NtAO2-S gene, and the NtAO2-S gene had no mutation in the line having a mutation in the NtAO2-T gene. Three mutants were selected for each of both the genes, and seeds of their lines were sown, so that DNA was extracted while the lines were in a seedling stage. PCR was carried out with use of this DNA as a template and primers shown in Table 17, and an individual having homozygous mutations was selected. KOD One (registered trademark) PCR Master Mix (TOYOBO CO., LTD.) was used for PCR.

TABLE 15

Mutant line having mutation in NtAO2-S

| Type of mutation | Position in SEQ ID NO: 36 | Wild-type nucleotide | Mutation-type nucleotide |
| --- | --- | --- | --- |
| NtAO2-s-1 | Nonsense mutation | Position 3792 | C | T |
| NtAO2-s-2 | Nonsense mutation | Position 3792 | C | T |
| NtAO2-s-3 | Splicing mutation | Position 4178 | G | A |
| NtAO2-s-4 | Nonsense mutation | Position 3504 | C | T |
| NtAO2-s-5 | Splicing mutation | Position 4267 | G | A |
| NtAO2-s-6 | Frame-shift mutation | Position 5288 | G | — |
| NtAO2-s-7 | Nonsense mutation | Position 5648 | G | A |
| NtAO2-s-8 | Nonsense mutation | Position 5747 | G | A |
| NtAO2-s-9 | Nonsense mutation | Position 5852 | G | A |
| NtAO2-s-10 | Nonsense mutation | Position 6041 | G | A |

TABLE 16

Mutant line having mutation in NtAO2-T

| Type of mutation | Position in SEQ ID NO: 37 | Wild-type nucleotide | Mutation-type nucleotide |
| --- | --- | --- | --- |
| NtAO2-t-1 | Nonsense mutation | Position 3124 | C | T |
| NtAO2-t-2 | Nonsense mutation | Position 3288 | G | A |
| NtAO2-t-3 | Splicing mutation | Position 4078 | G | A |
| NtAO2-t-4 | Splicing mutation | Position 4078 | G | A |
| NtAO2-t-5 | Nonsense mutation | Position 3304 | C | T |
| NtAO2-t-6 | Splicing mutation | Position 4810 | G | A |
| NtAO2-t-7 | Splicing mutation | Position 5032 | G | A |
| NtAO2-t-8 | Nonsense mutation | Position 5361 | C | T |
| NtA02-t-9 | Nonsense mutation | Position 5605 | G | A |
| NtAO2-t-10 | Nonsense mutation | Position 5813 | G | A |
| NtAO2-t-11 | Nonsense mutation | Position 5988 | C | T |

As a result, three lines each having a mutation in the NtAO2-S gene were obtained. In two of those lines, a single homozygous nonsense mutation (in which a codon encoding the 150th glutamine (Q) of an NtAO2-S protein had been changed to a termination codon by a nucleotide substitution (C to T at position 3792 in SEQ ID NO: 36)) occurred in the NtAO2-S gene (NtAO2-s-1 and NtAO2-s-2).

In the remaining one of the lines, a single homozygous splicing mutation (in which a 5' end of a third intron of the NtAO2-S gene was not normally spliced by a nucleotide substitution (G to A at position 4178 in SEQ ID NO: 36)) occurred in the NtAO2-S gene (NtAO2-s-3).

Furthermore, three lines each having a mutation in the NtAO2-T gene were obtained. In a first line, a single homozygous nonsense mutation (in which a codon encoding the 42nd glutamine (Q) of an NtAO2-T protein had been changed to a termination codon by a nucleotide substitution (C to T at position 3124 in SEQ ID NO: 37)) occurred in the NtAO2-T gene (NtAO2-t-1).

In a second line, a single homozygous nonsense mutation (in which a codon encoding the 48th tryptophan (W) of the NtAO2-T protein had been changed to a termination codon by a nucleotide substitution (G to A at position 3288 in SEQ ID NO: 37)) occurred in the NtAO2-T gene (NtAO2-t-2).

In a third line, a single homozygous splicing mutation (in which a 3' end of a third intron of the NtAO2-T gene was not normally spliced by a nucleotide substitution (G to A at position 4078 in SEQ ID NO: 37)) occurred in the NtAO2-T gene (NtAO2-t-3).

TABLE 17

| | Wild-type nucleotide | Mutation-type nucleotide | Type of mutation | Primer sequence (5' to 3') Forward | Primer sequence (5' to 3') Reverse |
|---|---|---|---|---|---|
| NtAO2-s-1 | C | T | Nonsense mutation | TAAGAGACAGGCGAGGAACAATCAAATCTA (SEQ ID NO: 25) | TAAGAGACAGGGGAAATAGTCTCCAAATTA (SEQ ID NO: 26) |
| NtAO2-S-2 | C | T | Nonsense mutation | Same as above | Same as above |
| NtAO2-S-3 | G | A | Splicing mutation | TAAGAGACAGGCAGAGAGATTGAAAGAGCC (SEQ ID NO: 27) | TAAGAGACAGCTGAATAGTTCAATTGCGAC (SEQ ID NO: 28) |
| NtAO2-t-1 | C | T | Nonsense mutation | TAAGAGACAGAGGATGCGGACAGTTACAC (SEQ ID NO: 29) | TAAGAGACAGGCCATGGATAATAGTTTGAC (SEQ ID NO: 30) |
| NtAO2-t-2 | G | A | Nonsense mutation | TAAGAGACAGTAAACATCGCGCTAATAATC (SEQ ID NO: 31) | TAAGAGACAGTAGACTTCCAGTTTGTCTTG (SEQ ID NO: 32) |
| NtAO2-t-3 | G | A | Splicing mutation | TAAGAGACAGCAGAGAGATAGAAAGAGCTC (SEQ ID NO: 33) | TAAGAGACAGCAAGTAAGAGCGCAGAAGC (SEQ ID NO: 34) |

Tag sequences to be used to detect mutations later with use of a next generation sequencer are underlined.

An effect of a decrease in nicotine content was investigated for each of mutants of the NtAO2-S and the NtAO2-T of a tobacco (*N. tabacum*).

Plants (mutants) were grown in a greenhouse and three leaves during flowering time were sampled. After having been cured at 70° C. for 8 hours, the leaves were ground and then subjected to minor alkaloid analysis.

As a result, 2 tobacco mutant lines in each of which the AO2 gene was not disrupted had respective nicotine contents of 0.34% and 0.41% (0.38% on average). In contrast, 2 AO2-S mutant lines (NtAO2-s-2 and NtAO2-s-1) had respective nicotine contents of 0.10% and 0.16% (0.13% on average and 34% of a nicotine content of a control), and an AO2-T mutant (NtAO2-t-2) had a nicotine content of 0.18% (47% of the nicotine content of the control). Furthermore, a tobacco mutant in which the AO2 gene was not disrupted had an anatabine content of 0.012% to 0.016%. In contrast, in AO2-S and AO2-T single mutants, the anatabine content was reduced approximately by half to 0.004% to 0.009%. Both a nornicotine content and an anabasine content were each less than or equal to a limit of quantitative determination. Typically, in order to obtain a phenotype by causing a mutation in a gene of *Nicotiana tabacum*, it is necessary to cause mutations in both a gene derived from an S genome and a gene derived from a T genome (for example, Liedschulte et al. (2017) Plant Cell Environ. 40: 364-377). However, the present invention shows that a mutation of a single gene (the NtAO2-S or the NtAO2-T) has an effect of reducing nicotine.

This shows that a single mutation of either one of the AO2-S and the AO2-T, which are 2 AO2 genes present in a tobacco (*N. tabacum*), reduces the nicotine content approximately by half. It is also shown that a mutant having both AO2-S and AO2-T mutations is highly likely to have an extremely low content of alkaloid including nicotine.

The NtAO2-s-1 and the NtAO2-t-1 were grown in a greenhouse (24° C.) and crossed, so that an F1 generation was obtained (NtAO2-F1-1). The NtAO2-s-2 and the NtAO2-t-2 were grown in a greenhouse and crossed, so that an F1 generation was obtained (NtAO2-F1-2). By growing the F1 generations in the greenhouse and selfing the F1 generations, 2 F2 generation lines derived from different mutant lines were obtained (NtAO2-F2-1 and NtAO2-F2-2).

Sequences around mutations were amplified by sowing the 2 F2 generation lines, extracting DNA from a seedling, and carrying out PCR using the primers of Table 17. Sequences (a p7 sequence, a p5 sequence, and a bar-code sequence for each individual) used in sequencing of an amplification product with use of iSeq 100 (Illumina, Inc.) were subjected to PCR to add the sequences to the amplification product. Then, the amplification product to which the sequences were added was subjected to sequencing carried out with use of iSeq 100 (Illumina, Inc.), so that a genotype of each individual was determined.

As a result, 2 sets of an individual (NtAO2-sstt) having homozygous mutations in the NtAO2-S and the NtAO2-T and an individual (NtAO2-SSTT) having no mutations in both the genes were obtained. After having been potted in a 9-cm pot, these individuals were subjected to sequence determination by PCR and Sanger sequencing, so that genotypes were determined (Table 18).

TABLE 18

Numbers of individuals of genotypes of F2 generations

| | NtAO2-sstt | NtAO2-SSTT |
|---|---|---|
| NtAO2-F2-1 | 5 | 6 |
| NtAO2-F2-2 | 6 | 5 |

The individuals were each transplanted into a 1/5000 Wagner pot and subjected to topping during flowering time. After 3 weeks of the topping, 2 leaves (without additional fertilization) were collected from each of the individuals. Among the individuals from which the 2 leaves had been collected, three individuals exhibiting relatively good growth were selected for each genotype and subjected to additional fertilization. Specifically, all leaves were removed while three leaves from the top were left as they were, and 50 g of Burley S625, a chemical fertilizer partially blended with organic fertilizer for tobacco (Seiwa Fertilizer Ind. Co., Ltd.) was applied. After approximately 3 weeks, all the three leaves (with additional fertilization) were collected from each of the individuals. The collected leaves (without additional fertilization) and the collected leaves (with additional fertilization) were subjected to minor alkaloid analysis by being cured at 70° C. for 16 hours and ground after removing mid-ribs.

As a result of the analysis, the individual (NtAO2-sstt) having mutations in 4 alleles of the AO2 showed a nicotine content (FIG. 6 and Table 19) and a total alkaloid content (Table 19) each of which was greatly decreased as compared with the individual (NtAO2-SSTT) having no mutations in the 4 alleles.

In each of the two sets, a great difference (with 1% level of significant difference shown in a t-test) was observed in nicotine content in leaves without additional fertilization between (a) the individual (NtAO2-sstt) having mutations in all the alleles of the AO2 and (b) the individual (NtAO2-SSTT) having no mutations in the alleles. As shown in the left panel of FIG. 6, regarding nicotine contents (average±SD) in the set NtAO2-F2-1, the individual (NtAO2-sstt) having the mutations had a nicotine content that was less than or equal to a detection limit, and the individual (NtAO2-SSTT) having no mutations had a nicotine content of 0.18%±0.099%. As shown in the right panel of FIG. 6, regarding nicotine contents (average±SD) in the set NtAO2-F2-2, the individual (NtAO2-sstt) having the mutations had a nicotine content of 0.01%±0.02%, and the individual (NtAO2-SSTT) having no mutations had a nicotine content of 0.56%±0.286%.

Table 19 shows a nicotine content and a total alkaloid content (a sum of a nicotine content, a nornicotine content, an anatabine content, an anabasine content, and a myosmine content) in the leaves with additional fertilization.

As shown in Table 19, the leaves with additional fertilization in the NtAO2-sstt had a nicotine content of 0.01% to 0.02%. The leaves with additional fertilization in the NtAO2-SSTT had a nicotine content of 1.05% to 3.62%. This value is similar to 1.5% to 4.5% (see Non-Patent Literature 1), which is a nicotine content of a typical field-grown individual. Thus, the NtAO2-sstt showed an extremely low nicotine content and an extremely low total alkaloid content (each of which is a content of less than 1% relative to a content of a genotype SSTT).

All the individuals had a variation (without any difference based on a genotype) in plant height or the number of leaves produced, but were substantially normally grown. Occurrence of spots not based on a mutation of the AO2 gene was observed in some of the individuals as below.

In the NtAO2-F2-1, occurrence of spots or early senescence in the leaves was not observed. In the NtAO2-F2-2, occurrence of spots with similar appearance was observed in the leaves of both the sstt and the SSTT (independently of a mutation of the AO2 gene). Thus, the occurrence of the spots is considered to be caused by a mutation that is shared by the individuals of the line NtAO2-F2-2 and that is different from the mutation of the AO2 gene. Furthermore, the above-described appearance of the spots was clearly different from appearance of spots observed in a mutant (in which a function of the AO1 is suppressed) of Comparative Examples described later.

A tobacco plant of the present Examples, which tobacco plant had mutations in all the alleles of the AO2 and had no mutations in all the alleles of the AO1, was normally grown.

TABLE 19

Alkaloid contents of SSTT individuals and sstt individuals of NtAO2-F2-1 and NtAO2-F2-2 after additional fertilization

| Line | Genotype | Individual number | Nicotine (%) | Nornicotine (%) | Anabasine (%) | Anatabine (%) | Myosmine (%) |
|---|---|---|---|---|---|---|---|
| NtAO2-F2-1 | SSTT | 54 | 2.70 | 0.08 | 0.02 | 0.27 | N.D. |
| | | 137 | 3.62 | 0.11 | 0.03 | 0.37 | N.D. |
| | | 160 | 2.07 | 0.06 | 0.02 | 0.15 | N.D. |
| | sstt | 53 | 0.02 | N.D. | N.D. | N.D. | N.D. |
| | | 78 | 0.02 | N.D. | N.D. | N.D. | N.D. |
| | | 174 | 0.01 | N.D. | N.D. | N.D. | N.D. |
| NtAO2-F2-2 | SSTT | 43 | 1.05 | 0.05 | 0.01 | 0.09 | N.D. |
| | | 119 | 1.87 | 0.07 | 0.02 | 0.19 | N.D. |
| | | 145 | 3.22 | 0.11 | 0.03 | 0.39 | N.D. |
| | sstt | 1 | 0.01 | N.D. | N.D. | N.D. | N.D. |
| | | 72 | 0.01 | N.D. | N.D. | N.D. | N.D. |
| | | 102 | 0.01 | N.D. | N.D. | N.D. | N.D. |

"ND" indicates "less than or equal to a detection limit".

Specifically, regarding samples having been subjected to additional fertilization, in the NtAO2-SSTT serving as a control, the NtAO2-F2-1 had a nicotine content of 2.07% to 3.62%, and the NtAO2-F2-2 had a nicotine content of 1.05% to 3.22%. In contrast, in the NtAO2-sstt, the NtAO2-F2-1 had a nicotine content of 0.01% to 0.02%, and all 3 individuals of the NtAO2-F2-2 had a nicotine content of 0.01% (Table 19). The NtAO2-F2-1 serving as a control had a total alkaloid content (a sum of a nicotine content, a nornicotine content, an anatabine content, an anabasine content, and a myosmine content) of 2.29% to 4.13%, and the NtAO2-F2-2 had a total alkaloid content of 1.20% to 3.74%. In contrast, in the NtAO2-sstt, the NtAO2-F2-1 had a total alkaloid content of 0.01% to 0.02%, and all 3 individuals of the NtAO2-F2-2 had a total alkaloid content of 0.01% (Table 19).

The tobacco plant showed an alkaloid content having been greatly decreased as compared with the controls. That is, it has been found that the tobacco plant that expresses no functional AO2 protein exhibits characters (a decrease in alkaloid content and normal growth) useful for tobacco cultivation.

Comparative Example 1: Tobacco Mutant with Function of AO1 Suppressed

A tobacco mutant that has a mutation in an AO1-S or an AO1-T was produced as below.

An NtAO1-S mutant (15 lines) having a mutation in an NtAO1-S and an NtAO1-T mutant (12 lines) having a mutation in an NtAO1-T were identified by analyzing 2000 tobacco mutant lines as in the case of Example 6. It has been confirmed that the NtAO1-S mutant has no mutation in the NtAO1-T and that the NtAO1-T mutant has no mutation in the NtAO1-S. 3 NtAO1-S mutant lines (lines 1 to 3 in Table 18) and 3 NtAO1-T mutant lines were selected, seeds thereof were sown, and DNA was extracted from seedlings thereof. With use of the DNA as a template and PCR using a set of primers, lines having homozygous mutations were determined. KOD One (registered trademark) PCR Master Mix (TOYOBO CO., LTD.) was used in PCR. Table 20 lists names of mutants (lines 1-3: NtAO1-S mutant lines, lines 4-6: NtAO1-T mutant lines), types of mutations, and primers used to determine the mutations (for PCR).

In the NtAO1-t-2, a single homozygous nonsense mutation occurred in the NtAO1-T gene. The nonsense mutation is a nucleotide substitution (C to T) that occurs in a codon encoding 61st glutamine (Q) in the wild-type NtAO1-T protein.

In the NtAO1-t-3, a single homozygous splicing mutation (a nucleotide substitution that causes a splicing anomaly) occurred in the NtAO1-T gene. The splicing mutation is a nucleotide substitution (G to A) that occurs at a 3' end terminus of a second exon of the NtAO1-T gene.

TABLE 20

Primer sequences used to determine mutations of AO1 mutants

| | Wild-type nucleotide | Mutation-nucleotide type | Type of mutation | Primer sequence (5' to 3') | |
|---|---|---|---|---|---|
| | | | | Forward | Reverse |
| NtAO1-s-1 | C | T | Nonsense mutation | TAAGAGACAGACC TCAGAATTGGGTG TGCC (SEQ ID NO: 50) | TAAGAGACAGGAT AGAGAGGAGAGAT AGGC (SEQ ID NO: 51) |
| NtAO1-s-2 | C | T | Nonsense mutation | TAAGAGACAGATG CTCTAGAAGTTGC AAAG (SEQ ID NO: 52) | TAAGAGACAGTTC TCCCGTGCCTTCT CAC (SEQ ID NO: 53) |
| NtAO1-s-3 | G | A | Nonsense mutation | TAAGAGACAGTTTT CCATGTAAACATTT GC (SEQ ID NO: 54) | TAAGAGACAGTGA CATCCCTCATAAAT GAA (SEQ ID NO: 55) |
| NtAO1-t-1 | G | A | Nonsense mutation | TAAGAGACAGGGG AGTGCTAATCTGAT ATG (SEQ ID NO: 56) | TAAGAGACAGGGC AATAGAAAGAAGA TAATAC (SEQ ID NO: 57) |
| NtAO1-t-2 | C | T | Nonsense mutation | TAAGAGACAGTTAT TCCTCCAATGAGA ACG (SEQ ID NO: 58) | TAAGAGACAGTAC CAATCACCGCGAA ATCG (SEQ ID NO: 59) |
| NtAO1-t-3 | G | A | Splicing mutation | TAAGAGACAGGTT TAGTATACTCTTTT GAAG (SEQ ID NO: 60) | TAAGAGACAGCTA TAGCAAAATTTTCA CAC (SEQ ID NO: 61) |

*Tag sequences to be used to detect mutations later with use of a next-generation sequencer are underlined.

In the NtAO1-s-1, a single homozygous nonsense mutation (a change of one codon in an ORF to a termination codon) occurred in an NtAO1-S gene. The nonsense mutation is a nucleotide substitution (C to T) that occurs in a codon encoding 41st glutamine (Q) in a wild-type NtAO1-S protein.

In the NtAO1-s-2, a single homozygous nonsense mutation occurred in the NtAO1-S gene. The nonsense mutation is a nucleotide substitution (C to T) that occurs in a codon encoding 146th glutamine (Q) in the wild-type NtAO1-S protein.

In the NtAO1-s-3, a single homozygous nonsense mutation occurred in the NtAO1-S gene. The nonsense mutation is a nucleotide substitution (G to T) that occurs in a codon encoding 277th glycine (G) in the wild-type NtAO1-S protein.

In the NtAO1-t-1, a single homozygous nonsense mutation occurred in an NtAO1-T gene. The nonsense mutation is a nucleotide substitution (G to A) that occurs in a codon encoding 44th tryptophan (W) in a wild-type NtAO1-T protein.

The above mutants were grown in a greenhouse. An F1 generation was obtained by crossing the NtAO1-s-1 and the NtAO1-t-1 (NtAO1-F1-1). An F1 generation was obtained by crossing the NtAO1-s-2 and the NtAO1-t-2 (NtAO1-F1-2). By growing the F1 generations and selfing the F1 generations, 2 F2 generation lines derived from different mutant lines were obtained (NtAO2-F2-1 and NtAO2-F2-2).

Sequences around mutations were amplified by sowing the 2 F2 generation lines, extracting DNA from 192 temporary seedling individuals, and carrying out PCR using the primers of Table 20. Sequences (a p7 sequence, a p5 sequence, and a bar-code sequence for each individual) used in sequencing of an amplification product with use of iSeq 100 (Illumina, Inc.) were subjected to PCR to add the sequences to the amplification product. Then, the amplification product to which the sequences were added was subjected to sequencing carried out with use of iSeq 100 (Illumina, Inc.), so that a genotype of each individual was determined.

As a result, an individual having a genotype such that the individual has the above-described homozygous mutations in the NtAO1-S and NtAO1-T genes was absent in all individuals of the NtAO1-F2-1 and the NtAO1-F2-2. A functionally disrupted mutant of an AO of *Arabidopsis thaliana* (corresponding to an AO1 of a tobacco plant) has been reported to be embryonically lethal (Katoh, A. et al. (2006) Plant Physiology 141: 851-857). Thus, mutants of the AO1 (AO1-S and AO1-T) are considered to be lethal also in tobacco.

Subsequently, among the individuals of the NtAO1-F2-1 and the NtAO1-F2-2, individuals showing the following genotypes (1) to (5) (a plurality of individuals for each genotype) were potted in a 9-cm pot, subjected to genotype determination by PCR and Sanger sequencing, and then grown in a greenhouse (at 24° C.) (Table 20). Table 21 shows genotypes and the numbers of the grown individuals.

(1) an individual having a homozygous mutation in the NtAO1-S gene and having no mutation in the NtAO1-T gene (NtAO1-ssTT)
(2) an individual having no mutation in the NtAO1-S gene and having a homozygous mutation in the NtAO1-T gene (NtAO1-SStt)
(3) an individual having a heterozygous mutation in the NtAO1-S gene and having a homozygous mutation in the NtAO1-T gene (NtAO1-Sstt)
(4) an individual having no mutation in the NtAO1-S gene and having a heterozygous mutation in the NtAO1-T gene (NtAO1-SStT), and
(5) an individual having no mutations in the NtAO1-S gene and the NtAO1-T gene (NtAO1-SSTT)

TABLE 21

| Numbers of individuals of genotypes | | | | | |
|---|---|---|---|---|---|
| | NtAO1-ssTT | NtAO1-SStt | NtAO1-Sstt | NtAO1-SStT | NtAO1-SSTT |
| NtAO1-F2-1 | 3 | 2 | 2 | 1 | 1 |
| NtAO1-F2-1 | 4 | 4 | 2 | 0 | 3 |

The grown individuals (an alkaloid content and a growth state) were evaluated as below.

After 2 to 4 medium leaves were collected during flowering time and cured at 70° C. for 16 hours, the leaves were ground, and the ground leaves were subjected to minor alkaloid analysis. As a result, no difference in alkaloid content based on a genotype was observed between (a) the individuals (1) to (4) and (b) the individual (5) (FIG. 7). The individuals (1) to (4) were substantially normally grown. However, in half of the individuals (1) to (4) each containing one or more mutated alleles, spots were observed in the lower leaves (Table 21 and FIG. 8). No spots were observed in the individual (5). Table 22 summarizes the above results.

TABLE 22

| Result of evaluation | | | |
|---|---|---|---|
| Number of mutated alleles | With spots | With no spots | Total |
| 3 | 2 | 2 | 4 |
| 2 | 8 | 5 | 13 |
| 1 | 1 | 0 | 1 |
| 0 | 0 | 4 | 4 |

The AO1 is an enzyme gene that is involved in NAD+ biosynthesis essential for vital activity and that plays an important role in plant vital activity. The importance of such a role is also clear from the fact that a mutant in which the function of the AO1 has been disrupted is lethal, as described earlier. It is therefore considered that one or more mutated alleles present in the AO1 gene adversely affect a plant physiological state and cause an anomaly (such as occurrence of spots in leaves) which is not observed in an individual having no mutation.

A phenomenon similar to the above anomaly is observed also in the D9_AO2-RNAi of Non-Patent Literature 9. In the D9_AO2-RNAi, a decrease in AO transcript amount in the leaves (as described earlier, considered to substantially represent a decrease in transcript amount of the AO1) is observed. In a case where the results of the present Comparative Examples are taken into consideration with the above phenomena and the above decrease, it is reasonable to expect that the functions of both the AO2 and the AO1 are suppressed in the D9_AO2-RNAi.

In view of the above, it is understood that both suppression of the function of the AO2 gene and maintenance of the function of the AO1 gene are at least necessary for achieving both normal growth and a decrease in alkaloid content in a leaf.

INDUSTRIAL APPLICABILITY

The present invention provides a tobacco plant having a low alkaloid content.

The invention claimed is:

1. A tobacco plant in which a mutation that specifically causes suppression of a function of an endogenous gene is introduced in the endogenous gene in a genome, the endogenous gene being at least one of:
  (a) an endogenous gene which contains, as a coding region, a polynucleotide that encodes a polypeptide having a sequence identity of 95% or higher with an amino acid sequence represented by SEQ ID NO: 2 or SEQ ID NO: 5; and
  (b) an endogenous gene which contains, as a coding region, a polynucleotide that encodes a polypeptide having a sequence identity of 95% or higher with an amino acid sequence represented by SEQ ID NO: 6; wherein respective functions of the following endogenous genes (c) and (d) are not suppressed:
  (c) an endogenous gene which contains, as a coding region, a polynucleotide that encodes a polypeptide having a sequence identity of 95% or higher with an amino acid sequence represented by SEQ ID NO: 62 or SEQ ID NO: 63; and
  (d) an endogenous gene which contains, as a coding region, a polynucleotide that encodes a polypeptide having a sequence identity of 95% or higher with an amino acid sequence represented by SEQ ID NO: 64.

2. The tobacco plant as set forth in claim 1, wherein the suppression of the function is a decrease in an amount of mRNA which has been produced from the at least one of the endogenous genes, as compared with a wild-type plant.

3. The tobacco plant as set forth in claim 2, wherein the suppression of the function is promotion of degradation of the mRNA which has been produced from the at least one of the endogenous genes, as compared with a wild-type plant.

4. The tobacco plant as set forth in claim 2, wherein the suppression of the function is a decrease in an amount of transcription from the at least one of the endogenous genes to the mRNA, as compared with a wild-type plant.

5. The tobacco plant as set forth in claim 1, wherein the suppression of the function is a decrease in an amount of the polypeptide, as compared with a wild-type plant.

6. The tobacco plant as set forth in claim 5, wherein the suppression of the function is a decrease in an amount of translation into the polypeptide, as compared with a wild-type plant.

7. The tobacco plant as set forth in claim 1, wherein the mutation is introduced by mutagen treatment, genome editing, or gene knockout.

8. The tobacco plant as set forth in claim 1, wherein the tobacco plant belongs to *Nicotiana tabacum*, *Nicotiana sylvestris*, or *Nicotiana rustica*.

9. A method of producing a tobacco plant, comprising the step of introducing a mutation in a genome of a tobacco plant, the mutation specifically causing suppression of a function of at least one of:
  (a) an endogenous gene which contains, as a coding region, a polynucleotide that encodes a polypeptide having a sequence identity of 95% or higher with an amino acid sequence represented by SEQ ID NO: 2 or SEQ ID NO: 5; and
  (b) an endogenous gene which contains, as a coding region, a polynucleotide that encodes a polypeptide having a sequence identity of 95% or higher with an amino acid sequence represented by SEQ ID NO: 6; wherein,
  the step of introducing the mutation including introducing the mutation in the at least one of the endogenous genes, and wherein respective functions of the following endogenous genes (c) and (d) are not suppressed:

(c) an endogenous gene which contains, as a coding region, a polynucleotide that encodes a polypeptide having a sequence identity of 95% or higher with an amino acid sequence represented by SEQ ID NO. 62 or SEQ ID NO: 63; and (d) an endogenous gene which contains, as a coding region, a polynucleotide that encodes a polypeptide having a sequence identity of 95% or higher with an amino acid sequence represented by SEQ ID NO. 64.

10. The method as set forth in claim 9, wherein the suppression of the function is a decrease in an amount of mRNA which has been produced from the at least one of the endogenous genes, as compared with a wild-type plant.

11. The method as set forth in claim 10, wherein the suppression of the function is promotion of degradation of the mRNA which has been produced from the at least one of the endogenous genes, as compared with a wild-type plant.

12. The method as set forth in claim 10, wherein the suppression of the function is a decrease in an amount of transcription from the at least one of the endogenous genes to the mRNA, as compared with a wild-type plant.

13. The method as set forth in claim 9, wherein the suppression of the function is a decrease in an amount of the polypeptide, as compared with a wild-type plant.

14. The method as set forth in claim 13, wherein the suppression of the function is a decrease in an amount of translation into the polypeptide, as compared with a wild-type plant.

15. The method as set forth in claim 9, wherein the step of introducing the mutation is carried out by mutagen treatment, genetic modification, genome editing, or gene knockout.

16. A cured leaf having a mutation in (a) an endogenous gene in a genome which endogenous gene contains, as a coding region, a polynucleotide that encodes a polypeptide having a sequence identity of 95% or higher with an amino acid sequence represented by SEQ ID NO: 2 or SEQ ID NO: 5, the mutation suppressing a function of the endogenous gene, and/or having a mutation in (b) an endogenous gene in a genome which endogenous gene contains, as a coding region, a polynucleotide that encodes a polypeptide having a sequence identity of 95% or higher with an amino acid sequence represented by SEQ ID NO: 6, the mutation suppressing a function of the endogenous gene, and having a lower alkaloid content as compared with a cured leaf produced from a tobacco leaf harvested from a wild-type tobacco plant; wherein respective functions of the following endogenous genes (c) and (d) are not suppressed:

(c) an endogenous gene which contains, as a coding region, a polynucleotide that encodes a polypeptide having a sequence identity of 95% or higher with an amino acid sequence represented by SEQ ID NO. 62 or SEQ ID NO: 63; and (d) an endogenous gene which contains, as a coding region, a polynucleotide that encodes a polypeptide having a sequence identity of 95% or higher with an amino acid sequence represented by SEQ ID NO. 64.

17. A tobacco product comprising a cured leaf recited in claim 16.

* * * * *

SEQUENCE LISTING

```
Sequence total quantity: 70
SEQ ID NO: 1              moltype = DNA  length = 1947
FEATURE                   Location/Qualifiers
source                    1..1947
                          mol_type = genomic DNA
                          organism = Nicotiana sylvestris
SEQUENCE: 1
atggcaactg gtatcgcttc aggatgcgga cagttacatt tgaggaagcc tgtctacttg    60
aggaatagct atggaaataa agctcactct cattccaatg tgattctcaa cggcacgcaa   120
aaccagatcg cttggtctag ttgggtttca aatgtcttgc gagttaatag aagtagctat   180
ccacaatgtc aagtgataaa aacaaactgg aagtctcggc gaggaacaat caaatctagc   240
cagcagagag atggtcagt tactaggtac ttcgatttca ttgtgattgg tagtggaatt   300
gctggccttc gatatgcact tgaggttgcc aagcatggaa ctgtggctgt gataaccaag   360
gctgagccac atgagagtag cactaactat gctcaaggtg gtgtaagtgc tgtgctctgc   420
cctttggatt cagtggagaa ccacatacaa gatacaattg tggcaggtgc ttacctctgt   480
gataaggaga ctgttaaagt agtgtgtact gaaggacctg agagaattag agaactgatc   540
gctataggtg cttcattcga tcatggggag gacgaaatc tggatctagc cagggaagga   600
ggccactccc atcgtcgaat tgtccatgct gctgatatga ctggcagaga gattgaaaga   660
gccttattag aggcagtgtt taagaatcct aatatacatg tgtttcaaca ccattttgct   720
```

```
atcgatttgt tgaccactca ggatggttct gacgtagtat gtcatggcgt tgatactata   780
cacacggaaa cgaaggaggt tataagattc atttcaaaag tgactttgct agcatcaggt   840
ggagttggac atatctatcc aagtactact aatccgacgg ttgcaactgg tgatggaatg   900
gctatggctc atcgagctca agctgtaatt tccaacatgg agtttgtgca attccaccca   960
actgccttgg ctgatgaagg gcttcccaac ataccaagtg ccagagagaa tgctttttg   1020
ataactgaag ctgtcagagg tgatggaggc atcctttata acttagatat ggaaagattt  1080
atgccaatgt atgatgaaag agcagaactt gccccgagag atgtggtagc aagaagtata  1140
gatgaccagc tcaaaaagcg tggcgaaaag tatgttcttc ttgatatcag tcacaagccc  1200
agagagaagg ttctgtccca ttttcctaat atagctgctg agtgtctccg ccatgggtta  1260
gacataacac agcagccgat tccggtggtt cctgctgctc actacatgtg tggtggagtc  1320
cgtgctggac tcgagggtga gactaatgtg caaggtcttt atgtggcagg tgaagttgca  1380
tgtactggtt tacatggtgc aaaccgactt gctagcaact cattgcttga agcactagtg  1440
tttgcacgaa gagctgtaca gccttcaatt gatcatgtga acgtgtctag aattgataac  1500
ggtgcatcaa gttggtggcc gcggcctgta gcccccatgg cactaggaga tacagtactt  1560
aacaaagtca tccgtcggac aagggaagtg aggaaagaac tacagtcaat catgtgggaa  1620
tatgttggaa ttgttaggtc tacctcaaga ctaaatactg ctgagaagag aatcaaagag  1680
ttggagttgg aatgggaaac atacctgttt cagcatggct gggaaccaac aatggttgga  1740
gtagaggctt gtgagatgag gaatctcttc tgttgtgcca acctggtagt tagcagtgct  1800
ctttctcgac aagagagtcg tgggcttcac tacaccactg attttcctca tgttgaggaa  1860
agcgagaggt tgccaacggt tatctttcct tctcagcgaa atagcacatg gagcacacgg  1920
caattacacg cgcagccgat aagttag                                        1947

SEQ ID NO: 2         moltype = AA  length = 648
FEATURE              Location/Qualifiers
source               1..648
                     mol_type = protein
                     organism = Nicotiana sylvestris
SEQUENCE: 2
MATGIASGCG QLHLRKPVYL RNSYGNKAHS HSNVILNGTQ NQIAWSSWVS NVLRVNRSSY   60
PQCQVIKTNW KSRRGTIKSS QQRDGSVTRY FDFIVIGSGI AGLRYALEVA KHGTVAVITK  120
AEPHESSTNY AQGGVSAVLC PLDSVENHIQ DTIVAGAYLC DKETVKVVCT EGPERIRELI  180
AIGASFDHGE DGNLDLAREG GHSHRRIVHA ADMTGREIER ALLEAVFKNP NIHVFQHHFA  240
IDLLTTQDGS DVVCHGVDTI HTETKEVIRF ISKVTLLASG GVGHIYPSTT NPTVATGDGM  300
AMAHRAQAVI SNMEFVQFHP TALADEGLPN IPSARENAFL ITEAVRGDGG ILYNLDMERF  360
MPMYDERAEL APRDVVARSI DDQLKKRGEK YVLLDISHKP REKVLSHFPN IAAECLRHGL  420
DITQQPIPVV PAAHYMCGGV RAGLEGETNV QGLYVAGEVA CTGLHGANRL ASNSLLEALV  480
FARRAVQPSI DHVNVSRIDN GASSWWPRPV APMALGDTVL NKVIRRTREV RKELQSIMWE  540
YVGIVRSTSR LNTAEKRIKE LELEWETYLF QHGWEPTMVG VEACEMRNLF CCANLVVSSA  600
LSRQESRGLH YTTDFPHVEE SERLPTVIFP SQRNSTWSTR QLHAQPIS               648

SEQ ID NO: 3         moltype = DNA  length = 1947
FEATURE              Location/Qualifiers
source               1..1947
                     mol_type = genomic DNA
                     organism = Nicotiana tabacum
SEQUENCE: 3
atggcaactg gtatcgcttc aggatgcgga cagttacatt tgaggaagcc tgtctacttg    60
aggaatagct atggaaataa agctcactct cattccaatg tgattctcaa cggcacgcaa   120
aaccagatcg cttggtctag ttgggtttca aatgtcttgc gagttaatag aagtagctat   180
ccacaatgtc aagtgataaa aacaaactgg aagtctcggc gaggaacaat caaatctagc   240
cagcagagag atggatcagt tactaggtac ttcgatttca ttgtgattgg tagtggaatt   300
gctggcctte gatatgcact tgaggttgcc aagcatggaa ctgtggctgt gataaccaag   360
gctgagccac atgagagtag cactaactat gctcaaggtg gtgtaagtgc tgtgctctgc   420
cctttggatt cagtggagaa ccacataaca gatacaattg tggcaggtgc ttacctctgt   480
gataaggaga ctgttaaagt agtgtgtact gaaggacctg agagaattag agaactgatc   540
gctataggtg cttcattcga tcatggggag gacggaaatc tggatctagc caggaagga    600
ggccactccc atcgtcgaat tgtccatgct gctgatatga ctggcagaga gattgaaaga   660
gccttattag aggcagtgtt taagaatcct aatatacatg tgtttcaaca ccatttttgct  720
atcgatttgt tgaccactca ggatggttct gacgtagtat gtcatggcgt tgatactata   780
cacacggaaa cgaaggaggt tataagattc atttcaaaag tgactttgct agcatcaggt   840
ggagttggac atatctatcc aagtactact aatccgacgg ttgcaactgg tgatggaatg   900
gctatggctc atcgagctca agctgtaatt tccaacatgg agtttgtgca attccaccca   960
actgccttgg ctgatgaagg gcttcccaac ataccaagtg ccagagagaa tgctttttg   1020
ataactgaag ctgtcagagg tgatggaggc atcctttata acttagatat ggaaagattt  1080
atgccaatgt atgatgaaag agcagaactt gccccgagag atgtggtagc aagaagtata  1140
gatgaccagc tcaaaaagcg tggcgaaaag tatgttcttc ttgatatcag tcacaagccc  1200
agagagaagg ttctgtccca ttttcctaat atagctgctg agtgtctccg ccatgggtta  1260
gacataacac agcagccgat tccggtggtt cctgctgctc actacatgtg tggtggagtc  1320
cgtgctggac tcgagggtga gactaatgtg caaggtcttt atgtggcagg tgaagttgca  1380
tgtactggtt tacatggtgc aaaccgactt gctagcaact cattgcttga agcactagtg  1440
tttgcacgaa gagctgtaca gccttcaatt gatcatgtga acgtgtctag aattgataac  1500
ggtgcatcaa gttggtggcc gcggcctgta gcccccctgg cactaggaga tacagtactt  1560
aacaaagtca tccgtcggac aagggaagtg aggaaagaac tacagtcaat catgtgggaa  1620
tatgttggaa ttgttaggtc tacctcaaga ctaaatactg ctgagaagag aatcaaagag  1680
ttggagttgg aatgggaaac atacctgttt cagcatggct gggaaccaac aatggttgga  1740
gtagaggctt gtgagatgag gaatctcttc tgttgtgcca acctggtagt tagcagtgct  1800
ctttctcgac aagagagtcg tgggcttcac tacaccactg attttcctca tgttgaggaa  1860
agcgagaggt tgccaacggt tatctttcct tctcagcgaa atagcacatg gagcacacgg  1920
caattacacg cgcagccgat aagttag                                        1947
```

```
SEQ ID NO: 4            moltype = DNA  length = 1947
FEATURE                 Location/Qualifiers
source                  1..1947
                        mol_type = genomic DNA
                        organism = Nicotiana tabacum
SEQUENCE: 4
atggcaactg gtatcgcttc aggatgcgga cagttacact tgaggaagcc tgtctacttg   60
aggaatagct atggaaataa agctcactgt cattccaatg tgattctcaa cggcacgcaa  120
aaccagatcg cttggtctag ttgggtttca aatgtcttgc gagttaatag aagtagctat  180
ccagaatgtc aagtgatcaa gacaaactgg aagtctagcc gaggaacaat caaatcgtgc  240
cagcagagag atggatcagt tactaggtac ttcgatttca ctgtgattgg tagtggaatt  300
gctggccttc gatatgcact tgaggttgcc aagcatggaa ctgtggctgt aataaccaag  360
gctgagccac atgaagagtag cactaactat gctcaaggtg gtaagtgc tgtgctctgc  420
cctttggatt cagtggagag ccatatgcaa gatacaattg tggcaggtgc ttatctctgt  480
gataaggaga ctgttagagt agtgtgtact gaaggacctg agagaattag agaactgatc  540
gctatggtgt cttcattcga tcatggggag gacgaaaatc tggatctagc cagggaagga  600
ggccactccc atcgtcgaat tgtccatgct gctgatatga ctggcagaga gataagaata  660
gctctattag aggcagtttt taagaatcct aatatacatg tgtttcaaca ccatttttgct  720
atagatttgt tgaccactca ggatggttct gacatagtat gtcatggcgt tgatactata  780
cacacgaaa cgaaggaggt tataagattc atttcaaaag tgactttgct ggcatcaggt  840
ggagttggac atatcatcc aagtactact aatccgactg ttgcaactgg tgatggaatg  900
gctatggctc atcgagctca agctgtaatt tccaacatgg agtttgtgca attccaccca  960
actgccttgg ctgatgaagg ccttcccaac ataccaagtg ccagagagaa tgcttttttg  1020
ataactgaag ctgtcagagg tgatggaggc atccttttaca acttagatat ggaaagattt  1080
atgccaatgt atgatgaaaa agcagaactt gccccgacaa gttggtaag aagaagtata  1140
gatgaccagc tcaaaaagcg tggcgaaaag tatgttcttc ttgatatcag tcacaagccc  1200
agagagaagg ttctttctca ttttcctaat atagctgctg agtgtctccg ccatggggtta  1260
gacataacac agcagccgat tccggtggtt cctgctgctc actacatgtg tggtggagtc  1320
cgtgctggac tcgagggtga gactaatgtg caaggtcttt atgtggcagg tgaagttgca  1380
tgtactggtt tacatggtgc taaccgactt gctagcaact cattgcttga agcactagtg  1440
tttgcacgaa gagctgtaca gccttcaatt gatcatgtga acgtgtctag aattgatcac  1500
ggtgcttcaa gttggtggcc gcggcctgta gcccccatgg tactaggaga tacagtactt  1560
aacaaagtca tctgtcggac aagggaagtg aggaaagaac tacagtcaat catgtgggaa  1620
tatgttggaa ttgttaggtc taactcaaga ctaaacactg ctgagaagag aatcagagag  1680
ttggagttgg aatgggaaac atccctatttt cagcatggct gggaaccaac aatggttgga  1740
gtagaggctt gtgagatgag gaatctcttc tgttgtgcca acttggtagt tagcagtgct  1800
cttttctcgac atgagagtcg tgggcttcac tacaccactg attttcctca tgttgaggaa  1860
agcgagaggt tgccaacggt catttttcct tctcagcgaa ataactcatg gagctcacgc  1920
caattacacg cgcagccgat aagttag                                      1947

SEQ ID NO: 5            moltype = AA  length = 648
FEATURE                 Location/Qualifiers
source                  1..648
                        mol_type = protein
                        organism = Nicotiana tabacum
SEQUENCE: 5
MATGIASGCG QLHLRKPVYL RNSYGNKAHS HSNVILNGTQ NQIAWSSWVS NVLRVNRSSY   60
PQCQVIKTNW KSRRGTIKSS QQRDGSVTRY FDFIVIGSGI AGLRYALEVA KHGTVAVITK  120
AEPHESSTNY AQGGVSAVLC PLDSVENHIQ DTIVAGAYLC DKETVKVVCT EGPERIRELI  180
AIGASFDHGE DGNLDLAREG GHSHRRIVHA ADMTGREIER ALLEAVFKNP NIHVFQHHFA  240
IDLLTTQDGS DVVCHGVDTI HTETKEVIRF ISKVTLLASG GVGHIYPSTT NPTVATGDGM  300
AMAHRAQAVI SNMEFVQFHP TALADEGLPN IPSARENAFL ITEAVRGDGG ILYNLDMERF  360
MPMYDERAEL APRDVVARSI DDQLKKRGEK YVLLDISHKP REKVLSHFPN IAAECLRHGL  420
DITQQPIPVV PAAHYMCGGV RAGLEGETNV QGLYVAGEVA CTGLHGANRL ASNSLLEALV  480
FARRAVQPSI DHVNVSRIDN GASSWWPRPV APLALGDTVL NKVIRRTREV RKELQSIMWE  540
YVGIVRSTSR LNTAEKRIKE LELEWETYLF QHGWEPTMVG VEACEMRNLF CCANLVVSSA  600
LSRQESRGLH YTTDFPHVEE SERLPTVIFP SQRNSTWSTR QLHAQPIS              648

SEQ ID NO: 6            moltype = AA  length = 648
FEATURE                 Location/Qualifiers
source                  1..648
                        mol_type = protein
                        organism = Nicotiana tabacum
SEQUENCE: 6
MATGIASGCG QLHLRKPVYL RNSYGNKAHC HSNVILNGTQ NQIAWSSWVS NVLRVNRSSY   60
PECQVIKTNW KSSRGTIKSC QQRDGSVTRY FDFTVIGSGI AGLRYALEVA KHGTVAVITK  120
AEPHESSTNY AQGGVSAVLC PLDSVESHMQ DTIVAGAYLC DKETVRVVCT EGPERIRELI  180
AMGASFDHGE DGNLDLAREG GHSHRRIVHA ADMTGREIER ALLEAVFKNP NIHVFQHHFA  240
IDLLTTQDGS DIVCHGVDTI HTETKEVIRF ISKVTLLASG GVGHIYPSTT NPTVATGDGM  300
AMAHRAQAVI SNMEFVQFHP TALADEGLPN IPSARENAFL ITEAVRGDGG ILYNLDMERF  360
MPMYDERAEL APRDVVARSI DDQLKKRGEK YVLLDISHKP REKVLSHFPN IAAECLRHGL  420
DITQQPIPVV PAAHYMCGGV RAGLEGETNV QGLYVAGEVA CTGLHGANRL ASNSLLEALV  480
FARRAVQPSI DHVNVSRIDH GASSWWPRPV APMVLGDTVL NKVICRTREV RKELQSIMWE  540
YVGIVRSNSR LNTAEKRIRE LELEWETYLF QHGWEPTMVG VEACEMRNLF CCANLVVSSA  600
LSRHESRGLH YTTDFPHVEE SERLPTVIFP SQRNNSWSSR QLHAQPIS              648

SEQ ID NO: 7            moltype = DNA  length = 21
FEATURE                 Location/Qualifiers
```

```
misc_feature          1..21
                      note = Synthetic Primer
source                1..21
                      mol_type = other DNA
                      organism = synthetic construct
SEQUENCE: 7
tgcacgacca taatacttca c                                              21

SEQ ID NO: 8          moltype = DNA  length = 21
FEATURE               Location/Qualifiers
misc_feature          1..21
                      note = Synthetic Primer
source                1..21
                      mol_type = other DNA
                      organism = synthetic construct
SEQUENCE: 8
aagctcgtga cctgtgatat g                                              21

SEQ ID NO: 9          moltype = DNA  length = 21
FEATURE               Location/Qualifiers
misc_feature          1..21
                      note = Synthetic Primer
source                1..21
                      mol_type = other DNA
                      organism = synthetic construct
SEQUENCE: 9
catgacgtga cacaattcta g                                              21

SEQ ID NO: 10         moltype = DNA  length = 21
FEATURE               Location/Qualifiers
misc_feature          1..21
                      note = Synthetic Primer
source                1..21
                      mol_type = other DNA
                      organism = synthetic construct
SEQUENCE: 10
gtgatatgtt tgactgggca c                                              21

SEQ ID NO: 11         moltype = DNA  length = 15
FEATURE               Location/Qualifiers
misc_feature          1..15
                      note = Synthetic Primer
source                1..15
                      mol_type = other DNA
                      organism = synthetic construct
SEQUENCE: 11
ctaggtactt cgatt                                                     15

SEQ ID NO: 12         moltype = DNA  length = 22
FEATURE               Location/Qualifiers
misc_feature          1..22
                      note = Synthetic Primer
source                1..22
                      mol_type = other DNA
                      organism = synthetic construct
SEQUENCE: 12
gtatgtggtt ctccactgaa tc                                             22

SEQ ID NO: 13         moltype = DNA  length = 21
FEATURE               Location/Qualifiers
misc_feature          1..21
                      note = Synthetic Primer
source                1..21
                      mol_type = other DNA
                      organism = synthetic construct
SEQUENCE: 13
atgtgtttca acaccatttt g                                              21

SEQ ID NO: 14         moltype = DNA  length = 20
FEATURE               Location/Qualifiers
misc_feature          1..20
                      note = Synthetic Primer
source                1..20
                      mol_type = other DNA
                      organism = synthetic construct
SEQUENCE: 14
acaacatcaa atccttgctg                                                20

SEQ ID NO: 15         moltype = DNA  length = 22
```

```
FEATURE                 Location/Qualifiers
misc_feature            1..22
                        note = Synthetic Primer
source                  1..22
                        mol_type = other DNA
                        organism = synthetic construct
SEQUENCE: 15
ccaacatcca ttacatactt ag                                            22

SEQ ID NO: 16           moltype = DNA   length = 21
FEATURE                 Location/Qualifiers
misc_feature            1..21
                        note = Synthetic Primer
source                  1..21
                        mol_type = other DNA
                        organism = synthetic construct
SEQUENCE: 16
caccagttgc aacctataat c                                             21

SEQ ID NO: 17           moltype = DNA   length = 22
FEATURE                 Location/Qualifiers
misc_feature            1..22
                        note = Synthetic Primer
source                  1..22
                        mol_type = other DNA
                        organism = synthetic construct
SEQUENCE: 17
gaaagattta tgccaatgta tg                                            22

SEQ ID NO: 18           moltype = DNA   length = 21
FEATURE                 Location/Qualifiers
misc_feature            1..21
                        note = Synthetic Primer
source                  1..21
                        mol_type = other DNA
                        organism = synthetic construct
SEQUENCE: 18
tctgggcttg tgactgatat c                                             21

SEQ ID NO: 19           moltype = DNA   length = 22
FEATURE                 Location/Qualifiers
misc_feature            1..22
                        note = Synthetic Primer
source                  1..22
                        mol_type = other DNA
                        organism = synthetic construct
SEQUENCE: 19
ctagaattga taacggtgca tc                                            22

SEQ ID NO: 20           moltype = DNA   length = 23
FEATURE                 Location/Qualifiers
misc_feature            1..23
                        note = Synthetic Primer
source                  1..23
                        mol_type = other DNA
                        organism = synthetic construct
SEQUENCE: 20
gaggtagacc taacaattcc aac                                           23

SEQ ID NO: 21           moltype = DNA   length = 28
FEATURE                 Location/Qualifiers
misc_feature            1..28
                        note = Synthetic Primer
source                  1..28
                        mol_type = other DNA
                        organism = synthetic construct
SEQUENCE: 21
cacctgagga atagctatgg aaataaag                                      28

SEQ ID NO: 22           moltype = DNA   length = 24
FEATURE                 Location/Qualifiers
misc_feature            1..24
                        note = Synthetic Primer
source                  1..24
                        mol_type = other DNA
                        organism = synthetic construct
SEQUENCE: 22
tgaaatcgaa gtacctagta actg                                          24
```

```
SEQ ID NO: 23            moltype = DNA   length = 26
FEATURE                  Location/Qualifiers
misc_feature             1..26
                         note = Synthetic Primer
source                   1..26
                         mol_type = other DNA
                         organism = synthetic construct
SEQUENCE: 23
caccagagag tcgtgggctt cactac                                              26

SEQ ID NO: 24            moltype = DNA   length = 21
FEATURE                  Location/Qualifiers
misc_feature             1..21
                         note = Synthetic Primer
source                   1..21
                         mol_type = other DNA
                         organism = synthetic construct
SEQUENCE: 24
ctaacttatc ggctgcgcgt g                                                   21

SEQ ID NO: 25            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 25
taagagacag gcgaggaaca atcaaatcta                                          30

SEQ ID NO: 26            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 26
taagagacag gggaaatagt ctccaaatta                                          30

SEQ ID NO: 27            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 27
taagagacag gcagagagat tgaaagagcc                                          30

SEQ ID NO: 28            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 28
taagagacag ctgaatagtt caattgcgac                                          30

SEQ ID NO: 29            moltype = DNA   length = 29
FEATURE                  Location/Qualifiers
misc_feature             1..29
                         note = Synthetic Primer
source                   1..29
                         mol_type = other DNA
                         organism = synthetic construct
SEQUENCE: 29
taagagacag aggatgcgga cagttacac                                           29

SEQ ID NO: 30            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 30
taagagacag gccatggata atagtttgac                                          30
```

```
SEQ ID NO: 31            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 31
taagagacag taaacatcgc gctaataatc                                         30

SEQ ID NO: 32            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 32
taagagacag tagacttcca gtttgtcttg                                         30

SEQ ID NO: 33            moltype = DNA   length = 30
FEATURE                  Location/Qualifiers
misc_feature             1..30
                         note = Synthetic Primer
source                   1..30
                         mol_type = other DNA
                         organism = synthetic construct
SEQUENCE: 33
taagagacag cagagagata gaaagagctc                                         30

SEQ ID NO: 34            moltype = DNA   length = 29
FEATURE                  Location/Qualifiers
misc_feature             1..29
                         note = Synthetic Primer
source                   1..29
                         mol_type = other DNA
                         organism = synthetic construct
SEQUENCE: 34
taagagacag caagtaagag cgcagaagc                                          29

SEQ ID NO: 35            moltype = DNA   length = 9075
FEATURE                  Location/Qualifiers
source                   1..9075
                         mol_type = genomic DNA
                         organism = Nicotiana sylvestris
SEQUENCE: 35
attttggtgc acctgaaaat gatataccgg attactaaac ttatatttta tgttttttta        60
atgtaatttc aatttagtg tatcctcctt tgatgtactt ttaattttaa tgtattttta       120
ttttatgtat tgttaatttt cttttttaaat tttagttttc acttttcaat tttagcaaca      180
ttagatatct tacatttgca tttttcattt ttaaataatt gttatatttc tttttataca       240
attataataa taataaaatt aacttataat tttatatata atatatataa aaattaatat       300
atcaaaaaaa taggatataa aattaaaatt ataaagatct taatataaaa attaactata       360
tacacaatat atgataaatt aaagtccaaa aaaataaaaa taaaaagaa taaaataata        420
ataaatcaaa tttggtgttg atgaatagtg tcacaccaaa tttggtgtga gactattcaa       480
atactaaaat ggtgcaaaat ttgatgttcc attggagcaa aaaaaatact aaatcttaca       540
ccaaatttag atttgctgca aaaaatagtg caccattgga gatgccctaa gaccatctcc       600
aaggctgcat tatagagcat gaatagtgtt gcaccaaatt tggtgcaaca ctattcatca       660
ctccatattt ggtttattat tattttattc aatctttta tttttggac tttaattta         720
tcatatattg tgtatataat taatttttat attaagatct ttatatttt aattttat         780
cctatttttt gatatattaa ttttgtatat attatattta tataaaatta taagttaatt      840
ttattattat tataattgta taaaaagaga tataaccgtt atttaaaaat aaaaaatgca       900
aatgtaagat atcaatgat gcgcatttcg cacttcgtaa tgcattaatc gagcatttat        960
gggagaataa aggcgtaagt taaatattta tgtggtactt aattaaatt tgactatgat      1020
gtaatattta tttaattatc ttttatcaat gatttcactt ttagttgatt tatccttaa      1080
aaaaattttg taataatga ttatataagt ggtgaatgtg aattatatat aatgaatatg      1140
gaaaaaagaa aaaagatagt attagtttga aggaaataaa aatgaaaag taatagaag      1200
ataataatat aatatagaag agagagaaga tttggtgtaa aaaattgtgt aatggttgaa      1260
ttaaatatgg tgttacatca ttttgatgtg aaatttggtg ttagggttgc agatggccta      1320
agaggagtga cctattgtct agatagtaat aatgtagttt tgtttaacta agtagtggt      1380
tatatgttca actttagagg ttttgctttt tacttgtata tatttttttc ctggtgaata     1440
aactttagt tacccaaaaa taataataat tgagttaaaa gaattgttac aaagaaacac     1500
aaataaggta atattgtaaa ccacgaagaa ggtcagtgtg tgagatacaa aatgtcagga     1560
gaggtgtctg caattattgt tttttggcatt gctgagaaca ttaacaataa gaaaaaagca   1620
ttaacaatca acatatattc aaattggtaa aaaaacatgt tcaaattggt gggttagaat     1680
aagttaggac ccattaacta tttaatcagt ttaaatttag gtagactcta ttatttgatt     1740
gtagatataa aagataatat taagagagaa actaccaac ccctgtaaca ttaaaaaaaaa   1800
gttagaaaca atgttcatta gaagatccaa aaggcaaaag ataaaaataa agagaaataa     1860
gatgaccgaa accaacaatt gatcgagcaa acaataaaca aagaggatag agaagaaaaa     1920
```

```
ctcacgagga atcgagaaag acaaaggaga aggaaagaga tatggaaaaa tgaaaatctt   1980
agtttcagat ggagtgctga aggcaaaagg gttaggaaaa attaaatcac gtgggaattg   2040
gaagtgaata aatgtaaggc catagcacct caaaatatac acgcagtcag aggctggacg   2100
ggaccaggat ttcaagttta tgggttcgga attccaatag tttgaagtta ctgtgttcta   2160
gattaataat ttatacatat tcaatgacat ttttaagaca aatatagtgt tcgaaccaaa   2220
gctactaggt tcggccgaac ccgctcccgc cactctagct ccacgcatgc agcaattaag   2280
tactccataa tgattgaatt acacataaac aaatgcataa gcaacgtggt gtttgcaagt   2340
gaacagctga agtccatag cacctcaaaa aagactaagg taagggtatc aatacaagca    2400
gcaattaagt aataaggacc aaatcacaca gtatccctaa acaaaatactt attaagtgat   2460
gaggtacgaa tcggaatcgc acagtatcac taaacaaatg catacaccac gtgggtgtta   2520
tggaagtgaa gtcataagca cctcaaaaat ggaccaaatt acacagttat ccctaaacaa   2580
atgcataata ccgaaactac ccatgcacga ccataatact tcacttatta tatagttatg   2640
gcttctgctt ccttggccaa caatcagttc atctctaact tcgaattcca gttccatttt   2700
cacttgacac acttcgaagc gccatctttg ctactttaag gtaattgtat atttcaaaag   2760
tttgtttttgc ttatctgttt tggaatgaca gcggtaattg tgttgtttaa caaatttaca   2820
tgctccaaat gaatggaaga agagttctaa cttcaagacc atggccagag gccagttgtt   2880
aattcctaag atcatcctga acaaaatctt ctctatatgt agcctctacg tactatattc   2940
gttcatgctt taatgtgtaa tgcataacaa gattttacct taaatatcca gatcgatcat   3000
atggcaactg gtatcgcttc aggatgcgga cagttacatt tgaggaagcc tgtctacttg   3060
aggaatagct atggaaataa agctcactct cattccaatg tgattctcaa cggcacgcaa   3120
aaccagatcg cttggtacgt tttagggta aaccagtaat atattttttc atgacgtgac    3180
acaattctag aagtagtcat ttcctgattc cttaggaaaa gggaaggtta tttcgtccca   3240
atttatatat catagttaca cattcttata tttagtagta acaatttaac tttaaaatac   3300
ctcttttacc cttaatgaaa tgatttatag ccaaacacat atccattgct cagtttacac   3360
cataaatttc aaaatattc ttaaatattg tgcccagtca acatatcac ataaattgag     3420
acattgagac ataggagt actatcttaa ttttctgatg gtgatatgct ttaccaggtc     3480
tagttgggtt tcaaatgtct tgcgagttaa tagaagtagc tatccacaat gtcaagtgat   3540
aaaaacaaac tggaagtctc ggcgaggaac aatcaaatct agccagcaga gagatgggtc   3600
agttactagg tacttcgatt tcattgtgat tggtagtgga attgctggcc ttcgatatgc   3660
acttgaggtt gccaagcatg gaactgtggc tgtgataacc aaggctgagc cacatgagag   3720
tagcactaac tatgctcaag gtggtgtaag tgctgtgctc tgccctttgg attcagtgga   3780
gaaccacata caagatacaa ttgtggcagg tgcttacctc tgtgataagg agactgttaa   3840
agtaagttca cacgaatata ttcagtttaa tttggagact atttcccccc ttttgctttt   3900
gctataagtg tatctctcct ttaatttctc caggtagtgt gtactgaagg acctgagaga   3960
attagagaac tgatcgctat aggtgcttca ttcgatcatg gggaggacgg aaatctggat   4020
ctagccaggg aaggaggcca ctcccatcgt cgaattgtcc atgctgctga tatgactggc   4080
agagagattg aaagagcctt attagaggca gtgtttaaga atcctaatat acatgtgttt   4140
caacaccatt ttgctatcga tttgttgacc actcaggtta gtttattagt gtgctatagt   4200
tgagtaaagg tcgcaattga actattcagc aaggatttga tgttgtaatt tgtatggcaa   4260
atgcaggatg gttctgacgt agtatgtcat ggcgttgata ctatacacac ggaaacgaag   4320
gaggtaagta acagttgctt tcactcatgt tgacttttca acattcttca aaatgacata   4380
aattgatttt cttacttgtg tatttaggt tataagattc atttcaaaag tgactttgct    4440
agcatcaggt ggagttggac atatctatcc aagtactact aatccgacgg tatgtttca    4500
atatcttttc ctccaaaatc ttgttagtta tgattaatgt catgctccaa aaataaaaga   4560
tctggacatg gcactcgatc gatgctttga aacttgtgac agagcgaacc aacatccatt   4620
acatacttag tgcaattaga aatatgagct cgctgcccta aatgcctaaa aaggattct    4680
gttttt atac tttgaccatt tgtgccaaca gaaaagttta accctgttga atgtgggctt   4740
gtttaacttt ctaattcata ttgacattat gattataggt tgcaactggt gatggaatgc   4800
ctatggctca tcgagctcaa gctgtaattt ccaacatgga gtaagtaatc ctcagtagca   4860
ttatttttat tgtacaatat ctctgcctct gcttagtga gttttgtgct gtaaaatctg    4920
ctgacctaga tttcatcctt tttttttttct ttcctgattt ctgcatcttg ttcagcattt  4980
cgttcagaat ttgcactttc gactaaaaac acaagggtgt gttcaaaaat ttgcattatt   5040
aataacaatt ctcttcctcg tgttgccagg tttgtgcaat tccacccaac tgccttggct   5100
gatgaagggc ttcccaacat accaagtgcc agagagaatg cttttttgat aactgaagct   5160
gtcagaggtg atggaggcat cctttataac ttagatatgg aaagatttat gccaatgtat   5220
gatgaaagag cagaacttgc cccgagagat gtggtagcaa gaagtataga tgaccagctc   5280
aaaaagcgtg gcgaaaagta tgttcttctt gatatcagtc acaagcccag agagaaggtt   5340
ctgtcccatt ttcctaatat agctgctgag tgtctccgcc atgggttaga cataacacag   5400
cagccgattc cggtggttcc tgctgctcac tacatgtgtg gtggagtccg tgctggactc   5460
gagggtgaga ctaatgtgca aggtctttat gtggcaggtg aagttgcatg tactggttta   5520
catggtgcaa accgacttgc tagcaactca ttgcttgaag cactagtgtt tgcacgaaga   5580
gctgtacagc cttcaattga tcatgtgaac gtgtctagaa ttgataacgg tgcatcaagt   5640
tggtggccgc ggcctgtagc ccccatggca ctaggagata cagtacttaa caaagtcatc   5700
cgtcggacaa gggaagtgag gaaagaacta cagtcaattc tgtgggaata tgttggaatt   5760
gttaggtcta cctcaagact aaatactgct gagaagagaa tcaaagagtt ggagttggaa   5820
tgggaaacat acctgtttca gcatggctgg gaaccaacaa tggttggagt agaggcttgt   5880
gagatgagga atctcttctg ttgtgccaac ctggtagtta gcagtgctct ttctcgacaa   5940
gagagtcgtg ggcttcacta caccactgat tttcctcatg ttgaggaaag cgagaggttg   6000
ccaacggtta tcttcccttc tcagcgaaat agcacatgga gcacacggca attacacgcg   6060
cagccgataa gttagatatc tcttacctat ttgccattct tcctgccaaa acatctccag   6120
tgcaggacat gatttgtcga ttttaccggg ttgcagggt gtatctatcg aaggggtat    6180
gggttcatat gaacacatac tcctctccat agactatgta taataatgta tatttcttca   6240
atgttatttta aatatgcaag tgtgtcagcc aagctcaaag agttcaataa ttattgggta   6300
catctttaca gtgaaattg tgattttaaa tcccatgtct atttgtcgt tttteccttt     6360
atctttccg ccgaaagtca aatctcacat ttctcttgtt ggttttcctt tcttttccta    6420
taaatgggtc tacccatgat aaaagaaatt tcatatttt gtttagtaa tttctgaatg     6480
caggttttga caatttatta aaaacatatc acaggtcacg agctttaatt agttaagtaa   6540
gcaacttgtt aaatgtgcca gacctgattc ttagtgcaat tcacccttct tcattttcta   6600
ggatagttct cctagccagt ctgtaacttg ctctgttcat ggcaaattac aagtgcgtga   6660
```

```
tagtttggag accataggaa ccctgaactc gaaattgggg aaattagaga aaaggcatcg   6720
aaaattaacc ataaatcaga acaaaatacc tcaaaccatg agtacctcca tgaattttgc   6780
tctaaatcat gtaggttttg atcaaattta gctacaaact tgcgttcttt ggagagagag   6840
aattggaaag ttaagtccat tctagaagaa aatgacgaac atggtcccta atctattggg   6900
atttgatcat tttggtcctt aatgtatgca cttgacctat atagtccttta acctatttta  6960
aaaggtgact cttttggttt gaaacactat aactaacggt atagttacta gcacccactg   7020
ggcatatggc ttataagcat caatagacgt agccttggaa aggaatggaa attttagggc   7080
cttgtgaggg tagagtaatc cttggtaatg gacatatttt tcttttttat aattaaatga   7140
tattactgaa tggtattcca aacatgtcaa ttgttccttt ttataaggca cataggtggg   7200
gtaatccgga attgtatagt cgggtataac ttctcgagtg atgagatgtt tcagagttta   7260
agtaattgaa ttctcatata tgggataagt attcacttta gtgtaaatct tacttccagt   7320
taagacagga tattaagcga ccgaagaata cggccaaaag cggggaagc tagaagcgaa    7380
aaaatatctc gcttgagtcc tccaaaggaa gataagagat agtaatgtta gtaagaaata   7440
gatagaagga taagtatgag aaatgtttaa caattataag ctgaagtatg gtattatgac   7500
aaggttcgta atcaagaaaa agtgaaggca agttttaatt ataaagaggt atgagtcgta   7560
atcacgagaa gtgaattttc gacttcaata agagttatca aaagaccaat ctagcccctg   7620
gattaagaaa taccaatatt aggtagtaac ctaagataac gagatgcaag ttagaaactc   7680
aaaggatttc tgtaatagtt ggcattgcga catttacaaa gtgaatgatc aggcagtaaa   7740
agggtgaatg actatggaac aaccttttgag ggttagtaga aagagctctc cctgagagaa   7800
gcgtcataag caaagttaag ctcatcaagg tcgagcatac cagttatgag tatacaaatac  7860
tacatacata taagttatcc aattgcttta gtagggaaga ttaccccaag gcaagttata   7920
agccactgaa attgcaaaga attgcaaaag gtggagagtt aacgatgtga cctctacaag   7980
agtggaattc aagagcataa ggagttaatt attctcccga gggaagatcg tatgataaag   8040
tatcgaggca aaattatgag gttcgcttag taacggagcg gtaagaagga ttacgacaag   8100
aggtttgaaa ggaataagat tgtacttact tagaccctac aaatgtgtaa cgactctaat   8160
gcataagtac aaacggtaga gaaaatgcag taatgacttc ctgactagag gtaccaattg   8220
atggtaaata aaactaggca gttgatactc aggaagctag tgtgaggggt aaattaaggc   8280
aaaaacatag cctcaagagg agttacttag atttttaccta tgaagataat tgattgagca   8340
atcagtgatt agcttatgaa gggtctagtt atgggttaga cgacaaaact cagacgagtc   8400
attagatcat gcaaaattac agtgttggatc aaaacgtaca aagtttcagc ctcgcaagtg   8460
catgatcgcg actctcagaa agtatttcaa gacataagca atggtaggtg aaattccata   8520
ttatctttta gaaaatcgga aggagcccat tgagcttaaa atatgaggga ggtgttcaaa   8580
agttgtgatc agaagtaata ttatagtaaa ggagaggtga aaaacaatta gatattattt   8640
tagatagttc aaaatcacct aaagttctag ggagtatatg atgtaatgag ctcgcagtca   8700
gatatgaaca agagaatctt ttctaagtgt gtatacgact aaaatcggag agtccgattt   8760
tatgatcgtt atgacattcc acggctcagc ttcagaaggc ctgaggcaca gttcgaagtt   8820
cgaccccgag ggtctcaat gcccaacctc ggggtaacgt aaatcgacga ctatcttgca   8880
taagcgaaaa gttcccaagg cgcgtgctca aagctgacaa cacctgcaaa tatagtataa   8940
gttcgtactg tggcattaaa tagctgtacc aggttcatat ctttgtaata aatgcatatg   9000
tactatgttg gggttctccc tcctatataa aggggaccct tgttattttt ttcatacatg   9060
atatttaata caaga                                                     9075

SEQ ID NO: 36          moltype = DNA   length = 9077
FEATURE                Location/Qualifiers
source                 1..9077
                       mol_type = genomic DNA
                       organism = Nicotiana tabacum
SEQUENCE: 36
tggtgcacct gaaaatgata taccggatta ctaaacttat attttatgtt tttttaatgt   60
aatttcaatt ttagtgtatc ctcctttgat gtactttaa ttttaatgta tttttatttt    120
atgtattgtt aattttcttt ttaaatttta gttttcactt ttcaatttta gcaacattaa   180
atatcttaca tttgcatttt tcatttttaa ataattgtta tatttctttt tatacaatta   240
taataataat aaaattaact tataatttta tatataatat atataaaat taatatatca    300
aaaaaatagg atataaaatt aaaattataa agatcttaat ataaaatta actatataca    360
caatatatga taaattaaag tccaaaaaaa taaaaataaa aagaataaa ataataataa    420
atcaaatttg gtgttgatga atagtgtcac accaaatttg gtgtgagact attcacatac   480
taaaatggtg caaaattgta tgttccattg gagcaaaaaa aatactaaat cttacaccaa   540
atttagattt gctgcaaaaa atagtgcatc attggagatg ccctaagacc atctccaagg   600
ctgcattata gagcatgaat agtgttgcac caaatttggt gcaacactat tcatcactcc   660
atatttggtt tattattatt ttattcaatc ttttttattt ttggactttt aattattcat    720
atattgtgta tataattaat tttatatta agatctttat aatttaattt ttatatccta    780
tttttgata tattaatttt gtatatatta tatttatata aaattataag ttaatttat     840
tattattata attgtataaa aagagatata accgttattt aaaaataaa aatgcaaatg    900
taagatatct aatgatgcgc atttcgcact tcgtaatgca ttaatcgagc atttatggga   960
gaataaaggc gtaagttaaa tatttatgtg gtacttaaat taaatttgac tatgatgtaa   1020
tatttattta attatctttt atcaatgatt tcacttttag ttgatttatc ctttaaaaaa   1080
attttgtaat aaatgattat ataagtggtg aatgttaatt atatataatg aatatggaaa   1140
aaagaaaaaa gatagtatta gttttgaagga aataaaaaat gaaagtaaa tagaagataa   1200
taatataata tagaagagag agaagattg gtgtaaaaaa ttgtgtaatg gttgaattaa   1260
atatggtgtt acatcatttt gatgtgaat ttggtgtag ggttgcagat ggcctaagag    1320
gagtgaccta ttgtctagat agtaaatgg cagttttgtt taactaaagt agtggttata   1380
tgttcaactt tagaggtttt tgcttttact tgtatatatt ttttcctgg tgaataaact    1440
tttagttacc caaaaataat aataattgag ttaaagaat tgttacaaag aaacacaaat   1500
aagtaatat tgtaaaccac gaagaaggtc agtgtgtgag atacaaaatg tcaggagagg   1560
tgtctgaaat tattgtttt ggcattgctg agaacattaa caataagaaa aaagcattaa    1620
caatcaacat atattcaaat tggtaaaaaa acatgttcaa attggtgggt tagaataagt   1680
taggacccat taactatttta atcagtttaa atttaggtag actctattat ttgattgtag   1740
atataaaaga taatattaaa gagagaaact accaaccccct gtaacattaa aaaaaagtta  1800
gaaacaatgt tcattagaag atccaaaagg caaaagataa aaataaagag aaataagatg   1860
```

```
accgaaacca acaattgatc gagcaaacaa taaacaaaga ggatagagaa gaaaaactca   1920
cgaggaatcg agaaagacaa aggagaagga aagagatatg gaaaaatgaa aatcttagtt   1980
tcagatggag tgctgaaggc aaaagggtta ggaaaaatta aatcacgtgg gaattggaag   2040
tgaataaatg taaggccata gcacctcaaa atatacacgc agtcagaggc tggacgggac   2100
caggatttca agtttatggg ttcggaattc caatagtttg aagttactgt gttctagatt   2160
aataatttat acatattcaa tgatattttt aagacaaata tagtgttcga accaaagcta   2220
ctaggttcgg ccgaacccgc tcccgccact atagctccac ccttgcatgc agcaattaag   2280
tactccataa tgattgaatt acacataaac aaatgcataa gcaacgtggt gtttgcaagt   2340
gaacagctga aagtccatag cacctcaaaa aagactaagg taagggtatc aatacaagca   2400
gcaattaagt aataaggacc aaatcacaca gtatccctaa acaaatactt attaagtgat   2460
gaggtacgaa tcggaatcgc acagtatcac taaacaaatg catacaccac gtgggtgtta   2520
tggaagtgaa gtcataagca cctcaaaaat ggaccaaatt acacagttat ccctaaacaa   2580
atgcataata ccgaaactac ccatgcacga ccataatact tcacttatta tatagttatg   2640
gcttctgctt ccttggccaa caatcagttc atctctaact tcgaattcca gttccattit   2700
cacttgacac acttcgaagc gccatctttg ctactttaag gtaattgtat atttcaaaag   2760
tttgttttgc ttatctgttt tggaatgaca gcggtaattg tgttgtttaa caaatttaca   2820
tgctccaaat gaatggaaga agagttctaa cttcaagacc atggccagag gccagttgtt   2880
aattcctaag atcatcctga acaaaatctt ctctatatgt agcctctacg tactatattc   2940
gttcatgctt taatgtgtaa tgcataacaa gattttaccct taaatatcca gatcgatcat   3000
atggcaactg gtatcgcttc aggatgcgga cagttacatt tgaggaagcc tgtctacttg   3060
aggaatagct atggaaataa agctcactct cattccaatg tgattctcaa cggcacgcaa   3120
aaccagatcg cttggtacgt tttaggggta aaccagtaat atattttttg atgacgtgac   3180
acaattctag aagtagtcat ttcctgattc cttaggaaaa gggaaggtta tttcgtccca   3240
ttttatatat catagttaca cattcttata tttaatagta acaatttaac tttaaaatac   3300
ctcttttacc cttaatgaaa tgattatag cgaaacacat atccattgct cagtttacac   3360
cataaatttc aaaaatattc ttaaatattg tgttcagtca aacatcatca cataaattga   3420
gacattgaga catagaggag tactatgtta attttctgat ggtgatatgc tttaccaggt   3480
ctagttgggt ttcaaatgtc ttgcgagtta atagaagtag ctatccacaa tgtcaagtga   3540
taaaaacaaa ctggaagtct cggcgaggaa caatcaaatc tagccagcag agagatggat   3600
cagttactag gtacttcgat ttcattgtga ttggtagtg aattgctgc cttcgatatg    3660
cacttgaggt tgccaagcat ggaactgtgg ctgtgataac caaggctgag ccacatgaga   3720
gtagcactaa ctatgctcaa ggtggtgtaa gtgctgtgct ctgcccttg gattcagtgg    3780
agaaccacac acaagataca attgtggcag gtgcttacct ctgtgataag gagactgtta   3840
aagtaagtc acacgaatat atacagttta atttggagtc tatttccccc cttttgcttt   3900
tgctataagt gtatctctcc tttaatttct ccaggtagtg tgtactgaag gacctgagag   3960
aattagagaa ctgatcgcta taggtgcttc attcgatcat ggggaggacg gaaatctgga   4020
tctagccagg gaaggaggcc actcccatcg tcgaattgtc catgctgctg atatgactgg   4080
cagagagatt gaaagagcct tattagaggc agtgtttaag aatcctaata tacatgtgtt   4140
tcaacaccat tttgctatcg attttgttgac cactcaggtt agttttattag tgtgctatag   4200
ttgagtaaag gtcgcaattg aactattcag caaggatttg atgttgtaat ttgtatggca   4260
aatgcaggat ggttctgacg tagtatgtca tggcgttgat actatacaca cggaaacgaa   4320
ggaggtaagt aacagttgct ttcactcatg ttgacttttc aacattcttc aaaatgacat   4380
aaattgattt tcttacttgt gtattttagg ttataagatt cattttcaaa gtgacttttga   4440
tagcatcagg tggagttgga catatctatc caagtactac taatccgacg gtatggtttc   4500
aatatctttt cctccaaaat cttgttagtt atgattaatg tcatgctcca aaaataaaag   4560
atctggacat ggcactcgat cgatgctttg aaacttgtga cagagcgaac caacatccat   4620
tacatactta gtgcaattag aaatatgagc tcgctgccct aaatgcctaa aaaaggattc   4680
tgttttata ctttgaccat ttgtgccaac agaaaagttt aaccctgttg aatgtgggct     4740
tgtttaactt tctaattcat attgacatta tgattatagg ttgcaactgg tgatggaatg   4800
gctatggctc atcgagctca agctgtaatt ccaacatgg agtaagtaat cctcagtagc     4860
attatttta ttgtacaata tctctgcctc tgcttagtg agttttgtgc tgtaaaatct     4920
gctgacctag atttcatcct ttttttttt ctttcctgat ttctgcatct tgttcagcat   4980
ttcgttcaga atttgcactt tcgactaaaa acacaagggt gtgttcaaaa atttgcatta   5040
ttaataacaa ttctcttcct cgtgttgcca ggtttgtgca attccaccca actgccttgg   5100
ctgatgaagg gcttcccaac ataccaagtg ccagagaga tgcttttttg ataactgaag    5160
ctgtcagagg tgatggaggc atcctttata acttagatat ggaaagattt atgccaatgt   5220
atgatgaaag agcagaactt gccccgagag atgtggtagc aagaagtata gatgaccagc   5280
tcaaaaagcg tggcgaaaag tatgttcttc ttgatatcag tcacaagccc agagagaagg   5340
ttctgtccca ttttcctaat atagctgctg agtgtctccg ccatgggtta gacataacac   5400
agcagccgat tccggtggtt cctgctgctc actacatgtg tggtggagtc cgtgctggac   5460
tcgagggtga gactaatgtg caaggtcttt atgtggcagg tgaagttgca tgtactggtt   5520
tacatggtgc aaaccgactt gctagcaact cattgcttga agcactagtg tttgcacgaa   5580
gagctgtaca gccttcaatt gatcatgtga acgtgtctag aattgataac ggtgcatcaa   5640
gttggtggcc gcggcctgta gccccctgg cactaggaga tacagtactt aacaaagtca   5700
tccgtcggac aagggaagtg aggaaagaac tacagtcaat catgtgggaa tatgttggaa   5760
ttgttaggtc tacctcaaga ctaaatactg ctgagaagag aatcaaagag ttggagttgg   5820
aatgggaaac atacctgttt cagcatggct gggaaccaac aatggttgga gtagaggctt   5880
gtgagatgag gaatctcttc tgttgtgcca acctggtagt tagcagtgct ctttctcgac   5940
aagagagtcg tgggcttcac tacaccactg attttcctca tgttgaggaa agcgagtggt   6000
tgccaacggt tatctttcct tctcagcgaa atagcacatg gagcacacgg caattacacg   6060
cgcagccgat aagttagata tctcttacct atttgccatt cttcctgcca aaacatctcc   6120
agtgcaggac atgatttgtc gatttaccg ggttgcaggg gtgtatctat cggaaggggt   6180
atgggttcat atgaacacat actcctctcc atagactatg tataataatg tatatttctt   6240
caattgtatt taaatatgca agtgtgtcag ccaagctcaa agttccaat aattattggg     6300
tacatcttta caagtgaaat tgtgatttta aatcccatgt ctattttgtc gttttttcct   6360
ttatctttc cgccgaaagt caaatctcac atttctcttg tggttttcc tttctttttcc    6420
tataaatggg tctacccatg ataaaagaaa tttcatattt ttgttttagt aatttctgaa   6480
tgcaggtttt gacaatttat taaaaacata tcacaggtca cgagctttaa ttagttaagt   6540
aagcaacttg ttaaatgtgc cagacctgat tcttagtgca attcacccct tccattttc    6600
```

-continued

```
taggatagtt ctcctagcca gtctgtaact tgctctgttc atggcaaatt acaagtgcgt   6660
gatagtttgg agaccatagg aaccctgaac tcgaaattgg ggaaattaga gaaaaggcat   6720
cgaaaattaa ccataaatca gaacaaaata cctcaaacca tgagtacctc catgaatttt   6780
gctctaaatc atgtaggttt tgatcaaatt tagctacaaa cttgcgttct ttggagagag   6840
agaattggaa agttaagtcc attctagaag aaaatgacaa acatggtccc taatctattg   6900
ggatttgatc attttggtcc ttaatgtatg cacttgacct atatagtcct taacctattt   6960
taaaaggtga ctcttttggt ttgaaacact ataactaacg gtatagttac tagcacccac   7020
tgggcatatg gcttataagc atcaatagac gtagccttgg aaaggaatgg aaattttagg   7080
gccttgtgag ggtagagtaa tccttggtaa tggacatatt tttcttttt ataattaaat    7140
gatattactg aatggtattc caaacatgtc aattgttcct ttttataagg cacataggtg   7200
gggtaatccg gaattgtata gtcgggtata acttctcgag tgatgagatg tttcagagtt   7260
taagtaattg aattctcata tatgggataa gtattcactt tagtgtaaat cttacttcca   7320
gttaagacag gatattaagc gaccgaagaa tacggccaaa agcgggggaa gctagaagcg   7380
aaaaaatatc tcgcttgagt cctccaaagg aagataagag attaatgt tagtaagaaa    7440
tagataggag gataagtatg agaaatgttt aacaattata agctgaagta tggtattatg   7500
acaaggttcg taatcaagaa aaagtgaagg caagttttaa ttataaagag gtatgagtcg   7560
taatcacgag aagtgaattt tcgacttcaa taagagttat caaaagacca atctagcccc   7620
tggattaaga aataccaata ttaggtagta acctaagata acgagatgca agttagaaac   7680
tcaaaggatt tctgtaatag ttggcattgc gacatttaca aagtgaatga tcaggcagta   7740
aaagggtgaa tgactatgga acaacctttg agggttagta gaaagagctc tccctgagag   7800
aagcgtcata agcaaagtta agctcatcaa ggtcgagcat accagttatg agtatacaat   7860
actacataca tataagttat ccaattgctt tagtagggaa gattacccca aggcaagtta   7920
taagccactg aaattgcaaa gaattgcaaa aggtggagag ttaacgatgt gacctctaca   7980
agagtggaat tcaagagcat aaggagttaa ttattctccc gagggaagat cgtatgataa   8040
agtatcgagg caaaattatg aggttcgctt agtaacggag cggtaagaag gattacgaca   8100
agaggtttga aaggaataag atttgtactta cttagaccct acaaatgtgt aacgactcta   8160
atgcataagt acaaacggta gagaaaatgc agtaatgact tcctgactag aggtaccaat   8220
tgatggtaaa taaaactagg cagttgatac tcaggaagct agtgtgaggg gtaaattaag   8280
gcaaaaacat agcctcaaga ggagttactt agattttacc tatgaagata attgattgag   8340
caatcagtga ttagcttatg aagggtctag ttatgggtta gacgacaaaa ctcagacgag   8400
tcattagatc atgcaaaatt acatgttgga tcaaaacgta caaagtttca gcctcgcaag   8460
tgcatgatcg cgactctcag aaagtatttc aagacataag caatggtagg tgaaattcca   8520
tattatcttt tagaaaatcg gaaggagccc attgagctta aaatatgagg gaggtgttca   8580
aaagttgtga tcagaagtaa tattatagta aaggagaggt gaaaaacaat tagatattat   8640
tttagatagt tcaaaatcac ctaaagttct agggagtata tgatgtaatg agctcgcagt   8700
cagatatgaa caagagaatc ttttctaagt gtgtatacga ctaaaatcgg agagtccgat   8760
tttatgatcg ttatgacatt ccacggctca gcttcagaag gcctgaggca cagttcgaag   8820
ttcgaccccg aggggttctca atgcccaacc tcggggtaac gtaaatcgac gactatcttg   8880
cataagcaaa aagttcccaa ggcgcgtgct caaagctgac aacacctgca aatatagtat   8940
aagttcgtac tgtggcatta aatagctgta ccaggttcat atctttgtaa taaatgcata   9000
tgtactatgt tggggttctc cctcctatat aaaggggacc cttgttattt ttttcataca   9060
tgatatttaa tacaaga                                                  9077
```

```
SEQ ID NO: 37          moltype = DNA   length = 7038
FEATURE                Location/Qualifiers
source                 1..7038
                       mol_type = genomic DNA
                       organism = Nicotiana tabacum
SEQUENCE: 37
cagatttggt taattttggt aagagtgaac tcgtgagtga atgggtgttc atatttggta     60
acttttaccc gatttcgaga catgaccccg gggaggcttt ttaggacgga tttcagattt    120
tttattaaaa tcttgatttc attaattaga ttagtctatt atagttgtat ttatgatatg    180
taattaattt tggctagatt tgggccattc agagtcagat attcatgaaa aaggcattgt    240
tactgattga ttgagcttgg ttcgaggtaa gtggcttgcc taaccttgtg tgggggaact    300
ccccttagga tttggtacta cttttgatat atgagctcgtc tgtatgtgag gtgacaagtg    360
cgtacacggg ctattattgc aaaactccat tttcattaag taatataaact gtcttccttt    420
aactgagcta cactagcata ttaatttatc ctgtttagtc tagaacaaca tgtctacgtg    480
tcttaattgc ttatgtgaac tctgtgcatc atgcttagta aattttctgc ttctttcttg    540
actgatactt agtctaaatc gtaagatttc gtgatgtagt tgtatttcta ttgtttgcgc    600
tgtatattta ctttgggact acagagcgat atttcggtag atcccccatt ctgcatattt    660
actttgggat tacggaacgg tattccggta gatccctctg tcatgtatat ttactttggg    720
actacaaaac ggtattccgg tagatccccc tgctctgcat atttactttg ggactatagaa   780
acggtattcc ggtagatccc cctgctctgc atatttactt tgggactacg gaacggtatt    840
ccggtaaatt cccccatttt ttgcacattt acatttgggta ctacgagacg gtatcgtcct    900
agatcctcta ttgttatttc tgtgtactga gttgttgact tgctatgatt tcattcttgt    960
taaatttcag tacttatttt tactgcaata ttcattctg tcttagttta ttatatatat    1020
accatgacct gatctcgtca ctactcgacc gaggttaggc ttggcactta ttgggtaccg   1080
ttgtggtata ctcatgctac tcttctgcac atatttttg tgtgcagatc caggtgctct   1140
ttatcagtga gccgggacag cttttggagac ttcaaggtat atcttccgcg tccgcagacc  1200
tcggagtccc cttctactct tccccacgtc cattatcttc tgtatttcc ttttgttaga   1260
ctctgaagta tagagacact agattttcct tctgtgttt gtaacttacg atattccggg    1320
ttttgggaga gttatgtaca tttcgagagt gaccgtggta tatgccgagc gacatcttaa    1380
tttcttattt agaatctacc tgtaaattgc tagttttaat gttttcgttt catttccgca   1440
aaagtgtttag gcttacctag tcgtagagac taggtgtcgt cacgacggtt caagaaggga   1500
gaacttgggt cgtgacacct aatattatt gtgccatttc gaaccaaaat attaagtaat   1560
ttttattata attcaaacta ttaatagtaa atttatgttt tttttgtata taacaagaa   1620
aaagagtaat ctgatcagga aaaaacatag attcaaatta gaactcatga tattactgtt   1680
caaactgtaa taactttacc atttgaattt ttatgactat tttgaatgtc aagtaaacat   1740
ttcaaggtac aataaaaaga aagagcagac aattggtatc ttcttagaa atatttgttt    1800
```

```
ctatattttc aggtccactt ctaatgtaac acatatttttt tcttatgtta aagaagaca   1860
tctcatctta tttaatacta ttaacaaatg aactatgaaa aatgcaaact ctttgattgt   1920
tcacaacttg acgaggttta aataaattat aatctttgtc ttaaatatac gcgctaagaa   1980
actaccaaaa tgtgttgcct atgaattttg tgctaccaaa aatagaatat gaggaaataa   2040
caactcacaa acacaaagaa aattaagttg atgaaatatt gtccacctttt tatttcttct   2100
tcattaatgt ttaatcccaa caacataagt ttaaaaccaa atgattaact caaaaatgca   2160
atagttttta ttgaataaag atgcatatga aatatccgta tttaaacata ttatttaaat   2220
taactaaaag atctttgcaa aacaattgga gtaatacaat taaggaaatt attttttgtaa  2280
taaaatgttg ggacatgctc agcagcatgg ccagccctcc tgtagtatac atatatgcag   2340
caattaagta gtccttaatg attgaattac attacaccta aacaaatgca taaaccacgt   2400
ggtatttgca agtgaacagc tgaaagtcca tagcacctca aaaaagacta aggtaacgtg   2460
ggtatcaata tatgcagcaa ttaagtaata aggaccgaat cacatagtat ccctaaacaa   2520
atataagtga tacatagtat cccctaaaca aatataagtg ataaggtacg aatcactaaa   2580
caaatgcata aaccacgtgg gcgtttggaa gtgaagtcat aagcacctct aaaaattgatc  2640
aaattcacaca gttatcccta aacaaatgca taataccgaa actacccctg cacgaccata   2700
atacttcact tatatagtta tggcttctgc ttccttggcc agcaatcatt tcatctgtaa   2760
cttcgaattc cagttccatt ttcacttgat cgtacttcga agcgccatat tttccccttt   2820
aagctaaggt aattgtattg tttaacaaat ttacatgttc caaatgaata ttaattgtta   2880
attcctatta tcatcctgaa acaaaatttt ctctatatgt agcctttacg tactatattc   2940
gctcatgctt taatgtgtaa tgcataacaa gatttttaccct taaatatcca gatcgatcat  3000
atggcaactg gtatcgcttc aggatgcgga cagttacact tgaggaagcc tgtctacttg   3060
aggaatagct atggaaataa agctcactgt cattccaata tgattctcaa cggcacgcaa   3120
aaccagatcg cttggtacgt tttagggggta aaccagtaat atcttttttca tgaaatgatt  3180
aatagtcaaa ctattatcca tggctcactt tacgcaataa attttaaaag tattcttaaa   3240
catcgcgcta ataatctgat ggtgatatgc ttttccaggt ctagttgggt ttcaaatgtc   3300
ttgcgagtta atagaagtag ctatccagaa tgtcaagtga tcaagacaaa ctggaagtct   3360
agccgaggaa caatcaaatc gtgccagcag agagatggat cagttactag gtacttcgat   3420
ttcactgtga ttggtagtgg aattgctggc cttcgatatg cacttgaggt tgccaagcat   3480
ggaactgtgg ctgtaataac caaggctgag ccacatgaga gtagcactaa ctatgctcaa   3540
ggtggtgtaa gtgctgtgct ctgccctttg gattcagtgg agagccatat gcaagataca   3600
attgtggcag gtgcttatct ctgtgataag gagactgtta gagtaagttc acacagaata   3660
tattcagttt ggagactata aatttcccccc tttttgccttt actataagtg tatctctcct  3720
ttaatttctc caggtagtgt gtactgaagg acctgagaga attagagaac tgatcgctat   3780
gggtgcttca ttcgatcatg gggaggacgg aaatctggat ctagccaggg aaggaggcca   3840
ctcccatcgt cgaattgtcc atgctgctga tatgactggc agagagatag aaagagctct   3900
attagaggca gtttttaaga atcctaatat acatgtgttt caacaccatt ttgctataga   3960
tttgttgacc actcaggtta gttattagt gtgaaaaaag ttttttctata gttgtgtaaa   4020
ggtggcaatt gaactgttca gtaaggattt aatgttgtaa tttgtatgcc aaatgcagga   4080
tggttctgac atagtatgtc atggcgttga tactatacac acggaaacga aggaggtaag   4140
caccagttgc ttttcactcat gttgactttt gaacatttct tcaaaaggac acaaattgat   4200
tttatggct tctgcgctct tacttgtgtt ttttaggtta taagattcat ttcaaaagtg    4260
actttgctgg catcaggtgg agttggacat atctatccaa gtactactaa tccgacggta   4320
tggggtttcaa tatctttttcc tacaaaatct tgttagttat aatcgctccaaa acgctccaaa 4380
aataaatgag ctggacatgg cactcgaacg atgccttgaa actagtgaca gagcgaacca   4440
acatccatta tatactcccct gccctaaatg cctaaaaaag gattctgggt agtcgaataa   4500
cagatgattc tctgcctgga agtgtgaatt cttattctat acacccataa tttatgtaca   4560
gtaaaagcaa gatacatggt tcaaagtttt actaattacc cgggtcaggc atctgctgtg   4620
gctctgtaat tggtggttgg gtcaattctg tttttatact ttgaccatttt gtgccaacag  4680
aaaagtttaa ccctgttgaa tgtgggcttg tttaaatttc taattcatat tgacattatg   4740
atcataggtt gcaactggtg atggaatggc tatggctcat cgagctcaag ctgtaatttc   4800
caactggag taagtgatcc tcagttgcat tatttttatt gtacaatatc tctgcctctg    4860
ctttagtgag ttttgtgctg taaaatctgc tgatctagat ttcatccttt ttttcccccct  4920
gatttctgca tcttgttcag catttcgttc agaatttgca ctttcgacta aaacacaag    4980
ggtgttaaaa aatttgcatt attaataacg attctcttcc tcgtgttgcc aggttttgtgc  5040
aattccaccc aactgccttg gctgatgaag gccttcccaa cataccaagt gccagagaga   5100
atgctttttt gataactgaa gctgtcagag gtgatggagg catccttttac aacttagata   5160
tggaaagatt tatgccaatg tatgatgaaa gagcagaact tgccccgaga gatgtggtag   5220
caagaagtat agatgaccag ctcaaaaagc gtggcgaaaa gtatgttctt cttgatatca   5280
gtcacaagcc cagagagaag gttctttctc attttcctaa tatagctgct gagtgtctca   5340
gccatgggtt agacataaca cagcagccga ttccggtggt tcctgctgct cactacatgt   5400
gtggtggagt ccgtgctgga ctcgagggtg agactaatgt gcaaggtctt tatgtggcag   5460
gtgaagttgc atgtactggt ttacatggtg ctaaccgact tgctagcaac tcattgcttg   5520
aagcactagt gtttgcacga agagctgtac agccttcaat tgatcatgtg aacgtgtcta   5580
gaattgatca cggtgcttca agttggtggc cgcggccctg agccccccatg gtactaggag  5640
atacagtact taacaaagtc atctgtcgga caagggaagt gaggaaagaa ctacagtcaa   5700
tcatgtggga atatgttgga attgttaggt ctaactcaag actaaacact gctgagaaga   5760
gaatcagaga gttggagttg aatgggaaaa catacctatt tcagcatggc tgggaaccaa   5820
caatggttgg agtagaggct tgtgagatga ggaatctctt ctgttgtgcc aacttggtag   5880
ttagcatgc tctttctcga catgagagtc gtgggcttca ctacaccact gattttcctc   5940
atgttgagga aagcgagagg ttgccaacgg tcattttttcc ttctcagcga aataactcat   6000
ggagctcacg ccaattacac gcgcagccga taagttagat atctctttcc tatttgccat   6060
tcttcctgcc aaaacatctc cagtgcagga catgatttgt cgattttacc gggttgcagg   6120
ggtgtatcta ttggaagggg tatgtgttca catgaacata tactcttttc cctaaattat   6180
gtataataat atatatttct tcaatgtttt ttaagtatgt aagtgtgtca gtcaagctca   6240
aagagttcta tcgttcaata attattaggt gtatcttaac aagtaaaatt gggattttaa   6300
atcccatgtc tattttgtgg ttttttcccgt tatctttttcc gttgaaggtt aaaatctcac  6360
atttctcttg ttggttttttc ctaaaaatgt gtctacccac gaggatgggc atgtcttgtg   6420
tctcctattg ccttttagtt aagtattttt ttttcttggg aaaataacag ttttagttaa   6480
ctatcaaaga agagataaca acttattaca aattatatgc gagaagcacg gtgcctgtca   6540
```

```
tgcttcagaa agtcataatg gcaaatcaaa attatcgccc tcctaggtca aacatcaata    6600
tggtttcatt cttcttcttc acaaatccat aagtcaatga cacacaatag gttcattaat    6660
gattcagaga acatcaatc cagcgagggg tcgtttggtt tgaatacggc ttatgacggg     6720
attaggtatg ctaaaattag ttatgttggg attagttatc ctgatattat tttttatcca    6780
ctgttttggta tgttaacgat cgggtacccc taagtaattt aatgaaaagg aatcaacaat   6840
tgtttcaaca agaacaaaac acctattggt gcttgagaaa atatagatgt ctcgggcatt    6900
aaatccatga taaaggctaa tgcgtacctc aatcttttag ctcttccatt acttaaaaga    6960
gtttcccct actgtacaaa gtaaatgagg ggaataaaga aatccataaa agaaatttcc     7020
tatttatggt ttagtaat                                                  7038
```

```
SEQ ID NO: 38              moltype = DNA   length = 18
FEATURE                    Location/Qualifiers
misc_feature               1..18
                           note = Synthetic Primer
source                     1..18
                           mol_type = other DNA
                           organism = synthetic construct
SEQUENCE: 38
gctgctgagt gtctccgc                                                    18

SEQ ID NO: 39              moltype = DNA   length = 21
FEATURE                    Location/Qualifiers
misc_feature               1..21
                           note = Synthetic Primer
source                     1..21
                           mol_type = other DNA
                           organism = synthetic construct
SEQUENCE: 39
tccaccacac atgtagtgag c                                                21

SEQ ID NO: 40              moltype = DNA   length = 30
FEATURE                    Location/Qualifiers
misc_feature               1..30
                           note = Synthetic Probe
source                     1..30
                           mol_type = other DNA
                           organism = synthetic construct
SEQUENCE: 40
tgggttagac ataacacagc agccgattcc                                       30

SEQ ID NO: 41              moltype = DNA   length = 23
FEATURE                    Location/Qualifiers
misc_feature               1..23
                           note = Synthetic Primer
source                     1..23
                           mol_type = other DNA
                           organism = synthetic construct
SEQUENCE: 41
gaggttgcca acaatcattt ttc                                              23

SEQ ID NO: 42              moltype = DNA   length = 21
FEATURE                    Location/Qualifiers
misc_feature               1..21
                           note = Synthetic Primer
source                     1..21
                           mol_type = other DNA
                           organism = synthetic construct
SEQUENCE: 42
tgcgcttgac aagttttagc a                                                21

SEQ ID NO: 43              moltype = DNA   length = 29
FEATURE                    Location/Qualifiers
misc_feature               1..29
                           note = Synthetic Probe
source                     1..29
                           mol_type = other DNA
                           organism = synthetic construct
SEQUENCE: 43
ctcacggcaa ttacacaggc agcagatat                                        29

SEQ ID NO: 44              moltype = DNA   length = 29
FEATURE                    Location/Qualifiers
misc_feature               1..29
                           note = Synthetic Primer
source                     1..29
                           mol_type = other DNA
                           organism = synthetic construct
SEQUENCE: 44
agatatctct tacctatttg ccattcttc                                        29
```

```
SEQ ID NO: 45           moltype = DNA   length = 24
FEATURE                 Location/Qualifiers
misc_feature            1..24
                        note = Synthetic Primer
source                  1..24
                        mol_type = other DNA
                        organism = synthetic construct
SEQUENCE: 45
ccataccct tccgatagat acac                                             24

SEQ ID NO: 46           moltype = DNA   length = 26
FEATURE                 Location/Qualifiers
misc_feature            1..26
                        note = Synthetic Probe
source                  1..26
                        mol_type = other DNA
                        organism = synthetic construct
SEQUENCE: 46
tgccaaaaca tctccagtgc aggaca                                          26

SEQ ID NO: 47           moltype = DNA   length = 20
FEATURE                 Location/Qualifiers
misc_feature            1..20
                        note = Synthetic Primer
source                  1..20
                        mol_type = other DNA
                        organism = synthetic construct
SEQUENCE: 47
ctaagggtgc tgccagcttt                                                 20

SEQ ID NO: 48           moltype = DNA   length = 22
FEATURE                 Location/Qualifiers
misc_feature            1..22
                        note = Synthetic Primer
source                  1..22
                        mol_type = other DNA
                        organism = synthetic construct
SEQUENCE: 48
gtcaagcact ggagcatatc ca                                              22

SEQ ID NO: 49           moltype = DNA   length = 26
FEATURE                 Location/Qualifiers
misc_feature            1..26
                        note = Synthetic Probe
source                  1..26
                        mol_type = other DNA
                        organism = synthetic construct
SEQUENCE: 49
atcatgaacc atccaggaca gattgg                                          26

SEQ ID NO: 50           moltype = DNA   length = 30
FEATURE                 Location/Qualifiers
misc_feature            1..30
                        note = Synthetic Primer
source                  1..30
                        mol_type = other DNA
                        organism = synthetic construct
SEQUENCE: 50
taagagacag acctcagaat tgggtgtgcc                                      30

SEQ ID NO: 51           moltype = DNA   length = 30
FEATURE                 Location/Qualifiers
misc_feature            1..30
                        note = Synthetic Primer
source                  1..30
                        mol_type = other DNA
                        organism = synthetic construct
SEQUENCE: 51
taagagacag gatagagagg agagataggc                                      30

SEQ ID NO: 52           moltype = DNA   length = 30
FEATURE                 Location/Qualifiers
misc_feature            1..30
                        note = Synthetic Primer
source                  1..30
                        mol_type = other DNA
                        organism = synthetic construct
SEQUENCE: 52
```
taagagacag atgctctaga agttgcaaag 30

SEQ ID NO: 53        moltype = DNA  length = 29
FEATURE                Location/Qualifiers
misc_feature       1..29
                      note = Synthetic Primer
source                 1..29
                      mol_type = other DNA
                      organism = synthetic construct
SEQUENCE: 53
taagagacag ttctcccgtg ccttctcac 29

SEQ ID NO: 54        moltype = DNA  length = 30
FEATURE                Location/Qualifiers
misc_feature       1..30
                      note = Synthetic Primer
source                 1..30
                      mol_type = other DNA
                      organism = synthetic construct
SEQUENCE: 54
taagagacag ttttccatgt aaacatttgc 30

SEQ ID NO: 55        moltype = DNA  length = 30
FEATURE                Location/Qualifiers
misc_feature       1..30
                      note = Synthetic Primer
source                 1..30
                      mol_type = other DNA
                      organism = synthetic construct
SEQUENCE: 55
taagagacag tgacatccct cataaatgaa 30

SEQ ID NO: 56        moltype = DNA  length = 30
FEATURE                Location/Qualifiers
misc_feature       1..30
                      note = Synthetic Primer
source                 1..30
                      mol_type = other DNA
                      organism = synthetic construct
SEQUENCE: 56
taagagacag gggagtgcta atctgatatg 30

SEQ ID NO: 57        moltype = DNA  length = 32
FEATURE                Location/Qualifiers
misc_feature       1..32
                      note = Synthetic Primer
source                 1..32
                      mol_type = other DNA
                      organism = synthetic construct
SEQUENCE: 57
taagagacag ggcaatagaa agaagataat ac 32

SEQ ID NO: 58        moltype = DNA  length = 30
FEATURE                Location/Qualifiers
misc_feature       1..30
                      note = Synthetic Primer
source                 1..30
                      mol_type = other DNA
                      organism = synthetic construct
SEQUENCE: 58
taagagacag ttattcctcc aatgagaacg 30

SEQ ID NO: 59        moltype = DNA  length = 30
FEATURE                Location/Qualifiers
misc_feature       1..30
                      note = Synthetic Primer
source                 1..30
                      mol_type = other DNA
                      organism = synthetic construct
SEQUENCE: 59
taagagacag taccaatcac cgcgaaatcg 30

SEQ ID NO: 60        moltype = DNA  length = 31
FEATURE                Location/Qualifiers
misc_feature       1..31
                      note = Synthetic Primer
source                 1..31
                      mol_type = other DNA
                      organism = synthetic construct

```
SEQUENCE: 60
taagagacag gtttagtata ctcttttgaa g                                     31

SEQ ID NO: 61            moltype = DNA  length = 30
FEATURE                  Location/Qualifiers
misc_feature             1..30
                         note = Synthetic Primer
source                   1..30
                         mol_type = other DNA
                         organism = synthetic construct
SEQUENCE: 61
taagagacag ctatagcaaa attttcacac                                       30

SEQ ID NO: 62            moltype = AA   length = 644
FEATURE                  Location/Qualifiers
source                   1..644
                         mol_type = protein
                         organism = Nicotiana sylvestris
SEQUENCE: 62
MATGIASGSG QLHLRKPVYW RSSYGKAHCH SNAILNGMQN QIPWSYWVSK FLRVHRSNYS       60
QCQVKTNWKS HTGTINSCQR DGSTRYFDFA VIGSGIAGLR YALEVAKHGT VAVITKAEPH      120
ESNTNYAQGG VSAVFCPMDS VESHMQDTIV AGAYLCDEET VRVVCTEGPE RIRELIAMGA      180
SFDHGEDGNL HLAREGGHSH RRIVHAADMT GREIERALLE AVFKHPNIHV FQHHFAIDFL      240
TTQDRSDIIC HGVDAINTET QEVIRFISKV TLLASGGAGH IYPSTTNPPV ATGDGMAMAH      300
RAQAVISNME FVQFHPTALA DEGLPNRPSA RENAFLITEA VRGDGGILYN LDMERFMPMY      360
DKRAELAPRD VVARSIDDQL KKRGEKYVLL DISHKPREKV LSHFPNIAAE CLRHGLDITQ      420
QPIPVVPAAH YMCGGVRAGL EGETNVQGLY VAGEVACTGL HGANRLASNS LLEALVFARR      480
AVQPSIDHVN VSRIDHCASS WWPRPVAPVV IGDTVLNKVI RRTREVRKEL QSIMWEYVGI      540
VRSTSRLTAA EKRINELELE WETYLFQHGW EPTMVGLEAC EMRNLFCCAN LVVSSALSRH      600
ESRGLHYTID FPHVVESKRL PTIIFPSQRN SSWSSRQLHR QQIC                       644

SEQ ID NO: 63            moltype = AA   length = 644
FEATURE                  Location/Qualifiers
source                   1..644
                         mol_type = protein
                         organism = Nicotiana tabacum
SEQUENCE: 63
MATGIASGSG QLHLRKPVYW RSSYGKAHCH SNAILNGMQN QIPWSYWVSK FLRVHRSNYS       60
QCQVKTNWKS HTGTINSCQR DGSTRYFDFA VIGSGIAGLR YALEVAKHGT VAVITKAEPH      120
ESNTNYAQGG VSAVFCPMDS VESHMQDTIV AGAYLCDEET VRVVCTEGPE RIRELIAMGA      180
SFDHGEDGNL HLAREGGHSH RRIVHAADMT GREIERALLE AVFKHPNIHV FQHHFAIDFL      240
TTQDGSDIIC HGVDAINTET QEVIRFISKV TLLASGGAGH IYPSTTNPPV ATGDGMAMAH      300
RAQAVISNME FVQFHPTALA DEGLPNRPSA RENAFLITEA VRGDGGILYN LDMERFMPMY      360
DKRAELAPRD VVARSIDDQL KKRGEKYVLL DISHKPREKV LSHFPNIAAE CLRHGLDITQ      420
QPIPVVPAAH YMCGGVRAGL EGETNVQGLY VAGEVACTGL HGANRLASNS LLEALVFARR      480
AVQPSIDHVN VSRIDHCASS WWPRPVAPVV IGDTVLNKVI RRTREVRKEL QSIMWEYVGI      540
VRSTSRLTAA EKRINELELE WETYLFQHGW EPTMVGLEAC EMRNLFCCAN LVVSSALSRH      600
ESRGLHYTID FPHVVESKRL PTIIFPSQRN SSWSSRQLHR QQIC                       644

SEQ ID NO: 64            moltype = AA   length = 645
FEATURE                  Location/Qualifiers
source                   1..645
                         mol_type = protein
                         organism = Nicotiana tabacum
SEQUENCE: 64
MATGIASVSG QLHLRKPVYW RSSYGKAQCH SNVILNGMQN QIPWSYWVSK FLRVHRSNYS       60
QCQVKTNWKS HSGTINSCQR DGSTRYFDFA VIGSGIAGLR YALEVAKHGT VAVITKAEPH      120
ESNTNYAQGG VSAVLCPMDS VESHMQDTIV AGAYLCDEET VRVVCTEGPE RIKELIAMGA      180
SFDHGEDGNL HLAREGGHSH RRIVHAADMT GREIERALLE AVFKHPNIHV FQHHFAIDLL      240
TTQDGSDIVC HGVDTINTET QEVIRFISKV TLLASGGAGH TYPSTTNPPV ATGDGMAMAH      300
RAQAVISNME FVQFHPTALA DEGLPIRPTR TRENAFLITE AVRGDGGILY NLDMERFMPM      360
YDERAELAPR DVVARSIDDQ LKKRGEKYVL LDISYKPREK VLSHFPNIAA ECLRHGLDIT      420
QQPIPVVPAA HYMCGGVRAG LEGETNVHGL YVAGEVACTG LHGANRLASN SLLEALVFAR      480
RAVQPSIDHM NVSRIDHGAS SWWSRPVAPM LLGDTVHGKV IHRTREVRKE LQSIMWEYVG      540
IVRSTSRLTA AEKRIRELEL EWETYLFQHG WEPTMVGVEA CEMRNLFCCA NLVVNSALSR      600
HESRGLHYTI DFPHVEESKR LPTIIFPSQR NSSWSSRQLH RQQIC                      645

SEQ ID NO: 65            moltype = DNA  length = 1935
FEATURE                  Location/Qualifiers
source                   1..1935
                         mol_type = genomic DNA
                         organism = Nicotiana sylvestris
SEQUENCE: 65
atggcaactg gtatcgcttc aggaagcgga cagttacatt tgaggaagcc tgtctactgg       60
aggagtagct atggaaaagc tcactgtcat ccaatgcga tcctgaatgg catgcaaaac      120
cagatccctt ggtcttattg ggtttccaaa ttccttgcgag ttcatagaag taactactca      180
caatgtcaag tgaaaacaaa ctggaagtct cacaccggaa caatcaattc ttgccagaga      240
gatggctcaa ctaggtattt tgattttgct gtgattggta gtggaattgc tggccttaga      300
tatgctctag aagttgcaaa gcatggaact gtagctgtga taaccaaggc tgagcctcat      360
```

```
gagagtaaca ctaactatgc tcaaggtggt gtaagtgctg tgttctgccc tatggattca    420
gtggagagcc acatgcaaga cacaattgtg gcaggtgctt acctctgtga tgaggagact    480
gttagagttg tgtgtaccga aggacctgag agaattagag aactgattgc tatgggtgct    540
tcattcgatc atggggagga cgggaatctg catctagcca gggaagggggg ccactcccat    600
cgtcgaattg tccatgctgc tgatatgact ggcagagaga tagaaaggg cctattagag     660
gcagttttta agcatcctaa tatacatgtg tttcaacacc attttgctat agatttttg     720
accactcagg atcgttctga cataatatgt catggcgttg atgctataaa cacggaaacg     780
caggaagtta taagattcat ttcaaaagtg actttgctgg catcaggtgg agctgggcat    840
atctatccaa gtactactaa tccaccggtt gcaactggag atggaatggc tatggctcat    900
cgagctcaag ctgtaatttc caacatggag tttgtgcaat tccatccaac tgccttggct    960
gatgaaggcc ttcccaacag accaagtgcc agagagaatg ctttttttgat aactgaagct   1020
gtcagaggtg atggaggcat cctttacaac ttagatatgg agagatttat gccaatgtat   1080
gacaaaagag cagagcttgc cccgagagat gtggtagcaa gaagtataga tgaccagctc   1140
aaaaagcgtg gcgaaaagta tgttcttctt gatatcagtc acaagcccag agagaaggtt   1200
ctgtctcatt ttcctaatat agctgctgag tgtctccgcc atgggttaga cataacacag   1260
cagccgattc cggtggttcc tgctgctcac tacatgtgtg gtggagttcg tgctggactt   1320
gagggtgaga ctaatgtgca aggccttat gtggcaggtg aagttgcatg tactggttta   1380
catggtgcta accgacttgc tagcaactcg ttgcttgaag cactagtgtt tgcacgaaga   1440
gctgtacaac cttcaattga tcacgtgaat gtgtctagaa ttgatcactg tgcttcaagt   1500
tggtggccgc gacctgtagc cccagtggta ataggagata cagtacttaa caaagtcatt   1560
cgtcggacaa gggaagtgag gaaagaacta cagtcaatca tgtgggaata tgttggaatt   1620
gttaggtcta cctcaagact aaccgcagct gagaagagaa tcaatgagtt ggagttggaa   1680
tgggaaacat acctatttca gcatggctgg gaaccaacaa tggttggact agaggcttgt   1740
gagatgagga atctcttctg ttgtgccaac ctggtagtta gcagtgctct ttctcgacac   1800
gagagtcgcg ggcttcatta caccattgat tttcctcatg ttgtgaaag caagaggttg   1860
ccaacaatca ttttttcctc acagcgaaat agctcgtgga gctcacggca attacacagg    1920
cagcagatat gttag                                                     1935
SEQ ID NO: 66          moltype = DNA   length = 1935
FEATURE                Location/Qualifiers
source                 1..1935
                       mol_type = genomic DNA
                       organism = Nicotiana tabacum
SEQUENCE: 66
atggcaactg gtatcgcttc aggaagcgga cagttacatt tgaggaagcc tgtctactgg     60
aggagtagct atggaaaagc tcactgtcat tccaatgcga tcctgaatgg catgcaaaac    120
cagatcccttt ggtcttattg ggtttccaaa ttcttgcgag ttcatagaag taactactca    180
caatgtcaag tgaaaacaaa ctggaagtct cacaccggaa caatcaattc ttgccagaga    240
gatggctcaa ctaggtattt tgattttgct gtgattgtta gtggaattgc tggccttaga    300
tatgctctag aagttgcaaa gcatggaact gtagctgtga taaccaaggc tgagcctcat    360
gagagtaaca ctaactatgc tcaaggtggt gtaagtgctg tgttctgccc tatggattca    420
gtggagagcc acatgcaaga cacaattgtg gcaggtgctt acctctgtga tgaggagact    480
gttagagttg tgtgtaccga aggacctgag agaattagag aactgattgc tatgggtgct    540
tcattcgatc atggggagga cgggaatctg catctagcca gggaagggggg ccactcccat    600
cgtcgaattg tccatgctgc tgatatgact ggcagagaga tagaaaggg cctattagag     660
gcagttttta agcatcctaa tatacatgtg tttcaacacc attttgctat agatttttg     720
accactcagg atggttctga cataatatgt catggcgttg atgctataaa cacggaaacg    780
caggaagtta taagattcat ttcaaaagtg actttgctgg catcaggtgg agctgggcat    840
atctatccaa gtactactaa tccaccggtt gcaactggag atggaatggc tatggctcat    900
cgagctcaag ctgtaatttc caacatggag tttgtgcaat tccatccaac tgccttggct    960
gatgaaggcc ttcccaacag accaagtgcc agagagaatg ctttttttgat aactgaagct   1020
gtcagaggtg atggaggcat cctttacaac ttagatatgg agagatttat gccaatgtat   1080
gacaaaagag cagagcttgc cccgagagat gtggtagcaa gaagtataga tgaccagctc   1140
aaaaagcgtg gcgaaaagta tgttcttctt gatatcagtc acaagcccag agagaaggtt   1200
ctgtctcatt ttcctaatat agctgctgag tgtctccgcc atgggttaga cataacacag   1260
cagccgattc cggtggttcc tgctgctcac tacatgtgtg gtggagttcg tgctggactt   1320
gagggtgaga ctaatgtgca aggccttat gtggcaggtg aagttgcatg tactggttta   1380
catggtgcta accgacttgc tagcaactcg ttgcttgaag cactagtgtt tgcacgaaga   1440
gctgtacaac cttcaattga tcacgtgaat gtgtctagaa ttgatcactg tgcttcaagt   1500
tggtggccgc gacctgtagc cccagtggta ataggagata cagtacttaa caaagtcatt   1560
cgtcggacaa gggaagtgag gaaagaacta cagtcaatca tgtgggaata tgttggaatt   1620
gttaggtcta cctcaagact aaccgcagct gagaagagaa tcaatgagtt ggagttggaa   1680
tgggaaacat acctatttca gcatggctgg gaaccaacaa tggttggact agaggcttgt   1740
gagatgagga atctcttctg ttgtgccaac ctggtagtta gcagtgctct ttctcgacac   1800
gagagtcgcg ggcttcatta caccattgat tttcctcatg ttgtgaaag caagaggttg   1860
ccaacaatca ttttttcctc acagcgaaat agctcgtgga gctcacggca attacacagg    1920
cagcagatat gttag                                                     1935
SEQ ID NO: 67          moltype = DNA   length = 1938
FEATURE                Location/Qualifiers
source                 1..1938
                       mol_type = genomic DNA
                       organism = Nicotiana tabacum
SEQUENCE: 67
atggcaactg gtatcgcttc agtaagcgga cagttacatt tgaggaagcc tgtctactgg     60
aggagtagct atggaaaagc tcagtgtcat tccaatgtga tcctgaatgg catgcaaaac    120
cagatcccttt ggtcttattg ggtttccaaa ttcttgcgag ttcatagaag taactattca    180
caatgtcaag tgaaaacaaa ctggaagtct cacagcggaa caatcaattc ttgccagaga    240
gatggctcaa ctaggtattt cgatttcgcg gtgattggta gtggaattgc tggccttcga    300
```

```
tatgctcttg aagttgccaa acatggaact gtagctgtga taaccaaagc tgagccacat  360
gagagtaaca ctaactatgc tcaaggtggt gtaagtgctg tgctctgccc tatggattca  420
gtggagagcc acatgcaaga tacaattgtt gcaggtgctt acctctgtga tgaggagact  480
gttagagttg tgtgtaccga aggacctgag agaattaaag aactgattgc tatgggtgct  540
tcattcgatc atggggagga tggaaatctg catctagcca gggaaggggg ccactcccat  600
cgtcgaattg tccatgctgc tgatatgact ggcagagaga tagaaagggc cctattagag  660
gcagttttta agcatcctaa tatacatgtg tttcaacacc attttgctat agatttgttg  720
accactcagg atggttctga catagtatgt catggcgttg atactataaa cacggaaaca  780
caggaggtta taagattcat ttcaaaagtg actttgctgg catcaggtgg agctgggcat  840
acctatccta gtactactaa tccgccggtt gcaactggag atggaatggc tatggctcat  900
cgagctcaag ctgtaatttc taacatggag tttgtgcaat tccacccaac cgctttggct  960
gatgaaggcc ttcccatcag accaacaaga accagagaga acgcttttt gataactgaa 1020
gctgtcagag gtgatggagg catcctttac aactgagata tggagagatt tatgccaatg 1080
tatgatgaaa gagcagagct tgccccgaga gatgtggtag caagaagtat agatgaccag 1140
ctcaaaaagc gtggtgaaaa gtatgttctt cttgatatca gttacaagcc ccgagagaag 1200
gttctttctc attttcctaa tatagctgct gagtgtctcc gccatgggtt agacataaca 1260
cagcagccga ttccagtggt tcctgctgct cactacatgt gtggtggagt ccgtgctgga 1320
ctcgagggtg agactaacgt gcatggtctt tatgtggcag gtgaagttgc atgtactggt 1380
ttacatggtg cgaaccgact tgctagcaac tcgttgcttg aagcactagt gtttgcacga 1440
agagctgtac agccttcaat tgatcacatg aatgtgtcta gaattgatca cggtgcttca 1500
agttggtggt cgcggcctgt agctcccatg ttactaggag atacagtaca tggcaaagtc 1560
attcaccgga caagggaagt aaggaaagaa ctgcagtcaa tcatgtggga atatgttgga 1620
attgttaggt ctacctcaag actaaccgca gctgagaaga gaatcagaga gttggagttg 1680
gaatgggaaa catacctatt tcagcatggc tgggaaccaa caatggttgg agtagaggct 1740
tgtgagatga ggaatctctt ctgttgtgcc aacctggtag ttaacagtgc tctttctcga 1800
cacgagagtc gcggtcttca ttacaccatt gatttttcctc atgttgagga aagcaaaagg 1860
ttgccaacga tcattttcc gtcacagcga aatagctcat ggagctcgcg gcaattacac 1920
aggcagcaga tatgttag                                               1938
```

SEQ ID NO: 68       moltype = DNA  length = 23225
FEATURE              Location/Qualifiers
source               1..23225
                      mol_type = genomic DNA
                      organism = Nicotiana sylvestris
SEQUENCE: 68

```
gcttccttgg ccaacaatca gttaatttgt aacttcgaat tcgagttcaa ttctacttcg   60
gagcgccatt tttgccccgt taaggtaact gtattgttca aaacttttt tgttttgtcg  120
atctatttt ttttgttttg ttttggaata taactatag ttgtaatttt ttgggtgggg  180
gatgtggttg taatttagtc taggggttctg ttaggttggg gatgctagaa tcttgagaag  240
ctttataaat atacgaacat gcagttgtat gataaactga tagccggtag atcctgttgt  300
tgcgaacatg ctatgctagc tcaattctgc tctctgttcc cttttctac tgttttcttt  360
ccctggtaaa gcaacacagg ctgacacaat cctagcccaa atgagagtaa caaagtttcc  420
agtctttaga aggtgaaatc tataagcaaa tagatgtgaa tgtaagtgcc ttctggggca  480
tacgattaac aaatagacgt gaatttaaat cactgcagga attgagagaa gaaatataga  540
gtgtgttcgg tataactgaa aatgttttca cttattctcc agtatttggc tggtgagggc  600
aaaatattc cggagaatat ttacaaatgt ttgtttggtg agtggaaatt gtttcctaat  660
gttgttacaa aataattttc tttttgattt catttaggcc ccttaaagtt cttgaaagat  720
taactgcaga aaaagtatt caacatgaca tgtcattctt gtaagaacaa gtcattaaga  780
aaaagaaaaa taatatatta aaattagaaa gtttctaaat atatgaaaat gtcaatcttt  840
tgtaaataat tcaagaaaat gaataatgac agtaatttaa aagtatcaca gatttacata  900
aagaaaggaa aaggaaaaga gagaaggta catgaaattt taaatgcttt ggctagattc  960
aaattccata ctcctattaa agaaaatgcc tgacaggtaa gaacatatag gtactgttgt 1020
gtcaacatgc aatagcattt ggtcacttg gagagagtat agagaaaag agaaaatggc 1080
agagggaagt gggagggagg caagagccga ttgtctagcg ccaaaaagtt tgatatgttc 1140
tggatattgg aaaattgactt tccttgggtt cttaggtaag ttagtttcat caaaattaaa 1200
ggaaaatgtt ttctttagga aatgttttcc ccaacaattt aggccaacca aacatggtaa 1260
aattggaaaa gattataag aaaatgtttt ctttcatacc aaatacaccc ataagtagga 1320
gggattgtga taaattttgc aagttgttta tgtatttca gagatctatt tacctgtcat 1380
acatgttcta caaaacacga gtccatgtat atatcattgc acttctcctt tacaacttat 1440
ttaatttcta tttaaacagc tttagcgcgt aagagctgtt catttccttg aacaccattg 1500
ccaaagaacg gttaatgag ggaaatgaa aatttagcta tgttggcaag tcctgagtct 1560
tagagcaaat gatcttcatt gggtcttatt gtttccttgc aatacttgtt cagtcttgta 1620
agttctgatt ttcgctaaaa caactctttt tagtcgtcac ttgttactta caatttcctt 1680
tctcctaata gaaacgtgtc cggaaagctg actttttgcc tctatgtgt ttctggttt 1740
tggagccttc agaatgatag tactagctgt tcaggtgtct attgagggtc ttcatcaaag 1800
caacagtaag gaaatagtta gaaaaactga aaaggacttc tccttaacgt gtttcagtct 1860
cttgatttta aggaaatgc attttgtaga tacattggca ttcattgaaa atggccttga 1920
ctcaataccct atgtcatgtg acatcaggaa gggaaagcaa tgattttctct ttctgtttca 1980
gtaataagtg atgaagtctt gtggcaactt ccatttgtaa attcattttg tacaagtgga 2040
ttatagaaaa ttagttgata agttcatacc tttctttct ctactttttc tcttgcaata 2100
tgagatatca caggttagag acatgatgca cattcatttg tggttcactt gaatgagaaa 2160
aaagtatatg tttcttcttt ttatgtttcg tttccttttg gttttcagta tctggtatcg 2220
aagttgtgta ataaacagtt tgttccacgc atgtgctgct gcagcattaa catggactag 2280
ccatcttgtc gtaggagttc aatttgtgga attccggtt aagcccatca actgtggaat 2340
ctctaaaatat tttcattgaa ttcaccatac gttagatgat atgttttctc atggtccttt 2400
caagcacttc tccttctgtt taaatgtctc cacatgcttt tctgccccct caatatcaga 2460
atttgtctaa aagttccttt ttctttaata aatctactgc tccaaatgaa tgatagaaga 2520
gttgtaaaga gttctgactt caagaccaag cacagttttg gttgggcttt caaattagct 2580
tataggaagt tgttcctaag atcgtcctga aacaaaatct tttcttttttg tagcttctac 2640
```

```
tgtattcatt catgctttaa tgcaatttat aacaaggttt ccectaaata tccagagtct  2700
ttaattttgc tttcgagtcc cagctgcgca aaacgtatta ccgaagaata gttttctggg  2760
agatgttaca agagtttggt tagaagggtc tttcccttct aaagtgtttg gttcaagtta  2820
tctaaatgtc aagagccaat attttgttat taagctcaat tccttgccct gtttgggtgt  2880
ttttagaggt aatcaagatg attttaaat gtttagtttc actaacattc taacctcaga  2940
attgggtgtg ccaatctgat atcaattcct ttgacttgga ttgtcagtca ggaagatcat  3000
atggcaactg gtatcgcttc aggaagcgga cagttacatt tgaggaagcc tgtctactgg  3060
aggagtagct atggaaaagc tcactgtcat tccaatgcga tcctgaatgg catgcaaaac  3120
cagatccctt ggtccgtatt aggatgatgt ttcttcgcct atctctcctc tctatctttc  3180
cctgctttat tatcttcatt ctattgcccc ttctcctctc ttttgggga ataattgtca  3240
aaatgtttta ttttggagct ttcaagatgt tattacattc caatttgtac ggacataggc  3300
attcacgtgt tggctgttgg actgtttatt cctcccatga gaacttactg gaaagaatct  3360
ttgtatacgt gtttaggcat aaaccagtaa tatcttttt catgagatac cagaatccta  3420
aaagttttt ttttgagtca tttcctgatt cttaggaaa aaaagaaagg ttatcatttt  3480
cattttctgg tggtgatatg ctacttaaat tttccaggtc ttattgggtt tccaaattct  3540
tgcgagttca tagaagtaac tactcacaat gtcaagtgaa aacaaactgg aagtctcaca  3600
ccggaacaat caattcttgc cagagagatg gctcaactag gtattttgat tttgctgtga  3660
ttggtagtgg aattgctggc cttagatatg tctagaagt tgcaaagcat ggaactgtag  3720
ctgtgataac caaggctgag cctcatgaga gtaacactaa ctatgctcaa ggtggtgtaa  3780
gtgctgtgtt ctgccctatg gattcagtgg agagccacat gcaagacaca attgtggcag  3840
gtgcttacct ctgtgatgag gagactgtta gagtaagttc acagaatatt attgtctctt  3900
cagttccgtg aagcagtttg ccctttttca gtttttttctc tttggaagtc gtttcctttg  3960
cttttccaaa ttttttccagg actgcttggt tggatgaata ggaaagttct ccatctttca  4020
ggttgaaacg aaaggaactt tctgtttaga cggcttttgc cacaggatct agaactgcca  4080
aaaaatggaa aagggtaaga gcaatcgggc agttaggctt gttttcaatt agaagctgaa  4140
gagccaagca ataatactaa agaaaggctc tatgcctatt cettcettct gatgtaagtg  4200
cttacaagtt ggaaccgaag aaagagttgg agagttgaga aaccaatggt tggtaatatg  4260
gacgacttcc tctggtttat gtagtgctcc tattcttcat ggttcagatt gttgaatttg  4320
tctttgaaca tcgtgagaag gcacgggaga aaatatgatt gatattattc tcatatgtta  4380
aacatgatac aatgagccct gtatatacat aacatgctct actcctaata catatgggat  4440
tagggttaca taactattct aacactcccc tcaagctggt gcatataaat catatgtacc  4500
gagcttgtta catatgtagt taatacgagg accagtgaga gacttggtga aaatatctgc  4560
aagctgatca ttcgacttca caaactttgt agcaatatct cccgagagta tctttctct  4620
gacaaaatga cagtcaatct caatgtgttt agttctctca tgaaacactg gatttgatgc  4680
aatatgaaga gcagcttgat tatcacacac aagtcccatc tgactaatct caccaaattt  4740
caactcttg agcaactgtt tgatccaaat tagctcacat gtcaccatag ccattgctcg  4800
atattctgct tttgcactag accgagcaac cacattctgt ttcttgctct tccaagatac  4860
caaatttcct cctactaaga cacaaatatcc agaaatagaa cgtctatcag aaggtgatcc  4920
tgcccaatca gcatctgagt atccaacgat ctgctcatgg cctcgatcct caaacaataa  4980
acctttgcct gaagctgatt ttatataccg aagaatacga acaactgcat cccaatgact  5040
atcacacgga gaatccataa actgactcac aacactcaca ggaaaggaaa tgtcaggtct  5100
tgtcactgta aggtaattta atttaccaac caaccgccta tatattgtag gattgctaag  5160
aggctccccc tgtcctggca gaagtttaga attcggatcc atcggagtgt caacaggtct  5220
acaacctgtc attcctgtct cctcaagaat atctaaggca tacttccgtt gtgagatcac  5280
aatatctgag ctagactgag cgatctcaat acctagaaaa tactttagtt tgcccagttc  5340
cttagtttga aagcgttgaa agagatgttg cttcaattta gtaataccat cctggtcatt  5400
gccggtaata acaatattgt caacatagac caccggataa atatagagac tcgaagcaaa  5460
atgccgatag aatacagagt gatcagcttc actccgagtc atgccaaatt cctggataac  5520
tatgctgaac ttaccaaatc aggctcgagg agattgcttt agaccataaa gtaatcggcg  5580
caagtgacat actaggccac gagactcccc ctgagcaaca aacctaggtg gttgctccat  5640
ataaacttca tcctcaaggt caccgtgtaa aaaaacattc ttaatgtcca gctgatagag  5700
tggccaatgg cgaacaacaa ccatggatag aaaaaggcgg actgatgcta tcttagccac  5760
gggagagaag gtatcactgt aatcaagccc aaatatctga gtatatccct tgcaacaag  5820
acgagcctta agacgatcaa ccttaccatc cggatcaacc ttgactgcat acacccaacg  5880
acaaccaaca ctagattac ctgaaggaag agggacaagc tcccaagtac cactcgtatg  5940
taaatcagac atctcgtcaa tcctgtcgcc atcctggatg agacaatgct tcacctgtag  6000
acttagggat ggaaacagag gacaaagaag atagaaaagc ataataggt gaagacaaac  6060
gatgataact taaaccgaca taatgggat taggattaag ggtggtccgt atacctttcc  6120
gaagtgcaat cgatgtacta ggaagagaca agtccgcagt aggaccaggg tcaggtgcag  6180
gacgtgaatc agctgggcct gatgctgggt gcagatgacg atggtatgtc aagagtggtg  6240
ttcctgtggc agggagtgta agaggagcca cactagactc cccaacggtt ggaatgggta  6300
agacttctgt ggcggaaggt gaagaaggag atatagtaga atccttaaag gtcggtatag  6360
gtaagacctc agatatatca aggtggtcag aagaggtaaa gaaaggttta gactcaaaaa  6420
atgtgacgtc ggaggacata aagtacctac gaagatcgaa tgaataacaa cgatatccct  6480
tctgaacacg agaataacca aggaagacac acttgagagc acgaggagct aacttatctt  6540
tcccaggggc taagttatga acgaaacaag tgctcccaaa aacacgaggg ggaacagagt  6600
ataagggtga cgggggaaac aatactgcat acaaaatctg attctggatg ggagatgaag  6660
gcatccaatt aaccaaataa caagctgtga gaactgcatc gccccaaaaa cgcaacggaa  6720
catgagattc aataagaagt gtgtgagcag tctcaatgat gtgcctattc tttctatctg  6780
caaccctatt ttgctgaggg gtataaggac aagaggtctg atgaataatt tcttgagaag  6840
tcataaactg gtaaaattga gaggataaat actctaaggc attatcactg cgaaaagtgc  6900
gaataaaac acgaaattga tttttaattt cagcacaaaa attctggaat atagaaaaca  6960
actcagaacg atctttcatt aagaaaatcc aagtacatct tgaatgatca tcaataaaac  7020
taacaaaata acgaaatccc aaggttgaat tgactctact aggacccat atatcagaat  7080
gaactaaaga aaaatagac tctgcatgac tctcaatact acggggaaag gaggctcagg  7140
tatgtttctc gagctgacat gactctcatt ctaatgtaga taaactagac aaactaggca  7200
ccatcttctg aagcttggat aaacttggat gtcctaaatg tctgcgaatt aggtctggag  7260
gatctgtaac tagacatgcc ttggaggaat tgagtgagtt aagtagtaa aggccttctg  7320
attcaagtct tgttccaatc gtctgtcccg tactgcggtc ctgcataata aaagaatcat  7380
```

```
caataaaata tatacccaa tggagggcac gagtcaaatg actaacagat gtaagattaa    7440
aaggacaacc agggacataa agaacggaat ctagagtgac agagggtagg ggattcgctt    7500
gtccaacacc ttttacttta gtttgagacc cattggctaa agtaacagtg ggaagagact    7560
gtgaatacgc aatatttgac aaaagtgatt tattaccaaa aatatgatca gaagcggctg    7620
agtccacaat ccattgtcca agagtactag actgggaaca acaagcaaaa gaattaccag    7680
caacagaagt atcagtctga gcaatagagg ctacttgtgg agatgtttgc ttatttgctc    7740
gatattgaag gaactcatta tactcccctt cagataaaga aaatccctgg ttacctgtag    7800
tctcggtctg agcaacataa gcattttgg gtgggcgacc atgtaaagaa tagcacacgt     7860
tactagtgtg tccaagttta tgacaataag agcacttgag tctagatttc caaaacgacc    7920
tcctcctcgt ctattctcca tagtttgaga tgcccgattg tccactgact gggatacgaa    7980
gacagatgag tcaagtgtct gtgatgagct cactgggtga cttggtgctg cagcaaggcg    8040
aagtaatcga gagaataatt catcaactgt ggggacagtc ggtctagcca aaatctggtc    8100
acatactgaa tcaaggtcat tagggagtcc agcgagtgta agaactacaa tatcctctgt    8160
cgttgctctt gttgctttc aatactagca gaaactgcca tcaacgtctc aaattcttcc     8220
atgactgcct gtacttgttc caagtaagta gatatatcca attcctgttt cttcaagctt    8280
gtcattcgca atattacatc atagagacga gatatgtcat tagtgtataa attacgagcc    8340
ttttcccaaa ctaaataaca tgtatggaat ggacggaaca agagcatcaa tttggaatca    8400
atagatcgcc acaagatact acataactga gcattgacct tctcccaaag tgttttggcc    8460
ttttcatcac cttcgctagc cttttttgtt aaatgatctt gaactcgttg acctttacac     8520
cacaactcga aagacgaagc ccaagctaag tagtttgaac ctcccattaa aggttctgag    8580
gtaatcgtaa caccggaatt gccagaaccc gggttttag acccgaaagc atcgactccc      8640
aaagacatcg ttggattatc accaaataac agaaagaatc actgacaac ttgctgaaac       8700
aggtgaagga aacactgttt ttgccggaaa attactgtag ctgccggaaa aagtcggtgt    8760
agtcgccgga aaaactcaaa gtggtcgaa tcaaacgaaa aaggtatgga gactcggaat      8820
tactaggcga tccgactgtc caactggaag ttttcaaaa aaatggttgg aacagtgctc      8880
acgcgccagt gcgtggggcg cttgggtcag atctcgccag aaagttttg gcgcgtgagg      8940
gcgcgtgtac gtgagttttc cgtgggggtt tactagggtt tggtcgccgg agcctgagga    9000
gtcttgtggt gttattggtt ttttgcacac accaacaaaa attgatgtga ttacgagcag    9060
ccttctaagt cgccgtaaaa ttgcacggcg acgaggtctt tcttcccgga agtcgctgga    9120
atgatgcaca acgataggtt tctcactaaa gctctgatac catgtgagaa ggcacgggag    9180
aaaatatgat tgatattaaa catgatacaa tgagccctat atatacataa catgtcctac    9240
tcctaataca tatgggatta gggttacata actattctaa caaacattat gaaaagagag    9300
tgaaggtgac atgcaggaag gaagagataa ggataagaca ggaaattcac atgtgttgtc    9360
ttttggttttt attttgggat ttcatttagt ttgtgccaca gtaccatgtt ttttttcttt    9420
aatgagaaca cacttctgac ttcctaaat cagcaccaat tttctgaggg taactgctga      9480
taaggataga cactccaagg ttatccagga ttcctagctt aagttgtatc atataagttt    9540
ctctcctatc ccctcaagag tcctatgtac agaaaactct atcccttctc tctcgagctt    9600
tagctccgga gtccatttac ttttgttaat gctaacaact cttgcggagt tgtgaagtgc    9660
cttcttctgc cgagagtagt aaggcccaat ggacttcgca tctagtaggc ccattatcaa    9720
catcaaatga gggagaaggg atagagttct ctgtatataa ctcttgtggg gataagagag    9780
aatcttatat gatacaactt aagctaggtg ttagcgaaa cgtaaagaa agaacacaag       9840
atttaacgtg gttcggatca aaataatcct acgtccacca gagaacaatt gccctttaa     9900
tattaacaaa ggaaggggag attcccaat tacacttaag agaatttctc tcttaactct      9960
ctactcacta caatgtattg tattattttg ggatgatttc tacaagtgaa ggagtgcatc   10020
tatttatata ggtaaagatg acatcaagag gaggtagttt gatgtcatgg gtgacatcaa   10080
aggaggaagc ttcctcctag catccacacc aactctttcc accaactctt ccaattggca   10140
tgccattgtt gactaaacat aaaccaacat tttcagcatg ccattgttaa ctaaacataa   10200
accaacattt tcactaggga tcctggattg ccttggagtg tctatcctta tcaaccgctt   10260
agtttgctgt atactatttt catttgtctc tgtaaatata tactggtttc aaggaagttt   10320
tgtgttgtgc ttggtagatg ggatatcaca actaatatct tcttatcagt tgataaaatc   10380
ctggtccatg taattctgct ttttatgcaa tctatgttct aaatgaaatt tatgagatgg   10440
ctgatttatt actccaaaat tgtgtttagt ctactctttt aaaatcttcg ttttttataag   10500
tatatctcct ttctccaggt tgtgtgtacc gaaggacctg agagaattag agaactgatt   10560
gctatgggtg cttcattcga tcatggggag gacgggaatc tgcatctagc cagggaaggg    10620
ggccactccc atcgtcgaat tgtccatgct gctgatatga ctggcagaga gatagaaagg   10680
gccctattag aggcagtttt taagcatcct aatatacatg tgtttcaaca ccattttgct   10740
atagattttt tgaccactca ggtaattctt ttctttgctc ttcttgttta ttattgagaa   10800
aatacttctg ctctagcatc aatttggtcc aaaatgaagg gttgttgcta taatctaatt   10860
agtcttggca ttattctttt gcttatgtg tttgtgcagt tgaactgttt ttccatgtaa     10920
acatttgcta atgttaattt gtatgcaaa tgcaggatcg ttctgacata atatgtcatg    10980
gcgttgatgc tataaacacg gaaacgcagg aagtaagtac agttgctttc actcatgttg   11040
acctccatgt attgaacatt tcctcacaat gacataaatt gatttcttag gcttctgcgc   11100
tcttactgtg agtttgtagg ttataagatt catttcaaaa gtgactttgc tggcatcagg   11160
tggagctggg catatctatc caagtactac taatccaccg gtgatgagttt caatatcttt   11220
tcctccataa tattttcatt tatgagggat gtcactcctt ataatcaata agataatcag   11280
agtcctaaac agtgatatgg ggggagaagg tgggaaggga atggtggcta atactgtaat   11340
agttaatttc atgactagca tacatttgca tcttattgtt ggcgataagc ttcgtcacaa    11400
agtatctttc gtaactcata aggaccttaa caattgacat tggtgcaaac aacattccct   11460
agagtatgaa acatggcctg attttaatta tttaaacct acagcacttg catgttaagc    11520
taatgtgcaa ttagaaataa gggctggctg ccctaagcca caaaagagg aaaaacccaa    11580
atatacccct gtacttcgtg aaaaggtcta agatttattc tccctttgaa gtttggctcg   11640
ctggtgccct cgccgctaaa cttttggact atatttaccc ctatttgcta acggaccttg   11700
gtttgagact taacaacaac aacaatatac ccggtgtaat cccacaagtg gagtctgagg   11760
aagcgtgtca agataataga aggaaaaaga tatttaggag aggaacaata aattgcaca    11820
gacaagacaa gatttaggtg gttcgacaat ttttgcctac tccacggcca cacaaagaat   11880
agctctttat taattgaaga gagaaagaag aagtttggg atgatctaca aatgaaaatg    11940
tagcccta tttataagca tttgaatgcc ctgccgaggt aagcgcttac atcataagaa      12000
tgtcgatgta agcgcttaca tcataagaat gctgaggtaa gcgcttacat cacaagaatg   12060
tcgatgtaag cgcttacatc atattttcat ctcttttcga ttttttcttc tttgtttg    12120
```

-continued

```
tctactttca catacaacaa caggtttggt cctatcaatc tccctctcaa acctatgtta  12180
catcaagaaa gaaaataaag aaagatttgc tattctctgg tggcgccttc actctatcag  12240
tcttgaaggc taactgaggc agtgcacagc ctcagtttgt caacaccgac aactttggtc  12300
aacatgtctg acgggttctt taatcctggt atcttttgta gggaaagagt tccttcattt  12360
atcaactctc ggatatgatg ataccctcaac tggatatgct tcgttcttgc atgaaacact  12420
ggattcttgt caagatgaat tgcactctgg ctatcgctga aaagctcata attgtcctgt  12480
tctttaccta gctctttaag aaaattcttg agccaaatca tctctttttcc agcttctgag  12540
attgccatgt actctgcttc agtggtagat agagcaacac ttttctgaag tctggacatc  12600
caactaacag cagtaccacc aaaggtgaac atgtagccgg tggtacttt tcgactatcc  12660
agatcgccac ctaaatttgc atcagtaaaa ccttgtaaga taatattgct cttttaaaa  12720
caaagtgcca tacctgaagt gcctttgaga tatcgcaata tccatttac accttcccaa  12780
tgctcctttc ctggatctga catgtatcta ctgacaactc caactgcatg gctatgtca  12840
ggtctagtgc aaaccatatc atacatcaaa cttcctactg ctgaagcata cagaactttg  12900
gacatgtact tcctttcttc atctgtctta ggtgattggt cctttgacag atttagatga  12960
cttccaagtg gagtgcttct ggtctttgca tcatgaagac tgaacctgct tagtaccttc  13020
tgtatgtact tttcttgaga caactttaag gttccttccg acctgtttct gctaatcctc  13080
atcccaagca tttgcttagc tggtcctaag tctttcatat caaactcctc cgccagttgt  13140
tgcttaacca agttgatctc atttatgcta gatcctgcaa ttagcatatc atcaacgtac  13200
aacaataaaa tgatatagga ttcatcaaga tttttgatat aacagcaatg gtccatctca  13260
catcgtgtga aaccattttt atgcatgaat ccatcaaatt tcttgtacca ttgtcgggga  13320
gcttgtttca aaccatacaa actcttcttc aacttacaca caaggttttc tttaccagaa  13380
acttgaaaac cttcaggttg cttcatgtag atgtcttctt caaggtccgc atgcaagaaa  13440
gcagttttaa catctagctg ctccaaatgc aaattttctg cagctacgat acttagcacc  13500
aacctgatag tagttaattt gactacagga gagaagatct cggtgtagtc aattccttcc  13560
ttctgctgaa agtcttttac tactaatcgt gctttgtatc tcttcttacc atcatgctct  13620
tccttgactc tgtacaccca ctcgttctgc aatgcctttct ttccttttgg taactccgta  13680
agtatccatg ttttattctt ttgaagagaa ttcatctctt ctttcatggc tagcttccac  13740
ttatcagagt ctatccactg cattgcttca acaaaatgct ctggttctcc agcatcagta  13800
agaagtaaat agtgaagaga gagttaattt atttggagca ttcgtgactc ttttagatct  13860
cctcaatgta ggttcatgag taacagaatc cgaatttgat tcaggtcctg attccagatt  13920
tggttctgga tttgattctg tctctggttc cacttcaggt tcggcttcta gttcttcttc  13980
aaattcggct tctagttctt catcttcaat ttcagaatca gttgtaatcc ctctagctac  14040
ttcatttcct gagatttctt ctaactcaac tgtttcagac attgtctgtt tgctggtgtt  14100
ggttggttct acttcaagct tgtccttgta catcacattt tcattaaatg tgacattcct  14160
gtgtcttagg atcttctctat tcggatcatc ccaaaaccga taaccaaaat tatcatcacc  14220
atagccaata aagaaacatt tctttgcttt aggatcaagc ttatctctat cattagagtt  14280
tacatgcaca taagcaacac aaccaaaaat tttcagatgt gagagagtta cctcctttcc  14340
tgtccatacc tcctcaggaa tttcaaaatt cagcggtaca gagggtcccc tgtttatgag  14400
gtaagctgcc gtgttaacag cctcagccca aaaatacttc ggcaatccag aatgtattct  14460
catacttctg gctcgttcat tcagggttct gttcatcctc tcagcaacac cattttgttc  14520
cggtgttcca ggaactgtct tgatcattct gatcccattc tccgagcaaa atgctttgaa  14580
ctcttggcta tcatactctc ctccattgtc agacttcaga catttttaact ttagacttgt  14640
ctgattttca atctcagctt tccatctttt aaaggtaaca aatacatcag atttattttt  14700
cagaaaataa actcatacct ttcttgtgga atcatcaatg aaggtgacat aatagcgtga  14760
gcctcctaga gaggttacag gagctggtcc ccacacatct gtatgcacta gttccagctt  14820
ctctttcttt ggcgtcctcc ccacctttga gaaactaact ctcttttgtt tcccgtaaat  14880
gcaatcttcg cacaaaccta attcaacatg ttttaggttt gacaacttct ttttggatgc  14940
caaaagcttc attcccttct cactcatatg cccgagcctc cggtgccaca atgttgtatc  15000
acgaccatga tcaactgttg ctatagtatc tcttttctatt acagttgcat gcagtgttcc  15060
cctttgaag cctcgtgcca caaccaaatt cccttttggtt atcttccacg atccgttgtc  15120
gaatgttgtt gtatatcctt catcgtcaat ctgacccata gatatcagat ttttcttgag  15180
gccaggaaca tgtcgtacat tttgcaattt ccatagcgtg ccttgtgaag tcttatata  15240
aacttcacct tttccggcaa tgtcgagagg ttcgccgtct gctagataaa ctttcccaaa  15300
ttttccagca atataattat gcaataattc tttgcatgat gtagagtgaa aggacgcacc  15360
tgagtccaga atccaagatt caactggact gtctgcacaa caaattagtg catcaccgac  15420
ttgttcagca attacatttg ctgaattttc ttccttcttc ttctttggtt ctctacattg  15480
actactgtag tgacccttt tatcgcaatt ccaacaagta atgccttgc gattttttgga  15540
ttgtcctctt ctccttgact ttgatctgcc acgaccataa atctgtcctc tttggttgat  15600
tctccccctg ctttcggtac taaaagcaga tcctgggaa tcacttgatt cttttcggcg  15660
aatatcttcg cttagaacca agtctctaat atcattcaat ttgagtttgg tacttcctga  15720
tgaactgcta actgcagtta ctgttgcaga ccaactctcc ggtagagatg atagtagaat  15780
caacgccctg atttcgtcat caattgttat attaacagaa ctcaactgag ttaatattgt  15840
attaaactca ttgatatgtt ccgtgactga tccaccttct gtcattttta agtggaacaa  15900
tcgacgcatc aaatacactt tatttgaagc agatggcttc tcatacatat ttgataacgc  15960
cttcatcagg cctgcagtgg tcttctcgtt aatgatgtta aacgccacat ttcgtgttag  16020
cgtcaaacga atcacaccaa gagcttacg atctaataga tcccaatccg ctttggacat  16080
agtctccggt ttcacctcgg tcagaggtaa gtgtaatttt ttctggtaca aataatcctc  16140
tatttgcatt ttccagaatc caaaatcttt gccattgaac ttgtcaatct taaccttccc  16200
ttcttccgat gccatttttc acaaaaataa tttatgtgaa tagtgcttgt gaatagtaac  16260
gatgatcaat agtgtcgcac tattcttgtg aatagtacct gcaccaatac tgtacttttc  16320
taccaggatt acactgtctg tgctctgata ccaattgttg aggaagcgtg tcaagataat  16380
agaaggaaaa agatatttag gagagaaaca ataaattgca caagacaaca caagatttac  16440
gtggttcggc aattttgcc tactccacgg ccacacaaag aatagctctt tattaattga  16500
aaagaagaaa aagaagtttt gggatgatct acaaatgaaa atgtagaacc ctattataa  16560
gcatttgaat gccctgctga ggtaagcgct tacatcataa gaatgctgat gtaagcgctt  16620
acatcataag aatgctgatg taagcgctta catcataaga atgctgaggt aagcgcttac  16680
atcataagaa tgctgacgct tacatcatat tttcatctct ttttgatttt tcttttcttt  16740
gttttgtcta ctttcacata caacaacaag tgtaatacc gggtatattg ttgttgttgt  16800
tgttactcat actgctgcta ctcatctacg tgatcgagaa gtcacaacaa caaattctgg  16860
```

```
gcagaaccaa attggtacaa ccatcccaga tatttcagag gaggaaagaa gactcttgga   16920
tgcaatggtg agttctaatc ccttaaatcc tgtaaatcct acttgcttct agcactggaa   16980
tgttgagtat gagcaggaac aaattgcaaa aatagaaca acatcaaagc aaggcaatgg   17040
tgacaaatac acttggtcaa tctgcattga agacaattgt tatcgaccaa aatgttccac   17100
aacctgtgca cctggggaga gacttgtatg aagacggaga ggaagaagca atgttacatc   17160
agtgtagagc agaggcagca agaaaagggg atctatcacc aatgcatagc ggcaaaggta   17220
agagactcat acaaggaaat ttagttggga cgacaaagtt agtgattttt taaatgttag   17280
gcgacctcca atgagagttg ccaaacaaaa gaaggccgcc ccaactacat ctacaaagtc   17340
caatcattca aataaagaat catgaatttt gaatacatct tgaagaattg gattgtgatg   17400
aaaaagagtt acaaactgaa gaaattacaa gttcggacaa gaagggacaa tattttttcg   17460
gaacaagtcg gtgaaggttc tattacggcc gatagagggg tggcggctcg ttgatggggt   17520
tgtaaagttg taatggtggt gaccggtgaa ggttctattt tggtgagacc atggaattga   17580
gaggggggaag gtgctagctg agaaagtgtt gaagtagtga agcggtgagg gagtctctgt   17640
ggggagctgt tggtgggttg gtgaggttgt ttggcggttt cagatgcaga ggtgtaacaa   17700
gtcggacaag aattggtcag acagggcagt ttttctggca attttttttt tttaaatttt   17760
ttttgaaggt tctgtggtgc tcaaacttct atgaaatttt cagggatggt taattatggt   17820
tggggtggtt gctgcctaga ggattagata aaggtgaag tggttgttta gttatagagg   17880
gagtactttg ggcgacggtg gagaatggtt tggggtgaga ctttgggcag caattgtttg   17940
cgaattggat ggtgaaggtt gactagatga agtgggtttt gggcaacaac atgttgggga   18000
atggaagcat tactgtgtta caatggagaa ggggaataga tggagatctt tgcgggaaat   18060
gggggaaaat ggcctaaggg cagcgacggg gtgcaggggt taatgggaga gggttaaagg   18120
gggagggagg tttattaatt agccacgtgt gggacatgtc acatgtggca cttctggtg   18180
ctaaactgag tttttgagat taactaaaaa agagatcaaa tgattttaa tcatcagctg   18240
ttagcaataa gggtagatat agtccaaaag tttaagggca ccagtgagcc aaactttaaa   18300
ccaagggtaa atctagacct tttcacaaag tacaaggaca aatatggacc ttccctccta   18360
cccctcccc ccaaaaaaaa aaaaaaaaaa agaaacaata aagttctgag gtattaacag   18420
atgatccttt ccttggaagt gtggattctt atctcataag agataaggt aataaattct   18480
tattctatac accaatattt ttctgtacaa taaaagcaag acacattgtt caaagttgta   18540
taacctgggt taggcatcta ctgtggcgct gttatgctcg ttatcaattg ttttttctctt   18600
acggtcattt ctataagttt ttggagctac taattggtgg tggggcccga ttcttttttt   18660
atatttgacc atttgtgcct ttatcaagga acagaaaagt tttaatttgt tgaatgtggg   18720
catgctggct gtaggttgca actggagatg gaatggctat ggctcatcga gctcaagctg   18780
taatttccaa catggagtaa gtgatcctca gttgcattgc attcttattg tccaatatca   18840
ctgtgtctgc tttagtgagt tgtgctgtaa aatctgctaa tctagatttc atccatttt   18900
tgctttcttg atttctgcat cctgttctgc aattcattct gaatttgcac ttttgactaa   18960
aaatacaagg tatgttcaaa atgttgtgcg gggtgacatt ggatctgacc tgaattttc   19020
aggataaagg gcatcaaatt ttcttcattg aggggattta attgatatag aaaagatttc   19080
tcgactagca gtccgctctc taattgatgg tcctcctttg atcgtctttt ggatggtaga   19140
caagtctttg tttgcgaggt tgatgaacta tccccaacgg ttgcattatt aattacaatt   19200
ctcttcttca tgttgccagg tttgtgcaat tccatccaac tgccttggct gatgaaggcc   19260
ttcccaacag accaagtgcc agagagaatg cttttttgat aactgaagct gtcagaggtg   19320
atggaggcat cctttacaac ttagatatgg agagatttat gccaatgtat gacaaaagag   19380
cagagcttgc cccgagagat gtggtagcaa gaagtataga tgaccagctc aaaaagcgtg   19440
gcgaaaagta tgttcttctt gatatcagtc acaagcccag agagaaggtt ctgtctcatt   19500
ttcctaatat agctgctgag tgtctccgcc atgggttaga cataacacag cagccgattc   19560
cggtggttcc tgctgctcac tacatgtgtg gtggagttcg tgctggactt gagggtgaga   19620
ctaatgtgca aggcctttat gtggcaggtg aagttgcata tactggttta catggtgcta   19680
accgacttgc tagcaactcg ttgcttgaag cactagtgtt tgcacgaaga gctgtacaac   19740
cttcaattga tcacgtgaat gtgtctagaa ttgatcactg tgcttcaagt tggtggccgc   19800
gacctgtagc cccagtggta ataggagata cagtacttaa caaagtcatt cgtcggacaa   19860
gggaagtgag gaaagaacta cagtcaatca tgtgggaata tgttggaatt gttaggtcta   19920
cctcaagact aaccgcagct gagaagagaa tcaatgagtt ggagttgaa tgggaaacat   19980
acctatttca gcatgctgg gaaccaacaa tggttggact agaggcttgt gagatgagga   20040
atctcttctg ttgtgccaac ctggtagtta gcagtgctct ttctcgacac gagagtcgcg   20100
ggcttcatta caccattgat tttcctcatg ttgtggaaag caagaggttg ccaacaatca   20160
ttttccttc acagcgaaat agctcgtgga gctcacggca attacacagg cagcagatat   20220
gttagatgct cttaccatt tgccaatcct tcctgctaaa acttgtcaag cgcagggcat   20280
gattagtttt taggtaaaga agatgcttat gggttattgt cattcttcct gccattactt   20340
ttggggcagg gcaacgtcat tcttttggtga aaaaaatata tatctataca tacaaaccat   20400
ataattttga atgtgttcc ctattttatt cttatatagc atattttatt atctgctaac   20460
ttcaagcctg tctagtactc cacgtccca aagaacaac aggttttaaa gtaaaaagtt   20520
aaaccattta attttctgtc tccatataga catcaatttt tgaatctttt taaaataaaa   20580
ttaagggaga tttgcacata tacacagtcc aacacactgt attgcaccta tgtaactaag   20640
tttttcactt ttcacctgca tagccaacat ttgttttgca acaatgtata tacatcttta   20700
aacattattg tatatttgtt gtaaacaatg tattaacctt gtataaaatg taaatagta   20760
aggtgtttat acatacttac actgttatat aaaattataca gtgttataca aaaattgagt   20820
gtttgattca ccttagaagc agtttagct ggcaaagatc ccccccccc agtctttgca   20880
ctctcatcct tgcttatatt ctgcactaat tttcatagttg ttccctttgat ttcttttgtt   20940
gggatggaga aaggtgtgtg gagggagttg gttcgatgac ttccgtttga gtttcttctt   21000
gtttcttggt atgatcagac ttggttttgg tagatgacct ggtactagac ttgggtttaa   21060
gggtggtttg gctagatttg atcatggtga attttctagg tttaaaaatt ttcttagagc   21120
cttacgggga agaagtaggg atggcaatgg ggaaggccgg gcgggttaag tcttcaccta   21180
ctaaattttt gccttgcctt gcctcgttta gttctttgcc ccatttagat catgccatgc   21240
cctgccccgt ttagccctaa acttaatagt tctttcattt ttatccatct aactagcgca   21300
attgtttcta ataatattta gtaaatggtc tcctacttca tcgattctgt aggagcctaa   21360
attgtctaaa aaaaaaacgc catcttcctt cgtgcagttt ggtatcttat accaatcgag   21420
agagataatg ttttttccgt actttgtaaa cgaactacaa gtcaacatta tgttaacat   21480
ttcgtactct gtaaacgaac tacaagtcaa cattatgtag tacaagtcaa cattatgtat   21540
tcgacgggaa gcgtcacagc ctaggttagg aacacccccg agaaaccta caataggcag   21600
```

```
atcacctctt ttattatagt agatagacaa catttgtgga ctacgataaa tgttttcaac  21660
caatctgaca ttgtaaatgc acatgtaatg ccatgtatca gttcatacat gtggtaattt  21720
aatgaaggat tggaaatata cattttttatt ttacaataga agaatgcttt attagttctt  21780
tgtgcttgcc aatctgaaag aaatcatttg atattctgtg acatcatgaa gtcaacacca  21840
aaaaaagttt aaatggttga tagattcttt ttgtcagttt tcacacaggt aacatctgct  21900
gcaaatagaa agtcctcttc tctgccaatt atcttggcta agacatgctg cctcgacagt  21960
attcccaca aagcagggaa ttttggtgtg ttgttttttgt cctccgtgtt atcttttact  22020
atccagcttt tggagaagat tgtagcaact ttggacaccc tatacagtac ctatatcata  22080
atcagaacta ctggtctata aactccatta cttttttcact ttgttccgca atcacctttg  22140
aggttgttgt atagagcaag attgaggttg tcgtaaatgt atatttatca ccatgactgt  22200
tttcatggta aatgtcctga ttaaggtggc aagaccataa tgcatgtgtt gaatttacca  22260
tctgcacata tgaatggaga agaaaaaatg ttaaaacaaa aaaagaacaa aaaaagacaa  22320
tggtaataaa gacgatgaac taagttcaaa gcggctgcaa aagtgtgaaa ggtgactgtt  22380
ctctatcatt aaagtttatc ttaaactatt gatgtcattc agggttgaca aaacagtcac  22440
caaatataag catttttgtt cggggttgaa ctacagagag taggaattca tccttcaatg  22500
tccctgtttc aatccaacta tgtgtgcaaa attttatctt cctttttaatc cccatattca  22560
acatgatact gctgtatcac gttgtttagc tgcactgcta aaacataaaa ttgtagggag  22620
catgtaaatt ttacatagca catccttcca tagatgtaac aggaggtgta tataaaagaa  22680
tgtataattt gccatcaatc agaagtaaag gttatgcact aaccattcat agaaagtgat  22740
ataatcgatg tacttgatgc aaaatttttaa ggtgctcttc aaattatcac ggcaaaaagg  22800
caggaccctg atcttgtatt cctgcgaggt tgagaaaagg aaaaccgttc tcagtcaggt  22860
tcccaaaata gtgaaagaga tgaatacaga gaatgtagat atgattctta cttctcaaga  22920
aaacataggt acatttacca aattgtaacg gcaaaaagat ttatgtgaaa ggttttagcc  22980
ttgactatga agaagtcgca tttgagatga gaaagtatcg ccagctatgg tgaattatag  23040
taactaaagg tgccttgcat cacatatcat gtcaatatgt agatagttta tatgtaaata  23100
gataactctc atgtctttttt tttttgcaag cacatatcat ccctgaattg aggggattga  23160
gcttgctgtc aaagcataaa ctcctggaaa agctaaatga agtctctgat ttgtagtgca  23220
gagta                                                              23225

SEQ ID NO: 69         moltype = DNA  length = 23389
FEATURE               Location/Qualifiers
source                1..23389
                      mol_type = genomic DNA
                      organism = Nicotiana tabacum
SEQUENCE: 69
gcttccttgg ccaacaatca gttaatttgt aacttcgaat tcgagttcaa ttctacttcg    60
gagcgccatt tttgccccgt taaggtaact gtattgttca aaactttttt tgttttgtcg   120
atctattttt ttttgttttg ttttggaata ataactatag ttgtaatttt ttgggtgggg   180
gatgtggttg taatttagtc tagggttctg ttaggttggg gatgctagaa tcttgagaag   240
ctttataaat atacgaacat gcagttgtat gataaactga tagccggtag atcctgttgt   300
tgcgaacatg ctatgctagc tcaattctgc tctctgttcc cttttttctac tgttttcttt   360
ccctggtaaa gcaacacagg ctgacacaat cctagcccaa atgagagtaa caagtttcc   420
agtcttaga aggtgaaatc tataagcaaa tagatgtgaa tgtaagtgcc ttctggggca   480
tacgattaac aaaatagacgt gaatttaaat cactgcagga attgagagaa gaaatataga   540
gtgtgttcgg tataactgaa aatgtttca cttattctcc agtatttggc tggtgagggc   600
aaaatatttc cggagaatat ttacaaatgt ttgtttggtg agtggaaatt gtttcctaat   660
gttgttacaa aataatttac ttttttgattt catttaggcc ccttaaagtt cttgaaagat   720
taactgcaga aaaagtatt caacatgaca tgtcattctt gtaagaacaa gtcattaaga   780
aaaagaaaaa taatatatta aaattagaaa gtttctaaat atatgaaaat gtcaatctttt   840
tgtaaataat tcaagaaaat gaataatgac agtaatttaa aagtatcaca gatttacata   900
aagaaaggaa aaggaaaaga gagaatggta catgaaattt taaatgcttt ggctagattc   960
aaattccata ctcctattaa agaaaatgcc tgacaggtaa gaacatatag gtactgttgt  1020
gtcaacatgc aatagcattt ggtcactttg gagagagtat agagaaaaag agaaaatggc  1080
agagggaagt gggagggagg caagagccga ttgtctagcg ccaaaaagtt tgatatgttc  1140
tggatattgg aaattgactt tccttgggtt cttaggtaag ttagtttcat caaaattaaa  1200
ggaaatgtt ttcttagga aatgtttcc ccaacaattt aggccaacca aacatgtaa  1260
aattggaaaa gattatcaag aaaatgtttt ctttcatacc aaatacaccc ataagtagga  1320
gggattgtga taaattttgc aagttgttta tgtattttca gagatctatt tacctgtcat  1380
acatgttcta caaaacacga gtccatgtat atatcattgc acttctcctt tacaacttat  1440
ttaatttcta tttaaacagc tttagcgcgt aagagctgtt catttccttg aacaccattg  1500
ccaaagaacg gtttaatgag ggaaaatgaa aatttagcta tgttggcaag tcctgagtct  1560
tagagcaaat gatcttcatt gggtcttatt gtttccttgc aatacttgtt cagtcttgta  1620
agttctgatt ttcgctaaaa caactctttt tagtcgtcac ttgttactta caatttcttt  1680
tctcctaata gaaacgtgtc cggaaagctg acttttgacc ctgtatgtgt ttctggtttt  1740
tggagccttc agaatgatag tactagctgt tcaggtgtct attgagggtc ttcatcaaag  1800
caacagtaag gaaatagtta gaaaaactga aaaggacttc tccttaacgt gtttcagtct  1860
cttgatttta aggaaatgc attttgtaga tacattggca ttcattgaaa atggccttga  1920
ctcaataccct atgtcatgtg acatcaggaa gggaaagcaa tgattctgt ttctgtttca  1980
gtaataagtg atgaagtctt gtggcaactt ccatttgtaa attcatttg tacaagtgga  2040
ttatagaaaa ttagttgata agttcatacc tttctttttct ctacttttttc tcttgcaata  2100
tgagatatca caggttagag acatgatgca cattcatttg tggttcactt gaatgagaaa  2160
aaagtatatg tttcttctttt ttatgtttcg tttccttttg gttttcagta tctggtatcg  2220
aagttgtgta ataaacagtt tgttccacgc atgtgctgct gcagcattaa catggactag  2280
ccatcctgc gtaggagttc aatttgtgga attccgattt aagccaatca actgtggaat  2340
ctctaaaatat tttcattgaa ttcaccatac gttagatgat atgttttctc atggtccttt  2400
caagcacttc tccttctgtt taaatgtctc cacatgcttt tctgcccctt caatatcaga  2460
atttgtctaa aagttccttt ttctttaata aatctactgc tccaaatgaa tgatagaaga  2520
gttgtaaaga gttctgactt caagaccaag cacagttttg gttgggcttt caaattagct  2580
tataggaagt tgttcctaag atcgtcctga aacaaaatct tttcttttttg tagcttctac  2640
```

```
tgtattcatt catgctttaa tgcaatttat aacaaggttt ccoctaaata tccagagtct   2700
ttaattttgc tttcgagtcc cagctgcgca aaacgtatta ccgaagaata gttttctggg   2760
agatgttaca agagtttggt tagaagggtc tttcccttct aaagtgtttg gttcaagtta   2820
tctaaatgtc aagagccaat attttgttat taagctcaat tccttgccct gtttgggtgt   2880
ttttagaggt aatcaagatg atttttaaat gtttagtttc actaacattc taacctcaga   2940
attgggtgtg ccaatctgat atcaattcct ttgacttgga ttgtcagtca ggaagatcat   3000
atggcaactg gtatcgcttc aggaagcgga cagttacatt tgaggaagcc tgtctactgg   3060
aggagtagct atggaaaagc tcactgtcat tccaatgcga tcctgaatgg catgcaaaac   3120
cagatccctt ggtccgtatt aggatgatgt ttcttcgcct atctctcctc tctatctttc   3180
cctgctttat tatcttcatt ctattgcccc ttctcctctc ttttggggga ataattgtca   3240
aaatgtttta ttttggagct ttcaagatgt tattacattc caatttgtac ggacataggc   3300
attcacgtgt tggctgttgg actgtttatt cctcccatga gaacttactg gaaagaatct   3360
ttgtatacgt gtttaggcat aaaccagtaa tatcttttt catgagatac cagaatccta   3420
aaagtttttt ttttgagtca tttcctgatt cttaggaaa aaaagaaagg ttatcatttt   3480
catttctgg tggtgatatg ctacttaaat tttccaggtc ttattgggtt tccaaattct   3540
tgcgagttca tagaagtaac tactcacaat gtcaagtgaa aacaaactgg aagtctcaca   3600
ccggaacaat caattcttgc cagagagatg gctcaactag gtattttgat tttgctgtga   3660
ttggtagtgg aattgctggc cttagatatg tctagaagt tgcaaagcat ggaactgtga   3720
ctgtgataac caaggctgag cctcatgaga gtaacactaa ctatgctcaa ggtggtgtaa   3780
gtgctgtgtt ctgccctatg gattcagtgg agagccacat gcaagacaca attgtggcag   3840
gtgcttacct ctgtgatgag gagactgtta gagtaagttc acagaatatt attgtctctt   3900
cagttccgtg aagcagtttg cccttttca gttttttctc tttggaagtg gtttcctttg   3960
cttttccaaa ttttttccagg actgcttggt tggatgaata ggaaagttct ccatctttca   4020
ggttgaaacg aaaggaactt tctgtttaga cggcttttgc cacaggatct agaactgcca   4080
aaaaatggaa aagggtaaga gcaatcgggc agttaggctt gttttcaatt agaagctgaa   4140
gagccaagca ataatactaa agaaaggctc tatgcctatt cctttccttct gatgtaagtg   4200
cttacaagtt ggaaccgaag aaagagttgg agagttgaga aaccaatggt tggtaatatg   4260
gacgacttcc tctggtttat gtagtgctcc tattcttcat ggttcagatt gttgaattg   4320
tctttgaaca tcgtgagaag gcacgggaga aaatatgatt gatattattc tcatatgtta   4380
aacatgatac aatgagccct gtatatacat aacatgtact actcctaata catatgggat   4440
tagggttaca taactattct aacactcccc tcaagctggt gcatataaat catatgtacc   4500
gagcttgtta catatgtagt taatacgagg accagtgaga gacttggtga aaatatctgc   4560
aagctgatca ttcgacttca caaactttgt agcaatatct cccgagagta tctttctct   4620
gacaaaatga cagtcaatct caatgtgttt agttctctca tgaaacactg gatttgatgc   4680
aatatgaaga gcagcttgat tatcacacac aagtcccatc tgactaatct caccaaattt   4740
caactccttg agcaactgtt tgatccaaat tagctcacat gtcaccatag ccattgctcg   4800
atattctgct tttgcactag accgagcaac cacattctgt ttcttgctct tccaagatac   4860
caaatttcct cctactaaga cacaaatatcc agaaatagaa cgtctatcag aaggtgatcc   4920
tgcccaatca gcatctgagt atccaacgat ctgctcatgg cctcgatcct caaacaataa   4980
accttgcct ggagctgatt ttatatacag aagaatacga acaactgcat cccaatgact   5040
atcacacgga gaatccataa actgactcac aacactcaca ggaaaggaaa tgtcaggtct   5100
tgtcactgta aggtaattta atttaccaac caaccgccta tatattgtag gattgctaag   5160
aggctccccc tgtcctggca gaagtttaga attcggatcc atcggagtgt caacaggtct   5220
acaacctgtc attcctgtct cctcaagaat atctaaggca tacttccgtt gtgagatcac   5280
aatatctgag ctagactgag cgatctcaat acctagaaaa tactttagtt tgcccagttc   5340
cttagtctga aagcgttgaa agagatgttg cttcaattta gtaataccat cctggtcatt   5400
gccggtaata acaatattgt caacatagac caccggataa atatagagac tcgaagcaaa   5460
atgccgatag aatacagagt gatcagcttc actccgagtc atgccaaatt cctgataac   5520
tatgctgaac ttaccaaatc aggctcgagg agattgcttt agaccataaa gtaatcggcg   5580
caagtgacat actaggccac gagactcccc ctgagcaaca aacctaggtg gttgctccat   5640
ataaacttca tcctcaaggt caccgtgtaa aaaaacattc ttaatgtcca gctgatagag   5700
tggccaatgg cgaacaacaa ccatggatag aaaaaggcgg actgatgcta tcttagccac   5760
gggagagaag gtatcactgt aatcaagccc aaatatctga gtatatccct tgcaacaag   5820
acgagcctta agacgatcaa ccttaccatc cggatcaacc ttgactgcat acacccaacg   5880
acaaccaaca ctagatttac ctgaaggaag agggacaagc tcccaagtac cactcgtatg   5940
taaatcagac atctcgtcaa tcctgtcgcc atcctggatg agacaatgct tcacctgtag   6000
acttagggat ggaaacagag gacaaagaag atagaaaagc ataatagggt gaagacaaac   6060
gatgataact taaaccgaca taatgggat taggattaag ggtggtccgt ataccttcc   6120
gaagtgcaat cgatgtacta ggaagagaca gtccgcagt aggaccaggg tcaggtgcag   6180
gacgtgaatc agctgggcct gatgctgggt gcagatgacg atggtatgtc aagagtgttg   6240
ttcctgtggc agggagtgta agaggagcca cactagactc cccaacggtt ggaatgggta   6300
agacttctgt ggcggaaggt gaagaaggag atatagtaga atccttaaag gtcggtatg   6360
gtaagacctc agatatatca aggtggtcag aagaggtaaa gaaggttta gactcaaaaa   6420
atgtgacgtc ggaggacata aagtacctac gaagatcaag tgaataacaa cgatatccgt   6480
tctgaacacg agaataacca aggaagacac acttgagagc acgaggagct aacttatctt   6540
tcccaggggc taagttatga acgaaacaag tgctcccaaa aacacgaggg ggaacagagt   6600
ataagggtga cgggggaaac aatactgcat acaaaatctg attctggatg ggagatgaag   6660
gcatccaatt aaccaaataa caagctgtga gaactgcatc gccccaaaaa cgcaacggaa   6720
catgagattc aatgagaagt gtgtgagcag tctcaatgat gtgcctattc tttctatctg   6780
caaccctatt ttgctgaggg gtataaggac aagaggtctg atgaataatt tcttgagaag   6840
tcataaactg gtaaaattga gaggataaat actctaaggc attatcactg cgaaaagtgc   6900
gaataaaaac acgaaattga ttttttaatt cagcacaaaa attctggaat atagaaaca   6960
actcagaacg atctttcatt aagaaaatcc aagtacatct tgaatgatca tcaataaaac   7020
taacaaaata acgaaatccc aaggttgaat tgactctaac aggaccccat atatcagaat   7080
gaactaaaga aaaaatagac tctgcatgac tctcaatact acggggaaag gaggctcagg   7140
tatgtttctc gagctgacat gactctcatt ctaatgtaga taaactagac aaactaggca   7200
ccatcttctg aagcttggat aaacttggat gtcctaaatg tctgcgaatt aggtctggag   7260
gatctgtaac tagacatgcc ttggaggaat tgagtgagtt aaggtagtaa aggccttctg   7320
attcaagtct tgttccaatc gtctgtcccg tactgcggtc ctgcataata aaagaatcat   7380
```

```
caataaaata tatacccaa tggagggcac gagtcaaatg actaacagat gtaagattaa  7440
aaggacagcc agggacataa agaacggaat ctagagtgac agagggtagg ggattcgctt  7500
gtccaacacc ttttacttta gtttgagacc cattggctaa agtaacagtg ggaagagact  7560
gtgaatacgc aatatttgac aaaagtgatt tattaccaaa aatatgatca gaagcggctg  7620
agtccacaat ccattgtcca agagtactag actgggaaac acaagcaaaa gaattaccag  7680
caacagaagt atcagtctga gcaatagagg ctacttgtgg agatgtttgc ttatttgctc  7740
gatattgaag gaactcatta tactcccctt cagataaaga aaatccctgg ttacctgtag  7800
tctcggtctg agcaacataa gcattttggg gtgggcgacc atgtaaagaa tagcacacgt  7860
tactagtgtg tccaagttta tgacaataag agcacttgag tctagatttc caaaacgacc  7920
tcctcctcgt ctattctcca tagtttgaga tgcccgattg tccactgact gggatacgag  7980
gacagatgag tcaagtgtct gtgatgagct cactgggtga cttggtgctg cagcaaggcg  8040
aagtaatcga gagaataatt catcaactgt ggggacagtc ggtctagcca aaatctggtc  8100
acgtactgaa tcaaggtcat tagggagtcc agcgagtgta agaactacaa tatcctctgt  8160
cgttgctctt gttgctttc aatactagca gaaactgcca tcaacgtctc aaattcttcc  8220
atgactgcct gtacttgttc caagtaagta gatatatcca attcctgttt cttcaagctt  8280
gtcattcgca atattacatc atagagacga gatatgtcat tagtgtataa attacgagcc  8340
ttttcccaaa ctaaataaca tgtatggaat ggacggaaca agagcatcaa tttggaatca  8400
atagatcgcc acaagatact acataactga gcattgacct tctcccaaag tgttttggcc  8460
ttttcatcac cttcgctagc ctttttttgtt aaatgatctt gaactcgttg acctttacac  8520
cacaactcga aagacgaagc ccaagctaag tagtttgaac ctcccattaa aggttctgag  8580
gtaatcgtaa caccggaatt gccagaaccc gggttttttag acccgaaagc atcgactccc  8640
aaagacatcg ttggattatc accaaataac agaaagaatc actgacaac ttgctgaaac  8700
aggtgaagga aacactgttt ttgccggaaa attactgtag ctgccggaaa aagtcggtgt  8760
agtcgccgga aaaactcaaa gtggtcgaa tcaaacgaaa aaggtatgga gactcggaat  8820
tactaggcga tccgactgtc caactggaag tttttcaaaa aaatggttgg aacagtgctc  8880
acgcgccagt gcgtggggcg cttgggtcag atctcgccag aaagtttttg gcgcgtgagg  8940
gcgcgtgtac gtgagttttc cggtggggtt tactagggtt tggtcgccgg agcctgagga  9000
gtcttgtggt gttattggtt ttttgcacac accaacaaaa attgatgtga ttacgagcag  9060
ccttctaagt cgccgtaaaa ttgcacggcg acgaggtctt tcttcccgga agtcgctgga  9120
atgatgcaca acgataggtt tctcactaaa gctctgatac catgtgagaa ggcacgggag  9180
aaaatatgat tgatattaaa catgatacaa tgagccctat atatacataa tatgtcctac  9240
tcctaataca tatgagatta ggattacata actattctaa caaacattat gaaaagagag  9300
tgaaggtgac atgcaggaag gaagagataa ggataagaca ggaaattcac atgtgttgtc  9360
ttttggtttt attttgggat ttcatttagt ttgtgccaca gtaccatgtt ttttttttctt  9420
aatgagaaca cacttctgac ttccctaaat cagcaccaat tttctgaggg taactgctga  9480
taaggataga cactccaagg ttatccagga ttcctagctt aagttgtatc atataagttt  9540
ctctcctatc ccctcaagag tcctatgtac agaaaactct atcccttctc tctcgagctt  9600
tagctccgga gtccatttac ttttggttaat gctaacaact cttgcggagt tgtgaagtgc  9660
cttcttctgc cgagagtagt aaggcccaat ggacttcgca tctagtaggc ccattatcaa  9720
catacaatga gggagaaggg atagagttct ctgtatataa ctcttgtggg gataagagag  9780
aatcttatat gatacaactt aagctaggtg ttagcgaaa cgtaaaagaa agaacacaag  9840
atttaacgtg gttcggatca aaataatcct acgtccacca gagaacaatt gccctttaa  9900
tattaacaaa ggaaggggag atttcccaat tacacttaag agaatttctc tcttaactct  9960
ctactcacta caatgtattg tattattttg ggatgatttc tacaagtgaa ggagtgcatc  10020
tatttatata ggtaaagatg acatcaagag gaggtagttt gatgtcatgg gtgacatcaa  10080
aggaggaagc ttcctcctag catccacacc aactctttcc accaactctt ccaattggca  10140
tgccattgtt gactaaacat aaaccaacat tttcagcatg ccattgttaa ctaaacataa  10200
accaacattt tcactaggga tcctggattg ccttggagtg tctatcctta tcaaccgctt  10260
agtttgctgt atactatttt catttgtctc tgtaaatata tactggtttc aaggaagttt  10320
tgtgttgtgc ttggtagatg ggatatcaca actaatatct tcttatcagt tgataaaatc  10380
ctggtccatg taattctgct ttttatgcaa tctatgttct aaatgaaatt tatgagatgg  10440
ctgatttatt actccaaaat tgtgtttagt ctactctttt aaaatcttcg tttttataag  10500
tatatctcct ttctccaggt tgtgtgtacc gaaggacctg agagaattag agaactgatt  10560
gctatgggtg cttcattcga tcatggggag gacgggaatc tgcatctagc cagggaaggg  10620
ggccactccc atcgtcgaat tgtccatgct gctgatatga ctggcagaga gatagaaagg  10680
gccctattag aggcagtttt taagcatcct aatatacatg tgtttcaaca ccattttgct  10740
atagattttt tgaccactca ggtaattctt ttctttgctc ttcttgttta ttattgagaa  10800
aatacttctg ctctagcatc aatttggtcc aaaatgaagg gttgttgcta taatctaatt  10860
agtcttggca ttattcttt gctatgttg tttgtgcagt tgaactgttt ttccatgtaa  10920
acatttgcta atgttaattt gtatgccaaa tgcaggatgg ttctgacata atatgtcatg  10980
gcgttgatgc tataaacacg gaaacgcagg aagtaagtac agttgctttc actcatgttg  11040
acctccatgt attgaacatt tcctcacaat gacataaatt gatttcttag gcttctgcgc  11100
tcttactgtg agtttgtagg ttataagatt catttcaaaa gtgactttgc tggcatcagg  11160
tggagctggg catatctatc caagtactac taatccaccg gtatgagttt caatatcttt  11220
tcctccataa tattttcatt tatgagggat gtcactcctt ataatcaata agataatcag  11280
agtcctaaac agtgatatgg ggggagaagg tgggaaggga atggtggcta atactgtaat  11340
agttaatttc atgactagca tacatttgca tcttattgtt ggcgataagc ttcgtcacaa  11400
agtatctttc gtaactcata aggaccttaa caattgacat tggtgcaaac aacattccct  11460
agagtatgaa acatggcctg atttaattaa tttaaacccct acagcacttg catgttaagc  11520
taatgtgcaa ttagaaataa gggctggctg ccctaagcca caaaagagg aaaaacccaa  11580
atataccccct gtacttcgtg aaaaggtcta agatttattc tccctttgaa gtttggctcg  11640
ctggtgccct cgccgctaaa cttttggact atatttaccc ctatttgcta atggaccttg  11700
gtttgagact taacaacaac aacaatatac ccggtgtaat cccacaagtg gagtctgagg  11760
aagcgtgtca agataataga aggaaaaaga tatttaggag aggaaacaata aattgcacaa  11820
gacaagacaa gatttaggtg gttcgacaat ttttgcctac tccacggcca cacaaagaat  11880
agctctttat taattgaaga gagaaagaag aagtttggg atgatctaca aatgaaaatg  11940
tagacccta tttataagca tttgaatgcc ctgccgaggt aagcgcttac atcataagaa  12000
tgccgatgta agcgcttaca tcataagaat gctgaggtaa gcgcttacat cacaagaatg  12060
tcgatgtaag cgcttacatc atattttcat ctcttttcga ttttttcttttc tttgttttg  12120
```

```
tctactttca catacaacaa caagtttggt cctatcaatc tccctctcaa acctatgtta   12180
catcaagaaa gaaaataaag aaagatttgc tattctctgg tggcgccttc actctatcag   12240
tcttgaaggc taactgaggc agtgcacagc ctcagtttgt caacaccgac aactttggtc   12300
aacatgtctg acgggttctt taatcctggt atcttttgta gggaaagagt tccttcattt   12360
atcaactctc ggatatgatg ataccctcaac tggatatgct tcgatcttgc atgaaacact   12420
ggattcttgt caagatgaat tgcactctgg ctatcgctga aaagctcata attgtcctgt   12480
tctttaccta gctctttaag aaaattcttg agccaaatca tctcttttcc agcttctgag   12540
attgccatgt actctgcttc agtggtagat agagcaacac ttttctgaag tctggacatc   12600
caactaacag cagtaccacc aaaggtgaac atgtagccg tggtactttt tcgactatcc   12660
agatcgccac ctaaatttgc atcagtaaaa ccttgtaaga taatattgct cttttaaaa   12720
caaagtgcca tacctgaagt gcctttgaga tatcgcaata tccatttac accttcccaa   12780
tgctcctttc ctggatctga catgtatcta ctgacaactc caactgcatg gctatgtca   12840
ggtctagtgc aaaccatatc atacatcaaa cttcctactg ctgaagcata cagaactttg   12900
gacatgtact tcctttcttc atctgtctta ggtgattggt cctttgacag atttagatga   12960
cttccaagtg gagtgcttct ggtctttgca tcatgaagac tgaacctgct tagtaccttc   13020
tgtatgtact tttcttgaga caactttaag gttccttccg acctgtttct gctaatcctc   13080
atcccaagca tttgcttagc tggtcctaag tcttttcatat caaactcctc cgccagttgt   13140
tgcttaacca agttgatctc atttatgcta gatcctgcaa ttagcatatc atcaacgtac   13200
aacaataaaa tgatataggga ttcatcaaga tttttgatat aacagcaatg gtccatctca   13260
catcgtgtga aaccatttt atgcatgaat ccatcaaatt tcttgtacca ttgtcgggga   13320
gcttgtttca aaccatacaa actcttcttc aacttacaca caaggttttc tttaccagaa   13380
acttgaaaac cttcaggttg cttcatgtag atgtcttctt caaggtcctg actgcaagaaa   13440
gcagttttaa catctagctg ctccaaatgc aaattttctg cagctacgat acttagcacc   13500
aacctgatag tagttaattt gactacagga gagaagatct cggtgtagtc aattcattcc   13560
ttctgctgaa agtcttttac tactaatcgt gctttgtatc tcttcttacc atcatgctct   13620
tccttgactc tgtacaccca ctcgttctgc aatgccttct ttccttttgg taactccgta   13680
agtatccatg ttttattctt ttgaagagaa ttcatctctt ctttcatggc tagcttccac   13740
ttatcagagt ctatccacctg cattgcttca acaaaatgct ctggttctcc agcatcagta   13800
agaagtaaat agtgaagaga gagttaattt atttggagca ttcgtgactc ttttagatct   13860
cctcaatgta ggttcatgag taacagaatc cgaatttgat tcaggtcctg attccagatt   13920
tggttctgga tttgattctg tctctgagtc cacttcaggt tcggcttcta gttcttcttc   13980
aaattcggct tctagttctt catcttcaat ttcagaatca gttgtaatcc ctctagctac   14040
ttcatttct gagatttctt ctaactcaac tgtttcagac attgtctgtt tgttggtgtt   14100
ggttggttct acttcaagct tgtccttgta catcacattt tcattaaatg tgacattcct   14160
gtgtcttagg atctttctat tcggatcatc ccaaaaccga taaccaaaat tatcatcacc   14220
atagccaata aagaaacatt tctttgcttt aggatcaagc ttatctctat cattagagtt   14280
tacatgcaca taagcaacac aaccaaaaat tttcagatgt gagagagta cctcctttcc   14340
tgtccatacc tcctcaggaa tttcaaaatt cagcggtaca gagggtcccc tgtttatgag   14400
gtaagctgcc gtgttaacag cctcagccca aaaatacttc ggcaatccag aatgtattct   14460
catacttctg gctcgttcat tcagggttct gttcatcctc tcagcaacac catttttgttc   14520
cggtgttcca ggaactgtct tgatcattct gatcccattc tccgagcaaa atgctttgaa   14580
ctcttggcta tcatactctc ctccattgtc agacttcaga catttttaact ttagacttgt   14640
ctgattttca acttcagctt tccatctttt aaaggtaaca aatacatcag attttattttt   14700
cagaaaataa actcatacct ttcttgtgga atcatcaatg aaggtgacat aatagcgtga   14760
gcctcctaga gaggttacag gagctggtcc ccacacatct gtatgcacta gttccagctt   14820
ctctttcttt ggcgtccttc ccacctttga gaaactaact ctcttttgtt tcccgtaaat   14880
gcaatcttcg cacaaaccta attcaacatg ttttaggttt gacaacttct tttggatgc   14940
caaaagcttc attcccttct cactcatatg cccgagcctc cggtgccaca atgttgtatc   15000
acgaccatga tcaactgttg ctatagtatc tcttttctatt gcagttgcat gcagtgttcc   15060
ccttttgaag cctcgtgcca caaccaaatt cccttttggtt atcttccacg atccgttgtc   15120
gaatgttgtt gtatatccttt catcgtcaat ctgacccata gatatcagat tttttcttgag   15180
gccaggaaca tgtcgtacat tttgcaattt ccatagcgtg ccttgtgaag tctttatata   15240
aacttcacct tttccggcaa tgtcgagagg ttcgccgtct gctagataaa cttcccaaa   15300
ttttccagca atataattat gcaataattc tttgcatgat gtagagtgaa aggacgcacc   15360
tgagtccaga atccaagatt caactggact gtctgcacaa caaattagtg catcaaagac   15420
ttgttcagca attacatttg ctgaattttc ttccttcttc ttctttggtt ctctacattg   15480
actactgtag tgacccttt tatcgcaatt ccaacaagta atgccttgc gattttttgga   15540
ttgtcctctt ctccttgact ttgatctgcc acgaccataa atctgtcctc tttggttgat   15600
tctccccctg ctttcggtac taaaagcaga tcctggggaa tcacttgatt cttttcggcg   15660
aatatcttcg cttagaacca agtctctaat atcattcaat ttgagtttgg tacttcctga   15720
tgaactgcta actgcagtta ctgttgcaga ccaactctcc ggtagagatg atagtagaat   15780
caacgccctg atttcgtcat caattgttat attaacagaa ctcaactgag ttaatattgt   15840
attaaactca ttgatatgtt ccgtgactga tccaccttcg gtcattttta agtggaacaa   15900
tcgacgcatc aaatacactt tatttgaagc agatggcttc tcatacatat ttgataacgc   15960
cttcatcagg cctgcagtgg tcttctcgtt aatgatgtta aacgccacat ttcgtgttag   16020
cgtcaaacga atcacaccaa gagcttacg atctaataga tcccaatccg ctttggacat   16080
agtctccggt ttcacctcgg tcagaggtaa gtgtaatttt tctggtacaa atagtcctct   16140
atttgcattt tccagaatcc aaatctttg ccattgaact tgtcaatctt aaccttcccct   16200
tcttccgatg ccattttca caaaataat ttatgtgaat agtgcttgtg aatagtaacg   16260
atgatcaata gtgtcgcact attcttgtga atagtacctg caccaatact gtacttttct   16320
accaggatta cactgtctgt gctctgatac caattgttga ggaagcgtgt caagataata   16380
gaaggaaaaa gatatttagg agagaaacaa taaattgcac aagacaacac aagatttacg   16440
tggttcggca attttttgcct actccacggc cacacaaaga atagctcttt attaattgaa   16500
gagagaagaa agaagttttg ggatgatcta caaatgaaaa tgtagaccccc tatttataag   16560
catttgaatg ccctgctgag gtaagcgctt acatcataag aatgctgatg taagcgctta   16620
catcataaga atgctgatgt aagcgcttac atcataagaa tgctgaggta agcgcttaca   16680
tcataagaat gctgacgctt acatcatatt ttcatctctt tttgattttt ctttcttttg   16740
ttttgtctac tttcacatac aacaacaagt gtaatacccg ggtatattgt tgttgttgtt   16800
gttactcata ctgctgctac tcatctacgt gatcgagaag tcacaacaac aaattctggg   16860
```

```
cagaaccaaa ttggtacaac catcccagat atttcagagg aggaaagaag actcttggat  16920
gcaatggtga gttctaatcc cttaaatcct gtaaatccta cttgcttcta gcactggaat  16980
gttgagtatg agcaggaaca aattgcaaaa aatagaacaa catcaaagca aggcaatggt  17040
gacaaataca cttggtcaat ctgcattgaa gacaattgtt atcgaccaaa atgttccaca  17100
acctgtgcac ctggggagag acttgtatga agacggagga gaagaagcaa tgttacatca  17160
gtgtagagca gaggcagcaa gaaaagggga tctatcacca atgcatagcg gcaaaggtaa  17220
gaggactcat acaaggaaat ttagttggga cgacaaagtt agtgattttt taaatgttag  17280
gcgacctcca atgagagttg ccaaacaaaa gaaggccgcc ccaactacat ctacaaagtc  17340
caatcattca aaaaagaaat catgaatttt gaatacatct tgaagaattg gattgtgatg  17400
aaaaagagtt acaaactgaa gaaattacaa gttcggacaa gaagggacaa cattttttcg  17460
gaacaagtcg gtgaaggttc tattacggcc gatagagggg tggcggctcg ttgatgggt  17520
tgtaaagttg taatggtggt gaccggtgaa ggttctattt tggtgagacc atggaattga  17580
gaggggggaag gtgctagctg agaaagtgtt gaagtagtga agcggtgagg gagtctctgt  17640
ggggagctgt tggtgggttg gtgaggttgt ttggcggttt cagatgcaga ggtgtaacaa  17700
gtcggacaag aattggtcag acagggcagt ttttctggca atttttttt ttaaaatttt  17760
ttttgaaggt tctgtggtgc tcaaacttct atgaaattt cagggatggt taattatggt  17820
tggggtggtt gctgcctaga ggattagata aaggtggaag tggttgttta gttatagagg  17880
gagtactttg ggcgacggtg gagaatgtt tggggtgaga caattgtttg                17940
cgaattggat ggtgaaggtt gactagatga agtgggtttt gggcaacaac atgttgggga  18000
atggaagcat tactgtgtta caatggagaa ggggaataga tggagatctt tgcgggaaat  18060
gggggaaaat ggcctaaggg cagcgacggg gtgcagggt taatgggaga gggttaaagg  18120
gggagggagg tttattaatt agccacgtgt gggacatgtc acatgctggca cttctggtg  18180
ctaaactgag tttttgagat taactaaaaa agagatcaaa tgattttaa tcatcagctg  18240
ttagcaataa gggtagatat agtccaaaag tttaagggca ccagtgagcc aaactttaaa  18300
ccaagggtaa atctagacct tttcacaaag tacaaggaca aatatggacc ttccctccta  18360
cccctccccc caaaaaaann nnnnnnnnnn nnnnnnnnnn nnnnnnnnnn nnnnnnnnnn  18420
nnnnnnnnnn nnnnnnnnnn nnnnnnnnnn nnnnnnnnnn nnnnnnnnnn nnnnnnnnnn  18480
nnnnnnnnnn nnnnnnnnnn nnnnnnnnnn nnnnnnnnnn nnnnnnnnnn nnnnnnnnnn  18540
naaaaaaaaa aaaagaaac aataaagatt ctgggtatta acagatgatc ctttccttgg  18600
aagtgtggat tcttatctca taagagatga aggtaataaa ttcttattct atacaccaat  18660
attttctgt acaataaaag caagacacat tgttcaaagt tgtataacct gggttaggca  18720
tctactgtgg cgctgttatg ctcgttatca attgtttttc tcttacggtc atttctataa  18780
gttttggag ctactaattg gtggtgggc ccgattcttt ttttatattt gaccatttgt    18840
gcctttatta aggaacagaa aagttttaat ttgttgaatg tgggcatgct ggctgtaggt  18900
tgcaactgga gatggaatgg ctatggctca tcgagctcaa gctgtaattt ccaacatgga  18960
gtaagtgatc ctcagttgca ttgcattctt attgtccaat atcactgtgt ctgctttagt  19020
gagttgtgct gtaaaatctg ctaatctaga tttcatccat ttttttgcttt cttgatttct  19080
gcatcctgtt ctgcaattca ttctgaattt gcacttttga ctaaaaatac aaggtatgtt  19140
caaaatgttg tgcggggtga cattggatct gacttgaatt tttcaggata aagggcatca  19200
aatttttctc attgagggga tttaattgat atagaaaaga tttctcgact agcagtccgc  19260
tctctaattg atggtcctcc tttgatcgtc ttttggatgg tagacaagtc tttgtttgcg  19320
aggttgatga actatcccca acggttgcat tattaattac aattctcttc ttcatgttgc  19380
caggtttgtg caattccatc caactgcctt ggctgatgaa ggccttccca acagaccaag  19440
tgccagagag aatgctttt tgataactga agctgtcaga ggtgatggag gcatcctta   19500
caacttagat atggagagat ttatgccaat gtatgacaaa agagcagagc ttgccccgag  19560
agatgtggta gcaagaagta tagatgacca gctcaaaaag cgtggcgaaa agtatgttct  19620
tcttgatatc agtcacaagc ccagagagaa ggttctgtct cattttccta atatagctgc  19680
tgagtgtctc cgccatgggt tagacataac acagcagccg attccggtgg ttcctgctgc  19740
tcactacatg tgtggtggag ttcgtgctgg acttgagggt gagactaatg tgcaaggcct  19800
ttatgtggca ggtgaagttg catgtactgg tttacatggt gctaaccgac ttgctagcaa  19860
ctcgttgctt gaagcactag tgtttgcacg aagagctgta caaccttcaa ttgatcacgt  19920
gaatgtgtct agaattgatc actgtgcttc aagttggtgg ccgcgacctg tagcccccagt  19980
ggtaatagga gatacagtac ttaacaaagt cattcgtcgg acaagggaag tgaggaaaga  20040
actacagtca atcatgtggg aatatgttgg aattgttagg tctacctcaa gactaaccgc  20100
agctgagaag agaatcaatg agttggagtt ggaatggaga acatacctat ttcagcatgg  20160
ctgggaacca acaatggttg gactagaggc ttgtgagatg aggaatctct tctgttgtgc  20220
caacctggta gttagcagtg ctcttttctcg acacgagagt cgcgggcttc attacaccat  20280
tgattttcct catgttgtgg aaagcaagag gttgccaaca atcatttttc cttcacagcg  20340
aaatagctcg tggagctcac ggcaattaca caggcagcag atatgttaga tgctcttacc  20400
tattttgccaa tccttcctgc taaaacttgt caagcgcagg gcatgattag ttttaggta   20460
aagaagatgc ttatggtta ttgtcattct tcctgccatt acttttgggg cagggcaacg   20520
tcattctttg gtgaaaaaaa tatatatcta tacatacaac ccatataatt ttgaatgtgt  20580
ttccctattt tattcttata tagcatatt ttattatctgc taacttcaag cctgtctagt   20640
actcacacgt cccaaaagaa caacagttt taaagtaaaa gagtgtttga ttaattttc    20700
tgtctccata tagacatcaa ttttttgaat cttttaaat aaaattaagg gagatttgca   20760
catatacaca gtccaacaca ctgtattgca cctatgtaac taagttttc acttttcacc   20820
tgcatagcca acatttgttt tgcaacaatg tatatacatc tttaaacatt attgtatatt  20880
tgttgtaaac aatgtattaa ccttgtataa aatgtataat agtaaggtgt ttatacatac   20940
ttacactgtt atataaatta tacagtgtta tacaaaaatt gagtgtttga ttcaccttag  21000
aagcagtttt agctggcaaa gatcccccc ccagtctttg cactctcatc cttgcttata    21060
ttctgcacta attttctagt tgttcccttg atttctttgt ttgggatgga gaaggtgtg   21120
tggagggagt tggttcgatg acttccgttt gagtttcttc ttgtttcttg gtatgatcag  21180
acttggtttt ggtagatgac ctggtactag acttgggttt aaggtggtt tggtagatt    21240
tgatcatggt gaattttcta ggtttaaaaa ttttcttaga gccttacagg ggagaagtag  21300
ggatggcaat ggggaaggcc gggcgggtta agtcttcacc tactaaattt ttgccttgcc  21360
ttgcctcgtt tagttctttg ccccatttag atcatgccat gccctgcccc gtttagccct  21420
aaacttaata gttctttcat ttttatccat ctaactagcg caattgtttc taataatatt  21480
tagtaaatgg tctcctactt catcgattct gtaggagcct aaattgtcta aaaaaaaaac  21540
gccatcttcc ttcgtgcagt ttggtatctt ataccaatcg agagagataa tgttttttcc  21600
```

```
gtactttgta aacgaactac aagtcaacat tatgttgaac atttcgtact ctgtaaacga    21660
actacaagtc aacattatgt agtcaagtc aacattatgt attcgacggg aagcgtcaca    21720
gcctaggtta ggaacacctc cgagaaacct tacaataggc agatcacctc ttttattata    21780
gtagatagac aacatttgtg gactacgata aatgttttca accaatctga cattgtaaat    21840
gcacatgtaa tgccatgtat cagttcatac atgtggtaat ttaatgaagg attggaaata    21900
tacatttta ttttacaata gaagaatgct ttattagttc tttgtgcttg ccaatctgaa    21960
agaaatcatt tgatattctg tgacatcatg aagtcaacac caaaaaaagt ttaaatggtt    22020
gatagattct ttttgtcagt tttcacacag gtaacatctg ctgcaaatag aaagtcctct    22080
tctctgccaa ttatcttggc taagacatgc tgcctcgaca gcattcccca caaagcaggg    22140
aattttggtg tgttgttttt gtcctccgtg ttatcttta ctatccagct tttggagaag    22200
attgtagcaa ctttggacac cctatacagt acctatatca taatcagaac tactggtcta    22260
taaactccat tactttttca ctttgttccg caatcacctt tgaggttgtt gtatagagca    22320
agattgaggt tgtcgtaaat gtatatttat caccatgact gttttcatgg taaatgtcct    22380
gattaaggtg gcaagaccat aatgcatgtg ttgaatttac catctgcaca tatgaatgga    22440
gaagaaaaaa tgttaaaaca aaaaaagaac aaaaaaagac aatggtaata aagacgatga    22500
actaagttca aagcggctgc aaaagtgtga aggtgactg ttctctatca ttaaagttta    22560
tcttaaacta ttgatgtcat tcaggggtga caaaacagtc accaaatata agcatttttg    22620
ttcgggggtg aactacagag agtaggaatt catccttcaa tgtccctgtt tcaatccaac    22680
tatgtgtgca aaattttatc ttccttttaa tccccatatt caacatgata ctgctgtatc    22740
acgttgttta gctgcactgc taaaacataa aattgtaggg agcatgtaaa ttttacatag    22800
cacatccttc catagatgta acaggaggtg tatataaaag aatgtataat ttgccatcaa    22860
tcagaagtaa aggttatgca ctaaccattc atagaaagtg atataatcga tgtacttgat    22920
gcaaaatttt aaggtgctct tcaaattatc acggcaaaaa ggcaggaccc tgatcttgta    22980
ttcctgcgag gttgagaaaa ggaaaaccgt tctcagtcag gttcccaaaa tagtgaaaga    23040
gatgaataca gagaatgtag gtatgattct tacttctcaa gaaaacatag gtacatttac    23100
caaattgtaa cggcaaaaag atttatgtga aaggttttag ccttgactat gaagaagtcg    23160
catttgagat gagaaagtat cgccagctat ggtgaattat agtaactaaa ggtgccttgc    23220
atcacatatc atgtcaatat gtagatagtt tatatgtaaa tagataactc tcatgtcttt    23280
tttttttgc aagcacatat catccctgaa ttgaggggat tgagcttgct gtcaaagcat    23340
aaactcctgg aaaagctaaa tgaagtctct gatttgtagt gcagagtat              23389
```

SEQ ID NO: 70          moltype = DNA   length = 28331
FEATURE                Location/Qualifiers
source                 1..28331
                       mol_type = genomic DNA
                       organism = Nicotiana tabacum
SEQUENCE: 70

```
aacaaaccca gtttaatccc atacgtgggg tctggggagg gtagtgtgta cgtagcgtta      60
cccctaccta taaggcaga gaggcaaatt gtttcctaat gttgttacaa aataatttc     120
tttttaattt catttaagcc ccttaaagtt cttgaaagat taactgcaga ataaagtatt     180
caacatgaca tgtcattcgt gtaagaacaa gtcactaaga aaaagcaaaa taatatatta     240
aaattagaaa gtttctaaat atatgaaaat gtcaatcttt tttaaataat tcaagaaaat     300
gaataatgac agtaatttaa aagtatcaca gatttacata aagaaaggaa aaggaaaaga     360
gagaatggta catgaaattt caaatgcttt ggctagattc aaattccata ctctattaaa     420
agatatgcct aacaggtaag aacatatagg tactgttgtg tcaacatgca tagcgtttag     480
gtcactttgg agagagtata gagaaaaaga gaaatggca gagggaagtg ggaggggca     540
agaactgatt gtctagtgcc aaaacgtttg atatgttctg gatattgaa attgactaac     600
cttgggttct taggtaagtt agtttcaaca aaattaaagg aaaatgtttt ctttaggaaa     660
atgtttcccc cacaattag ggcaaccaaa catgggaaaa ttggaaaaga ttatcaaaaa     720
aatgtttttt cataccaaat acacccataa gtaggaggga ttgtgatcaa ttttgcaagt     780
tgtttatgta ttttcagaga tctatttacc tgtgatacat gttatacaaa acaagagtcc     840
atgtatatat cattgcactt ctcctttaca acttattca tttctattca aacagcttta     900
gcgcgtaaga gctgttcatt tccttgaaca ccactaccac caacaacaac ccagtaaaat     960
cctactaatg gggtctgggg agggtggtgt gtacgcagac cttattccta tcccgaagga    1020
gtagagaggc tgtttccgaa agaccctcgg ctcaagaaaa caaaagaca aaaggacaaa    1080
aggagacaat attagtatca cccacagcaat cataggaaaa ataagaacac catgaaatcc    1140
agaagaaaga tgcaaagcaa aagcgatacc tagtaaatag gtcctgcact gaaaagcgaa    1200
atagtaagac acaacattgc cactagctat cttagacaaa aatcctacct ggctagtccc    1260
acaatggtac aaagtaaggc aagactcaac tacctcctaa cctacaaccc taatactcga    1320
cctccattga acaccattga caagaaaga tttaataagg gaaaatgaaa atttagatag    1380
gttggcaagt ccttagtctt agagtaaatg atcttcattg ggtctattg tttccttgca    1440
atacttgttc agccttgtag gttctgcttt ttgctaaaac aactcttttt agtcgtcact    1500
tgtcacttac aatttccttt ctcctaatag aaacgtgtcc ggaaagctga cttttggccc    1560
tgtatgtgtt tctgttttt ggagccttca gaatgatagt actagctgtt caggtgtca    1620
ttgaaggtct tcattgaagc aacagtaagg acatagttag aaaaactgtt gctgaaacaa    1680
aaagagaaat cattgctttc gcttcctgat gttacatgac ataagtattg agtcaaggcc    1740
attttaaatg aatgccaatg tatctatgtt caggtgtcta ttgagggtct tcattgaagc    1800
aacagtaagg acatagttag aaaaactgaa aaggacttct tcttaacgtg tttcagtctc    1860
atgattttaa aggaaatgca ttttgtagat acattggcat tcatttaaaa tggccttgac    1920
tcaatactta cgtcatgtaa catcaggaag ggaaagcaat gatttctctt tttgtttcag    1980
caataagtga tgaagtcttg tggcaacttc catttgtaaa ttcattctgt acaagtggat    2040
tatagcaatt agttgataag ttcatacctt tctttctct acttttctc ttgcaatatg    2100
agatatcaca ggattagaga catgatgcac atacatttgt ggttcacttg aatgaaaaaa    2160
aagtatacgt ttcttctttt tatgtttcat ttcctttttg ttttcagta tctggtatgg    2220
aagttgtgta atgaacagtt ttttacacgc atgttctgct gcagcattaa catggactag    2280
ccatcttgtc gtgtgagtcc aatttgtgga attccagttt aagcccatca attgttgaat    2340
ctctaaatat tttcattgaa ttgaccatat gttagatgat atgttttctc attgtccttt    2400
caagcatttc tccttttgtt taaatgtctc cacatgcttt tctacccctt caatttctga    2460
tattttctaa aagttccttt ttctttaata aatctactgc tccaaatgaa tgaaagaaga    2520
```

```
gttgtgaaga gttctgactt caagaccaag cacagttttg gttgggcttt caattttagc   2580
ttttaggaag ttgttcctaa gattgtcctg aaaccaaatc ttttcttttt gtagcttcta   2640
ctatattcgt tcatgcttta atgcaattca taacaaggtt tcccttaaat atccagagtc   2700
tttaattttg ctttcgagtc ccagctgtgc aaaacgtatt actgaagaat agttttctgg   2760
gagatgttac aagattttgt tagaagggtc tttcccttct aaagtgtttg gttcaagtta   2820
tctaaatgtc aagagccgat attttgttat taagctcaat tctttgcctt gtttgggtgt   2880
ttttagaagt aatcaagatg atctttaaat gtttagtttc acaaacattc taacctcgga   2940
attgggagtg ctaatctgat atgaattcct ttgacctgga ttgtcagtca ggaagatcat   3000
atggcaactg gtatcgcttc agtaagcgga cagttacatt tgaggaagcc tgtctactgg   3060
aggagtagct atggaaaagc tcagtgtcat tccaatgtga tcctgaatgg catgcaaaac   3120
cagatccctt ggtacgtatt aggatgatgt tccttcacct atctctcctt ctctctctat   3180
cttccctgc tgtattatct tctttctatt gccccatctc ctctcttctg ggggaatgat   3240
tgccaaaata ttttattctg gagcttttaa gatgttatta catttcaaat tgtacggaga   3300
taggcattca cgcgttggct gttggactgt ttattcctcc aatgagaacg tactggaaag   3360
aatctttgta tacgtgttta ggcataaacc agtaatatct ttttttcatg agataccaga   3420
atcctaaaag ttttttctttt ttagtcattt cctgattctt tagaaaaaaa agaaaggtta   3480
tcattttcat tttctggtgg tgatatgcta cttaaatttt ccaggtctta ttgggttttcc   3540
aaattcttgc gagttcatag aagtaactat tcacaatgtc aagtgaaaac aaactggaag   3600
tctcacagcg gaacaatcaa ttcttgccag agagatggtc caactaggta tttcgatttc   3660
gcggtgattg gtagtggaat tgctggcctt cgatatgctc ttgaagttgc caaacatgga   3720
actgtagctg tgataaccaa agctgagcca catgagagta cactaacta tgctcaaggt   3780
ggtgtaagtg ctgtgctctg ccctatggat tcagtggaga gccacatgca agatacaatt   3840
gttgcaggtg cttacctctg tgatgaggag actgttagag taagttcaca gaatgttatt   3900
gtctcttcag ttccatgaag cagtttgccc tttttcagtt ttttctcatt ggagagtgtt   3960
tccttttact tttccaaatt tttcccgaaa tacttggttg gatgaatagg aaagttctcc   4020
atctttcagt ttgaaaccaa aggaccttc tgtttagacg ttttgcca caggatctga   4080
agctgccaaa aattggaaaa gagtaagagc aatgggcag ttaggcttgt tttcaatttg   4140
aagctgaagt gccaagcaac aatactacaa gaaaggctct atgtctattc cttgcttctg   4200
atataagtgc ttaaaagttg gaactgaaga aagagttgga gagttgggaa accaatggtt   4260
ggtaatatgg acgatttcca ctggtttatg tagtactcct attctttatg gttcagattg   4320
ttgacttttg tctttgaaca ttagggaaag agagtgaagg tgacatgcag gaaagaagag   4380
ataagaataa gacaggaaat tcacatgtgt tgtatcttgg ttttgattttg ggatttcatt   4440
tagacagtac catgtttttct tcttttaagg aaacacaca aaagtacctt taacacttct   4500
gacttcccta aatcagcacc aatttttga gggtaactgc tgataaggat agacactcca   4560
aggcgatcca ggattcctag tcatataaga ttctctccta tccccacaag ggtcctatgt   4620
gcagaaaact ctatcccttc tccctcgagc tttaacctag gaatccattt gattatgtga   4680
aaaagcacaa gagaaaaata tattattgat ttattaacta tgttacaatg agccctattt   4740
ataagtatac ataatacata caacaacaac aaccacccag tatagtccca ctagtggggt   4800
ctggggaggg tagtgtgtac gtagaccta cacctaccct ggggtagaga ggctgtttcc   4860
gataagaccc tcggctctct ccttccaaga actctccacc ttgctcttgg ggtgactcga   4920
actcacaacc ttttggttgg aagtggtggg tgctaaccac tagagcaacc cactcttgtc   4980
ataatacata acctactcct attacatacg ggactaggac taattatata tatatacaca   5040
cataactatc taacactcct cctcaagctg gtgcatataa attatatgta ccgaacttgt   5100
tacatatgta actaatacga ggaccagtga gaaacttggt gaaaatgtca gcaagttgat   5160
cattcgactt caaaaacttt atagcaatat ctcatgcgag tatttttttt ctgacaaagt   5220
gacagtcaat ctcaatgtgt ttagttctct catggaacac tggatttgat gcaagatgaa   5280
tagcagctg attatcacac acaagtttca tctggcttat ctcaccaaat tttaactcct   5340
tgagcaactg tttgatccaa attagctcac atattgccat agccattgct cgatattctg   5400
cttctgcact agaccgagca accacattct gtttcttgct cttccaagac accaaattac   5460
ctcctactaa gacacaatat ccagatatag aacgtctatc agaaggtgat tttgcccaat   5520
caacatctga gtatctaacg atctgctcat ggcctcgatc ctcaaacaat aatcccttag   5580
ctcgggctga ttttatatac cgaaaaatgc ggacaactgc atcccaatga ctatcacacg   5640
gagaatccat aaactgactc acaacactca taggaaagga aatatgaggt ctaatcactg   5700
tgaggtaatt taaattaccg accaaccgtc tatatcttgc gggatcgctg aacggctccc   5760
tcgtcctcgc agaagtttag aattcggatc catcggtgtg tcaataggtc tacaacctgt   5820
cattcctgtc ttctcaagaa tgtctaaggc atacttccgt tgtgagatca caatatctga   5880
gctagactga gcgacctcaa tacccaaaaa atactttaat ctgccagat ccttaccctg   5940
aaagtgctca aagagatgtt gcttcaactt agtaataccca tcctgatcat tgccggtaat   6000
aacaagatcg tcaacataat ggaccagata aatacagaga tttgaagcag aatgctgata   6060
aaacacggag tgatcagctt cactacgagc catgccataa tcctggataa ctgcgctgaa   6120
cttaccaaac taggctcgat gagattgctt tagaccataa actgaccggc gcaagcgaca   6180
tacaaagcca ctagactccc cctgagtaac aaactagatg gttgctccat ataaacttca   6240
tcctcaaggt caccatgaag aaaaacattc ttaatgtcca attgatagag aggccaatga   6300
cgaacaacat ccatggataa gaaaaggcgg actaatgcta ttttagccac gggagagaaa   6360
gtatcactgt aatcaagcct gaataattga gtatatcctt tggcaactag acgggcctta   6420
agttttcag cctggctatc cggaccaact ttgactgcat acacccaacg acaaccaaca   6480
gtagattttc ctgaatgaag aggaacaagc tcccaagtac tactcgtatg taaagcaaac   6540
atctcgtcaa ccatagcccg tcgccatcct agatgagata gtgcttcact tgtgacttta   6600
gggatgaaaa caaaggacaa aaaagataca aagcataat gagggtgatg acggcgcatg   6660
ataacttaaa ccgacataat ggggattagg attaagtgtg gttcatatac ctttccgaag   6720
tgcaatcggc tgactaggag gagcaagtcc gcagtaggag cagggtaagg tgcaggacgt   6780
gaatcagctg ggcttgatgc tgggcgcgga cgacgacgat aagtcaagag tggtgttcct   6840
gtggctgggg ttctaggagg agcaacacta gattccttaa cggtttgtgt gggtaagact   6900
ttgtgattg agaatgtagg aggagctata gttggtgggg ctagagctag aatggggcta   6960
taggtgatgg agacgtggag gaaggtgaag gggaaatagt gaatgaatct ccaaaaagat   7020
ggaactggta ataccctcaaa aatgtctaag tgaccaccta ggcatgtgaa gtatgactga   7080
gtttcaaaga aggtaacatc agcagacata aggcactgct ggaggtcagg cgagtagcat   7140
cgatacccct tacctaaaaaa tacacactta agagcacggg gagctaactt atcttttctt   7200
ggagtaaggt tatgaacaaa acatgtgctc ccaaagacac gaggtggaag agagaagaag   7260
```

```
ggtgagtgag gaaacaacaa agagaatgga acttgattct ggatagctga gtatgtcata    7320
caattaataa gataacaaga tgtgagaact gcatcccca aaaatcgcaa cggaacatga    7380
tattgtatga gtagggtacg ggcagtctca atgagatggc tattttttctt ttccgctacc   7440
ccattttgtt gagatgtata tggacaagat gtttgatgaa tgatcttatg agatttcata    7500
aactgctgaa atataggaga caaataatct ggggcatttt cactatgaaa tgtgcggata    7560
gaaatcccga attgattttg aatttcagca cggaaaacaa ctcagatcga ttttctcatca   7620
agaatatcca agtgcacctg gaataatcat caatgaaact atcaaagtag cggaatccca    7680
aggtagaact gacctgacta ggatccctaa catctgaatg gactaaagtg aaaggtgact    7740
ctgctcgatt atcagagcgt caagggaaac gagagtgagt atgcttaccg agctgacatg    7800
gctcacacac tagagtgtac aagtgagaca aatcaggtac cattttctga agttttgata    7860
aactgtgatg tcccaactgt ttatgtaata aatctggtga atcagtaata aaacaagttg    7920
ttgatatggg ttcatgtgat ttagcaagga taaggtaata aagtccatgt gattcatgtc    7980
cggtaccaat aatccgcccc gtactgcatt cctgcataaa aacaaggtca tcaagaaata    8040
aaacagaaca tttaagtgat ttggctaagc gactaacaac tatgagatta aaaggactac    8100
caggaacata aagaactgaa ttcaaaggta aagaaggaag tggacttgct tgacctattc    8160
cagttgccgc agtttgagac ccattggcca ttgtgaccat tggaagagat tgatgataag    8220
aaatagtagt gaaagcagat ttattaccat atgatgagac gctcctaaat caataaccca    8280
attactggga gaagaagatt gtgagacaca agtaacgcta gtacctgttt gaacaacatt    8340
agcaatctca taagatgtct tttacatgct ttgtacagaa ggaactctat atattccgat    8400
aaagaaacca tctggattgg attcaatgca ttggatccga cggatacaaa tgacattata    8460
atgttcacgc tggaaaaatc agaaaatatt ctggaaacta ctgttcacgc cagaaaaata    8520
tgaaagtggt aggaatttgg tttaaattgg atgggtaggc tcggaattgc aaggtaaaca    8580
agttgtcctg aagagtcgtc gccaaaaaag ggccgaaaat agcccacgc gcgtcgcgtg     8640
acatctgaac ttagccggta atttttttttt ctgtcggcgt gtgagggcgc gtggagggtg    8700
gtctgtcgga gatattttta cgggttggtc gtcaaaggct gatctactttc gtggtggtgt    8760
tggtttttgc acaacactga tgaaaagtgg ttagttcttg cggtagacct gtgtttgctg    8820
gaaagacttc cggttgactg atttctcttc ccggccgctg gaattatgc acaacgataa    8880
atctctcacg atttctctaa tagcatgtga gaaagcacgg gagaaaaata tattattgat    8940
ttattaacta cttataagta tacataatac ataacctact catattacat acgggactag    9000
gactgattat atatattcac attctaacaa attttcttaa tgctaacaac tcatgcagag    9060
ttgtacatg cccaattctg ctgagagtag taaggcccag cggatttcgc atctactagg    9120
cccattaaca acatacaaga gggagagggg atagagttct ctgtacatag gactcttgtg    9180
gggataggag agaatcttat tatatgatac aacttaagct aggaatcctg gatagctgg     9240
gagtgctgta tattattttc attttgtctct gtaaatatat actggcttca aggaagtttt    9300
tcgttcttgg gtgacgggac atcacaactg gtatcttctt atcagttgag aataatcgtcg    9360
tccatgcaat tgtacttttt atgcagtctc tgtgctaaat gaatttacaa gatgactgat    9420
ttattactcc aacattgtgt ttagtatact cttttgaagt cttcattttt ataagtgtat    9480
ctcctttctc caggttgtgt gtaccgaagg acctgagaga attaaagaac tgattgctat    9540
gggtgcttca ttcgatcatg gggaggatgg aaatctgcat ctagccaggg aagggggcca    9600
ctcccatcgt cgaattgtcc atgctgctga tatgactagc agagagatag aaagggcctt    9660
attagagca gttttaagc atcctaatat acatgtgttt caacaccatt ttgctataga     9720
tttgttgacc actcaggtaa gttattagt gtgaaaattt tgctatagtt gtgtaaaggt    9780
ggcaattgaa ctgttcagta aggatttaat gttaatttgt atgccaaatg caggatggtt    9840
ctgacatagt atgtcatggc gttgatacta taaacacgga aacacaggag gtaagtacag    9900
ttgctttcac tcatgttaac ctccatgttt tgaacatttc ctcaaaatga cataaattga    9960
tttctttggc ttctgcgctc ttattttgag tttgcaggtt ataagattca tttcaaaagt   10020
gactttgctg gcatcaggtg gagctgggca tacctatcct agtactacta atccgccggt   10080
atgggttcga atatctttctc cttcataatg ttgttagtta tgagggcact ccttgtaatc   10140
agtaagatta ttcagtccta aacagtgata tggggggaga aggtgggaa gggaatccct     10200
ggtgctgggg ggctaatagt tactttttatg actagcatac atatgcattt agttgttggc   10260
gataagcttc gtcacaaagt atcattcgta attcataagg accttaacaa ttgacattgg    10320
tgcaaacaac attccataga gtatgaaaca tggcctgatt taaaacccctt tcatgttaag    10380
ctaacgtgct aattagaaat aacagctgac tgccctaagt cacaaaaaag ggacaagtcc    10440
aaatttaccc ttgtactttg cgaaaaggtt tagatttatc atccggttga agttagtttg    10500
gctcactagt gcctcgctgt taaacttttg gacgatattt acccttattt gctaaaggac    10560
ctttgtttga ggtttaattg tctctaagta tactgaataa caccagagac tgccacgtgt    10620
cccacacgtg gcctgaaatt aatccctccc ctttaacctg accccgtttg accctgaaaa    10680
gtaaccccc tctcactaaa attaaccacc cctcttaccc ccacccttttt accacaaaca   10740
aggtggccaa cggaaaaaca actcctacac tgtccgtctt cattacactt ctgcaaccac   10800
caaacaacct caccaaccca ccaatagcac cccagagact cactgctcct ccacttcaac    10860
cctttctcgg cgaacacctt cccctcagtt ccacgatct caccaaaata gaaccttcat    10920
cagtcaccac cattacaact gtttacccga aaacggata gagttgaatt tattcgtagt     10980
tctaaggata tgtgatatag ctcaatacaa attgtaagga taaaggaaa atatcaaata   11040
tggaccgcaa agaagactaa ataaacaaag ttgtaacaaa agcgattttt gggaccaagc   11100
aagatgaatc agtttatgag gctaaaaaga ataactctcg aatatcagag aatatgttgc   11160
ttgaattaca atctcaaactc caaaaaaact gcccttccag aaatgataaa accctctttc    11220
atagtagagg gaccttactt taaatataat taaaaaatac tcagtgggag atccatgata    11280
aatcaactttt tccacaattc ctgccaagat tctctcatct agtggattg caacggctta    11340
tgtctgtgag tccgatctga ctcgggcttt tgatctcggc ttgagcttga ttctaactcg    11400
agctctcgat ctttgcctta agctcgatt taactcggaa ccttgaattg attcggggtc    11460
aatgttggtt ggtctctagc tcataagctt gatagcttta ctctgcatca tagttagatt    11520
tggatttgag ctcaataaca atatcgaact cgacattgat cggcccctcg ggttcgaggc    11580
ttgtttgttc catcttcgga aactatctcg aagtctcact tcgatcgatc atcattcgaa    11640
ctcgatcaga cgtgcgaagg ccgaaatcta tttcgaccgat atacagatag tcccctcgct    11700
tcttagaaag aatgtggtga gaacgatat gatcttttaa cggctcgatc ggattataac     11760
ctgacgtttc catcgggctc gatcatgacg catatgatag ctgttccgtc ggtttagtct    11820
ttcaaggcat ttaatgcatg tcagatggtg gtcggccact gctgatactg aaccgccatc    11880
gcttaaacct ataaataacc cttcctttta tcatttacca cttttacatc ttcaatcttc    11940
caaatttccc aagtcccttt tcgcattacc cgtaaatctg tgatttcttt ttacaaaagc    12000
```

```
ccctcttcaa ttctaccaaa tctttgtcac tttcttctat tcctcacttt tgaattcgaa   12060
aatggcgaaa acatcacaaa ccattcctca gaaagagaag gcttcatctt cacaatgtgc   12120
tgccgataag acaccagcaa aaccacgatc tgaggagtgc gttctcgggg cgtgtgttct   12180
tacttctgat tttaaggtcg ataaaggctc atcggtccct ggccgatgtg agccagtatc   12240
gaggtacata tgttcgataa ccgagaagca cctcaaacag ctaaagaaag attgcaattg   12300
ggataaaaaa gaaataatga ttccttcttc tgacgaagat atcacttctt acgtgaaagg   12360
gttttttgaat gtgtatactt accctttcac gttaggtccc ctcgattccg ttattattga   12420
cttctgtcgt caataccaaa taaccatagg ctaggtccat ccttctttct ggcggatcgt   12480
tatcctgatc cgatactttg tgagcaaaat cgaggggatg ccgttcaccc tcgaccatct   12540
tatccgattg taccgtcctc gacttttca aggagggtta ataaaacttc agcgtcgggc   12600
taccaaggct ctgttctcga gcattgacga ggacagggat cggggctgga tgggcaggtt   12660
cgttcgagtg aggacttcgg acctgattcc gaccgaaaag atgcccttc ccgaggagtg    12720
gaatatgaaa cgtaagtgtg atcctgctgt tacttctatt ttgttcttc atttcttttc    12780
tcaacgacac tcttcttttt gtgatgtagc ggttccctgg atgcccgag cagttctcga    12840
tctcaagaac tgggtacgag ctcttgtttc gacctttaca tacgccgagc gctcatgccg   12900
tgatttgtca aagggtggtg ggaggccaag aatcatggta agccccttc tagtactctt    12960
tgataattgc aacgaggtgg tttccaaata ttttaataaa ttttttcata tccaggtttg   13020
ggcaaagatg cagtttttgag gcccttgtcc aacgaggaag aaacttcggc tctgttcca   13080
aagccggtga agggaaataa aaagaaaaga gccaccgttc ccgaagatcc aaacccgaag   13140
aagaggacgg ctcgtaagcc gaacaagaat gccattcctt tgaccgtgga atcagttctg   13200
cgtctaaggg atgaagatga agaagaagaa gaagaagaaa atgatgggtc cgcgctggcg   13260
gcccgaacga agaaaccac cgatgcccca tcggcagctg gatcgatgat gctttatgag    13320
gctccgcctc gaactgagga tataccggag aaagattcgg gtggaatccc tgaattatcg   13380
gagatcgaag acgcatctca tcggagccaa cgggtgggtg atatgtctga aagggccctc   13440
gaatcccttc gaaccgaaga gaatgctcca agtaattcat ttggggcag cagcaatcga    13500
agattcgccc accttttccg cttttttcgc aggggtgatt cgggaagccc aagctctggg   13560
ggccctcgat ctagataggc ctcacgatga agaggatccc tttcgtgacc tgtttaccgg   13620
tatcgaggac gttgccggca ctggtgatga atcagatctt tttcacgggg tacggcaggc   13680
tttgaatcag gtaagcctta aaattatttt gtcggtacta tcttatgtt tacttttcat    13740
taacttcgtt tcttgtttct ttgtaggcaa cgacagttta tcgagaagca tgttctcggt   13800
cccaaaaagc gctgcgtcga tacgaggccg accttcaacg ggttactgat gagagaaact   13860
ccctaacact tcttttaggg cagagagaag aggaaataaa agacctccga gctgagttgg   13920
ccaaggctta tcgagatcag gccgatttgt ctgagcaggt aatgatactt ttaaaagcct   13980
atgggcttga taccggaacg atggctaatt tttcggtctc acagttgcag caaaaaattg   14040
agatgatcgg gaagcttcgt gaggaggtcg acgtgataaa aacagagtct ttgcagtgga   14100
aagaaggtat gaaccgctct gatgcagaga aagaaactgc tcgagcctag ttatcatctg   14160
ccgaaaccca acttcagaga atgaaagaaa aaggcctggt tcaagcaaga agaatagagg   14220
agctcgaggc tcggttggcc tctgtacttg ccaaggccga atctgatgcc gaaaaggcaa   14280
aagccgatgc ggatgcactc gtggccgtct atcgggccga tgctgaagct gccaggtct    14340
aagcaagaga ggcagccgag actgccgata ctcgagcaca ttgggtcgcc gaacttgcta   14400
agtgccgatc tcggagggaa acctcgagg agatccatgc tcgtggtttc gatctcgctg    14460
aagagataaa aagggccaaa gaactcgaag ccgatgctga agccctggtt tccgatgacg   14520
atgatgatga tgacaatgat gatgatgatg ggagtaagga cggatccgag aacgggggga   14580
agcccgatag agaagagacc gctcctgagg atgaccagga agcttagtcc ttaatttta    14640
cgttgtaatc aatcatgtag acaatttgt atatagacaa tattgccgac ttgcttctgt    14700
tttgtgaaga ctttattcat gccttatgaa tgttttcaca aggatttcaa caacttaatc   14760
aaatttggac ttcgtagcct ctataatcga gcgagtgctt attcaaactt gaagtgatgt   14820
agcccttagg cttattagtt gagtcaatga ttcgagctcg aagaaatata gcccgtaggc   14880
gtaatggtcg agtgggtgct tgctcgaact cgaaataaaa gtagcctgta ggcttagtag   14940
tcgagtgaat gattcgaact cgaagtaatc tcgaagtaat gtagcccata ggcgtaatgg   15000
tcgagtgcgt gcttgctcga actcgaaata aaagtagccc gtaggcttag tagtcgagtg   15060
aatgattcga actcgaagta atgtagcctg taggcgtaat ggtcgagtgc ttgcttgctc   15120
gaactcaaaa taagagtagc ccgtaagctt agtagtcgag tgaatgattc gaactcgaaa   15180
taatgtagcc cgtaggcgta atggtcgagt gagtgcttgc tcgaactcga ataaaagta    15240
gcccgtaggc ttagtagnnn nnnnnnnnn nnnnnnnnnn nnnnnnnnnn nnnnnnnnnn     15300
nnnnnnnnnn nnnnnnnnnn nnnnnnnnnn nnnnnnnnnn nnnnnnnnnn nnnnnnnnnn    15360
nnnnnnnnnn nnnnnnnnnn nnnnnnnnnn nnnnnnnnnn nnnnnnnnnn nnnnnnnnnn    15420
nnnnnnngta ggcttagtct tgaactcgaa ataaagtag cccgtaggct tagtagtcga    15480
gtgaatgatt cgaactcgaa gtaatgtagc ccgtaggcgt aatggtcgag tgatgtcttc   15540
tcgaactcga aataaagta gcccgtaggc ttagtagtcg agtgaatgat tcgaagtcga    15600
agtattgtag cccgtatgcg taatggtcga gtgagtgctt gctcgaactc gaaataaaag   15660
tagcccgtag gcttagtggt cgagtttatc ttaattctgt ttgcataata aatctccaaa   15720
tagaggaatt tttcttggat ataagatgtt ggcaaagagg agaactttct ttgcaagtca   15780
ctatacatgt gtttatgttt cgtgtctggg ttcgggccaa tcatgagc atggatcgtt    15840
ttgaccattt ggcttttaca acttttccta ttggaaaccc gttgttgcga aataactttc   15900
ttgcatcaga atttgatata ttcgagggct aatgccccc agtattcgag gtcgattgta    15960
aagaggcctc ggatactgtt gtaagcgcag cacgatcatt ggttgcctca ttaaaaacct   16020
tgccgaaaaa cccatttggg ataaaaccgg tctaagggaa aaagagtgca acacgtgctt   16080
tcagatctta aggcttcgta ttgaaggatc catcttagct cctgatcgaa cttctgcagg   16140
ggtcagtttt agaatgtaaa tgaatatggg agggtcgtac cttagcagta gtatcgtttt   16200
agatgtgaca cattccaatt gcttgataat tgtttgctgt ttataatgcc gagcttgtat   16260
gatcccttc cgacgttctc gagaacctga tatggtcctt cccagttcgg tcctagtttt    16320
ccttgttcgg atttcgggta ttgagggtga ctttccttag cactaagtcc tcgggcttga   16380
gccggag tttggttctt cgattataat atctttcgat tcgttgcttt tgggcggcca    16440
attggacgag agcagcttct cgttttttgt ccaataattc gaggctagtg ttcatagcct   16500
cgttatttga ttcttctgtc gtgtatcgaa atctggtact gggttcgccg acttcgactg   16560
gtatcaatgc ttcggaccca tatactaagg agaacggggt tgcccccgta ctggattttg   16620
acgtcgttcc atatgcccta aggactttgg gtaggatttc tctccacttt cttttagcgt   16680
cgttcagcct cttctttagg ttttgaatga tagttttgtt cgttgattcg acctgtccgt   16740
```

```
tcccactggg gtgatacggt gttgataata tccttcttat tttgtgatct tcgaagaatt   16800
tcgtcacttt gctgcccaca aattgtttcc cattgtcaca tactatttcg gcgggtatcc   16860
cgaatcggca tacgatatga tcccagatta agtctataac ttctctctct cttactttct   16920
cgaacgcctg tgcttcaacc catttagaga aatagtcagt cataaataaa atgaatttag   16980
ctttacctgg ggtcgatggc agagggccga cgatatccat tccccatttc atgaatggcc   17040
atggggatag gaccgagtga agttgttctc cgggttgatg tatcattggc gcaaaccttt   17100
gacatttgtc acattttcga acaaatgcct tcgcatcttt gcccatatcg atccaataat   17160
accctgccct gattattttt tcggactaat ggatcgacac cggagtgatt cccacaagtg   17220
ccctcgtgca cctcacgtaa gatgtaatcg gtatctcctg gacccaagca tactgccaat   17280
ggtccatcga atgtccttcg gtatagcgtt ccatctgaag ccaacgtgaa tcgagcagct   17340
ttagtccgta gggcccttga atctttagga tccgatggga gctttccgtt ctttaagtat   17400
tcaatatact tatttctcca atcccaggtt aagctcgtag aatttatctg ggcgtgtcct   17460
ttttcgatca cggatctcga gagttgaacg acagtccccg agctcaaatc accttcctcg   17520
accgatgatc ccaaattcgc aagtgcatca tcctcactgt tttgctctcg tggaacatgt   17580
tgtaaagtcc attgtttgaa atggtgcaaa gtgacatgta gtttgtccaa atacctttgc   17640
attctatctt ctcgaacttc gaaggttttg tttacttgac ttaccaccaa caagagtcac   17700
atttggcttc aatgacttct gctcccaagt тттттaacтag ctcgagacct gcaatcatga   17760
cctcatactc ggcctcgttg ttagtcaacc tggtagtttt aatagattgc ctaatagtgt   17820
tacccgtggg tggctttaaa actatgccta gcccggaccc cttcacgttc gaagccctat   17880
ccgtaaaaag ggtccatacc ctcgatgacg tacccgattt caacaggagt тcттттттcga   17940
cttcgggtac gagggttggc gtgaaatcgg ccacgaagtc tgctaaaatt tgagacttga   18000
tggccgtatg gggttgatat tcgatatcgt acccactgag ttcgacgatc catttggcca   18060
atcggcctga tagttcgggc ttgtgcaaaa tattacgaag tgggtaagtc attaatacgc   18120
atatggggta acattgaaag tacggtcgta actttctaga ggcgcttatc agtgcaagtg   18180
ccaatttttc taggtgcgga tatctagttt ctgcttctcc taaggttcga cttatataat   18240
aaatggaaa ttgcgtacct tgctcttccc gaactaggac accgcttact gcgatttcg   18300
atactgccaa gtataagcaa agtttttcgt ctgtttttgg tgtgtgaagt agtggtgggc   18360
tcgacagata ттgтттттagт тccтттттaaтg cctgttggca ttccggggtc caagcgaaat   18420
cgttcttctt tttgagtagg gagaaaaatt tgtgacttcg atctgatgat ctcgaaatga   18480
atcggcctaa ggccgcaatc cgtcccgtta gcctttgtac aactttcacg ctgtccacga   18540
tggtgatgtc ttcgatggct ттgaтттттaт cagggttaat ctcgattccc cgaтттттgaca   18600
ccatgaagcc gaggaacttg cccgaaccga ccccggaagc acatttttcg gggttgagct   18660
tcatgttgta ттттccтcaaa atctcgaacg tttcctgcaa atgggtcctc tgcgcgcagg   18720
gatttaacta gcatgtcatc aatataaact tccattgatt tacctatttg ттатттcgaac   18780
аттттттaттта ctaagcattg gtaagtagcc cctgcatttt тттagcccgaa gagcatcaca   18840
ttataacaat atgttccata tttggtgaca aacgaagtct тттcстgggттc ctccgagttc   18900
атстggатттт gатттатассс ggagtaggta tcgagaaaag tgaggatctc gtgaccggcc   18960
gtggcatcga tcatgcgatc gatgttgagt agcggaaaag аатсттттggg gcatgctttg   19020
ttcaaatcct tatagtccac acacattcta agtttattcc cttttttagg cactacaact   19080
atattggcta accatttggg atattccacc tcccgaattg accctatctt gagagattt   19140
gttacctcgt стттттатgаа tgcgtgtttt acctcggact gaggtcttct cttttgcttc   19200
accggtctga acttagggtc caagcttagc cgatgcgtcg ttatgtccgg tgggatccct   19260
gttatatcta aatgggacca ggcaaagcaa tcaatgttat cgataagaaa ttgaataagt   19320
ттстttссtgа gttcggggct aacccccgtt cccaggtata cctttcgttc gggccагtgc   19380
тагаттаgтg tgacttgctc cggctcctca attgttgatt tggtggcgtc ggatcgaggg   19440
atcctctgat catcatcttc ttcgatcttc cggttatctg gctgggtcga agccgatgtc   19500
tgtgattgct atttggtatc tcgttctcct tctgagcccg atccctttat tggtgaaggc   19560
gaggatattg gtttcgcttc ctcgacagcg aacatttctt ttgcggctgg ttgttctccg   19620
тасасtgтttt tgactcctct cgatgttggg aatttgagga ccтgggтgtаg ggtcgaaggt   19680
acaactctca tgttgtggat ccatggcctt ccgaaaaggg cgttgtatct catgtcgcct   19740
tcgatcacgt gaaacttcgt ttcctggatg gttccggcca cgtttattgg tagaattatt   19800
тсgссtтттgg tggtttcaca tgccatattg aatccgttta gaaccagagt tgcgggtacg   19860
atctggtcct gcaggccgag ctcttctacg accttcaatc tgatgatgtt ggccgagcta   19920
cctggatcaa tcaacacacg cттaaacттта gttttattca tgagtacgga tattaccggt   19980
gcatcgttat gaggttgtat gactccttct gcatcttcgt cattgaagga caaagttcct   20040
атggggтgтgт aatcttgaag tcgagatcga ttttctctca caatcgatgt ттагтgcgт   20100
ttaagcacta gtccctgagg ggtatcgcgc ccgccaatga tcatgtgaat gacgtgctgt   20160
ggttcttcct gttcgttttg cttgccgaaa tccctgtttt taaaatggtt cttcgcccta   20220
tcgctcaaaa atcccgaag gtgccccttg ttgaataacc gaactacttc ctctcttagt   20280
tgcctggaat cttctgttct gtggccatgg gtgccatggt attcgcatat ttgattggga   20340
ttcctccggg caggatcggt ttgcatgggt cgaggccatt tagtgtcttt gatgcgtccg   20400
atagctgata cgatgcgta tgcatcaacg ttgaagttat attccgataa ccgaggtgct   20460
tccttagatc cgacaggct atcgaaacta cttctgttta tcatccccg ggacccttga   20520
cctcgatcac ttttttttta tttgcttga ggttatgtct cgattcaccg actctgtgga   20580
ttccgttgta cggttggtat cgatccccaa tcagacctcg ttctcgatta gtatcccttc   20640
aattagcggg ttcagaccc aattgatcat cttgacctct aaтттгcгaт tggtaccgat   20700
tgtgcacgtc ggcacatgtg atggctgggt атттcgатcag gttatgcttt aattgccgtg   20760
aagccgtcga acttcgctcg ttcaaacctt gagtgaaagc ctgaacagtc caatcgtctg   20820
tgactggtgg caagttcatt cgttccattt gaaaacgaga tacgaactct ctcagcatct   20880
cgttatcctt ttgtcttaat cttgaagagg tccgatttcc ttgttgcgac тттттатggcg   20940
ccgacatgtg тттттcacaaa agaatctgct aacatgcgga acgagtcgat gaaatttggc   21000
ggtaggttgt aataccaaat cattgccccc ttcgagaggg tttctccgaa tgttttagc   21060
aacacagatt cgatttcatc gtcttctaaa tcattgccct tgatggcata tgtgtaagaa   21120
тgтgатgтgcт cgttgggatc ggtcgtcctg ttatatttgg gaatttcggg catacagaat   21180
tttttgggga ttgctttcag ggctgcgctc gaggaaaaag gtttttgcac gaaтттттттc   21240
gaatacaacc cтттттатcaт tggtggagct cccgggatct gatcgaccct agagtttata   21300
gtttctactt тттттатсgтт ggtttcgact cgctttgtga gttcctcgag caatttagca   21360
atttcggag tagtccccga tcttgctca tttgacttta ctatgctgg ttccgttctg   21420
tgagtgattt ctcggggtgg attgggctcc ggcctgcttt gtagctgggt ttggctctgc   21480
```

```
aactgagcta ttgctgcctg ttgggcttgc aacatttcga aaatcatacg caagttaacg   21540
ccgttttcct cgatgttttg ggtatctcga gccgcagacc gagtgccacc atggatgcta   21600
ttctcgggtt cagcatgtag gttcgcctca atgctacat gcgaattgat atcaattggc    21660
gctccgattc gagctccaac ggtgttcaca agtggtcttt cagtactggg tgtcaagttg   21720
ttttcgtctt gaagaccggc cccgttatcg atcggtgaag ccatttgatt gatggttagt   21780
cgtagctaat ccgaaattca agatattttc ggaaacaagc gtaaaacaca atggcgtgtt   21840
ttttcagatt cgtatcaaat aaccactgtt atccttagcc ccacagtggg cgccaaactg   21900
tttactcgaa aaacggatag agttgaattt attcgtagtt ctaaggatat gtgatataac   21960
tcaatacaaa ttgtaaggat aaaaggaaaa tatcaaatat ggaccgcaga gaagactaaa   22020
taaacaaagt tgtaacaaaa gcgattttt ggaccaagca agatgaatca gtttatgagg    22080
cttaaaagaa taactctcga atatcagaaa atatggtgct tgaattacaa tctaaactcc   22140
aaaaaaactg cccttccaga aatgataaac ccctctttat agtagaggga ccttacttta   22200
aatataatta aaaaatactc agtgggagat ccatgataaa tcagcttttc cacaatttct   22260
gccaagattc tctcatctag tgagattgca acggcttatg tctgtgagtc cgatctgact   22320
cgggcttttg atcttggctt gagcccgatt ctaactcgag ctctcgatct ttggcttaag   22380
ctcgattctg actcggaccc ttgaattgat tcggggtcaa tgttggttgg tctctggctc   22440
ataagcttga tagctttact ctgcatcata gttcgatttg gattcgaact caataacaat   22500
atcgaactcg acattgatcg gccctcggg ttcgaagctt gtttgttcca tcttcggaaa    22560
ccatctcgaa gtctcacttt gatcgattat cattcgaact cgatcacacg tgcgaaagcc   22620
ggaatccatt tcgaccgtat acaacagctt tacaacccca tcaacgagcc gcccctctac   22680
catagcaaaa cccatcgtct ttcattttta atggttgatg gtgtcgcata gggaaatttt   22740
tccggcgaca ttttttttta ttttttaaat tttgtgaaggt tctgtggtct caaactttta   22800
tgaaaattc agggatggtt aattatggtt ggggtgggtg ctacctagag ataacggtgg    22860
aagtgattgt ttaggtatag agggagtact ttgggtgacg gtggagaatg gtttggggtg   22920
ggattttggg aagctattgc ttgagtattg gatggtgaaa gttaactaga tgaagtgggt   22980
ttggggcagc aacatgttgg gcaatagaag cattactggtt ttgcaatgga gaagggaat   23040
agatggagct cttcgctgga agttgggcaa aatggctaa gagcagtgcc ggggtgcagg    23100
ggttaaaggg agagggttaa aggggcaggg aggtttatta attagccact tgtgggacat   23160
gtgacacatt ttggtgctaa acagagtaat tagatattaa ttaaaaaaag agattaatca   23220
actgttagca aataagggta gatatagtcc aaaagtttaa cggtgagggc atcagtgagc   23280
caaacttcaa accgagggta aatctagacc tttttgcaaa gtacaagggg aaatatggaa   23340
cacccccacc ccccaccccc caaannnnnn nnnnnnnnnn nnnnnnnnnn nnnnnnnnnn   23400
nnnnnnnnnn nnnnnnnnnn nnnnnnnnnn nnnnnnnnnn nnnnnnnnnn nnnnnnnnnn   23460
nnnnnnnnnn nnnnnnnnnn nnnnnnnnnn nnnnnnnnnn nnnnnnnnnn nnnnnnnnnn   23520
nnnnnnnnnn nnnnnnnnnn nnnnnnnnnn nnnnaaaaa aaaaaaaaaa aaaaaaaact    23580
taaagttctg ggtataatag atgatccttt ccttggatga gtggattctt gtcaagacac   23640
attgttcaac gttgtaataa cctgggttag gcatctgctg tggcgttgtt atgctcgtta   23700
tcaaatttgc cttttcttttg aaatcatttc tgtaagtttt tggagcaact aattggcggt   23760
ggggccaatt ctgttttat atttgacaac ttgtgccttt attaatgaaa aaaaaagttt    23820
ttttaatgtg ggcatgatgg ttgtaggttg caactggaga tggaatggct atggctcatc   23880
gagctcaagc tgtaatttct aacatggagt aagtgatcct cagttgcatt gcattctcat   23940
tgtacaatat ctctgcccct gctttagtga gttgtgctgt aaaatctgct aatcttgatt   24000
tcatccttt tttgccttct tgatttctgc atcttgttct gctattcatt cagaatttgc    24060
acttttgact aaaaatacaa gggtgtgttc aaaatgttgt gcgggatgat attggatatg   24120
caacttgaat ttttcaggat taagggcatc aaatttttctt cattgaggga tttagttgat   24180
gtagaaaaga tttctagact agcagtctgc tctctaattg atggtcctcc tttgatcatc   24240
ttttggatgg tagacaagtc tttatttgcg aggttgatga aggttgcatt agtaattaca   24300
attctcttcc tcgtgttgcc aggtttgtgc aattccaccc aaccgctttg gctgatgaag   24360
gccttcccat cagaccaaca agaaccagag agaacgcttt tttgataact gaagctgtca   24420
gaggtgatgg aggcatcctt tacaacttag atatggagag atttatgcca atgtatgatg   24480
aaaagacgaa gcttgccccg agatatgtgg tagcaagaag tatagatgac cagctcaaaa   24540
agcgtggtga aaagtatgtt cttcttgata tcagttacaa gccccgagag aaggttcttt   24600
ctcatttttcc taatatagct gctgagtgtc tccgccatgg gttagacata acacagcagc   24660
cgattccagt ggttcctgct gctcactaca tgtgtggtgg agtccgtgct ggactcgagg   24720
gtgagactaa cgtgcatggt cttatgtgt caggtgaagt tgcatgtact ggtttacatg    24780
gtgcgaaccg acttgctagc aactcgttgc ttgaagcact agtgtttgca cgaagagctg   24840
tacagccttc aattgatcac atgaatgtgt ctagaattga tcacggtgct tcaagttggt   24900
ggtcgcggcc tgtagctccc atgttactag gagatacagt acatggcaaa gtcattcacc   24960
ggacaaggga agtaaggaaa gaactgcagt caatcatgtg ggaatatgtt ggaattgtta   25020
ggtctacctc aagactaacc gcagctgaga agagttggag ttggaatggg                25080
aaacatacct atttcagcat ggctgggaac caacaatggt tggagtagag gcttgtgaga    25140
tgaggaatcc cttctgttgt gccaacctgg tagttaacag tgctctttct cgacacgaga   25200
gtcgcggtct tcattacacc attgattttc ctcatgttga ggaaagcaaa aggttgccaa   25260
cgatcatttt tccgtcacag cgaaatagct catggagctc gcggcaatta cacaggcagg   25320
agatatgtta gatgctctta cctatttgcc aatccttcct gctaaaactt gtcaagcgca   25380
gtgcatgatt agttttagg taaagaagat gctcatgggt tattgtcatt cttcccgcca    25440
ttacatttgg ggcagggcaa tgtcattctt tggtgaaata tatatatata tatatatata   25500
tatatatata tatactgtag acaataaatt tgcgtcagga aaataaaatc aagctgaaaa   25560
atattgcaac aatcgtagta ttttatttca aatatttgag tgttacaatc tgtatgaatc   25620
ctctgattct tcttttcaac ggtaaataaa agagcctttg agcttaatct tgaattttaa   25680
tttattttaa tccatgtgtt tggggcctaa tcttgatctt gacgtatttt taatccaagg   25740
gcttgcagct tgttcttgaa tcttcgtctt gatcttttaa tccgtagaac acttgaatgc   25800
ttgtagcttt tagagaaatc tgcagcgttt gatccacgag ctccctcttg cttttttgtta   25860
taacttctgg tccccttct gggttgtgaa aaccctcatt tatagttgtg gaagggagaa    25920
gttgtgataa gaacaagctc tttccgacca atcagattga ggagtgacaa tgccgcattt   25980
gattggccag aacatgtcac ttgcatatgt ggcgcgattt cattggcctt ttaatgtgac   26040
ttggcatgac ttgtcatttt gacacgtggc atgatcatat tggctctttc gtttgacttg   26100
gcgtgccacg tcatttgaca tgtggcacca aactgggcct ctaggaagat gacatcttgg   26160
gctcatcact ttagcccaat taaatgggtt agcccaatgg attaagactt atttatttaa   26220
```

```
tccataaaaa tgggacatat acaattaatc cacttatatt agtccaataa atttatttga  26280
actaatataa cttgaatttc aaatatagta caaattattt tatgaattta attttaataa  26340
aatttatatg tctacaaatg ctccctactt caagacttgt cagaacatag aagactaggc  26400
ttgaaatacc atgaatgcat gcaacggtca ttaatacccc ataactccaa tatgaaggaa  26460
atttcatgtc ttatttcctt taacgtttct gggcattagg acgagctttc aaagttttaa  26520
ttctccaaat ccaaagattt gcccagtaca gatttgatta aggaatcttt ggatggttaa  26580
ttgctttctt ctttttttgta atttcaaaca aagtgccaag aaattttgag atgataaagt  26640
gcacggaatt aagatgggat ttatattgac ttgagctttc ctagccatga tgcagcatct  26700
tccataagaa acttttgcaa gaattataga taacatctcc aacttcacgt ggcttaacaa  26760
ggaaactaca tactgctaat atagacttcc acactcttgg caccaattag aacaccgcca  26820
ctactagtag ccgaatcctt gttggataaa aagttagtct cgccgctttg caacttattc  26880
ccacatcggc agcatcattg taacatcttc tttcaaagat ctatataaac ccgcgtgctc  26940
gtatttgttc aacatccatt cgcagtattt gcaagccact tgagtctacc tttgtgaatt  27000
cggaagcatt aacgctgagg taatatcttc ttctttttt gtgcctttt ttttcactcc  27060
gttgtctctt tttaaaagt aacttcgtca aactacgaag ccctttataa gttcaagatg  27120
aaggcctta aaagtccgtg atgaagatct ttaaaatttg cggcggcaaa ccataaaagt  27180
tcgtgatgaa gacctttaaa atttgtggcg aaaatcctta aaagttcatg gccaagattt  27240
ttaaaagttc gtggtgatga ctttaaaaa tttgcggtgg agaccttaa aagtacgcga  27300
tgaagacctt taaaaatttg tggcgaagac ctttaaagt tcgcgatgaa gaccttaaaa  27360
atttgcggtg aagaccttta aaatttgcag cggaaaacca taaagttcg cgatgaagac  27420
ctttaaaatt tgcggtggaa aaccataaaa gttcgcgatg aaaaccttta aaatttgtgg  27480
cgaagatcct taaaagttcg cataaagatc cttaaagct cgtggtcaag atctctaaaa  27540
gtgcacagtg aagaccttta aaagttcacg gtgacgacct ttaaaagcat gcgatgaaga  27600
cccttaaaag ctcgcgcaaa gatccttata agttagtggt caagatattt aaaagtgcac  27660
attgaaaacc tttaaaattc gtggcgaaga tccataaaag ttcgtggtag aaatcttta  27720
aagtcggcag tggggactct ttaaagttcg ccacaagcac cttcaaaagt tcaagacaag  27780
caccttttaaa agttcgaaac atacgccttt taaaagttca gaacgaaaac cttaaaaacc  27840
cgaatgccat taaaagttcg agacgaacac ctttaaaagt tcgcaacgaa aatctttaaa  27900
atttcgaatg cctttaaaaa attcgagacg aacaccttta aaagttcgca acgaaaacct  27960
ttaaaacttc aaatgccttt aagttcgaga cgaacaactt taaaagtccg caacgaaaaa  28020
cttaaaaaaa gcaccttcat aattgtccct gactacattt taaaaccaac tttatattgc  28080
accacgctgc caatttcaga tttgcgcagt ctcatcaaaa tattcgtatc ttggtgtaga  28140
aatatcgaaa ttacaaacca tttgatttct tggaaactag acttcaaaat ctaaaacatg  28200
tccaaaacgt gcgatttaat accttaagga tagtttcaga taatattttg aagtcaactt  28260
aaaatttcga cacggtgaca atttcaaact tgcgcgattt taccaaaatt tttatatctt  28320
gatgtaagaa t                                                       28331
```